United States Patent
Furuta

(10) Patent No.: US 11,352,366 B2
(45) Date of Patent: Jun. 7, 2022

(54) 2-AMINOQUINAZOLINONE DERIVATIVE

(71) Applicant: SUMITOMO DAINIPPON PHARMA CO., LTD., Osaka (JP)

(72) Inventor: Tomoyuki Furuta, Osaka (JP)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

(21) Appl. No.: 17/392,949

(22) Filed: Aug. 3, 2021

(65) Prior Publication Data

US 2021/0380598 A1    Dec. 9, 2021

Related U.S. Application Data

(63) Continuation of application No. 17/427,831, filed as application No. PCT/JP2020/032622 on Aug. 28, 2020.

(30) Foreign Application Priority Data

Aug. 30, 2019  (JP) .............................. JP2019-158612

(51) Int. Cl.
| | | |
|---|---|---|
| C07D 491/107 | (2006.01) | |
| C07D 403/12 | (2006.01) | |
| C07D 405/12 | (2006.01) | |
| C07D 239/95 | (2006.01) | |
| C07D 403/04 | (2006.01) | |
| C07D 401/04 | (2006.01) | |

(52) U.S. Cl.
CPC ....... *C07D 491/107* (2013.01); *C07D 239/95* (2013.01); *C07D 401/04* (2013.01); *C07D 403/04* (2013.01); *C07D 403/12* (2013.01); *C07D 405/12* (2013.01)

(58) Field of Classification Search
None
See application file for complete search history.

(56) References Cited

U.S. PATENT DOCUMENTS

| | | |
|---|---|---|
| 2009/0036473 A1 | 2/2009 | Brown et al. |
| 2010/0160315 A1 | 6/2010 | Jessen et al. |
| 2012/0122890 A1 | 5/2012 | Perez-Medrano et al. |

FOREIGN PATENT DOCUMENTS

| | | |
|---|---|---|
| JP | 2009-530237 A | 8/2009 |
| JP | 2010-527967 A | 8/2010 |
| WO | WO 2007/104717 A1 | 9/2007 |
| WO | WO 2008/142140 A2 | 11/2008 |

OTHER PUBLICATIONS

Elkaschef, M et al., J Chem Soc Sec. C 1971 vol. 6, pp. 1055-1058.*
International Search Report dated Oct. 6, 2020 in PCT/JP2020/032622 filed on Aug. 28, 2020, 3 pages.
Molina et al., "Preparation and heterocyclization reactions of ferrocenylazido ketones. Useful building blocks for the synthesis of ferrocenyl-substituted azaheterocycles", Journal of Organometallic Chemistry, 1999, vol. 584, pp. 147-158.
Gao et al., "2-[2-(2-Anilino-4-oxo-3,4-dihydro-quinazolin-3-yl)phenoxy]-3-phenyl-quinazolin-4(3H)-one methanol hemisolvate", Acta Cryst., 2010, vol. 66, pp. o2075-o2076.
Gawad et al., "Synthesis and antitumor activity of some 2, 3-disubstituted quinazolin-4(3H)-ones and 4, 6-disubstituted-1, 2, 3, 4-tetrahydroquinazolin-2H-ones", European Journal of Medicinal Chemistry, 2010, vol. 45, pp. 6058-6067.
Marzouk et al., "Synthesis of Some Novel Quinazolinone Derivatives with Anticipated Biological Activity", Journal of Heterocyclic Chemistry, 2017, vol. 54, pp. 3331-3341.

(Continued)

*Primary Examiner* — Heidi Reese
(74) *Attorney, Agent, or Firm* — Oblon, McClelland, Maier & Neustadt, L.L.P.

(57) ABSTRACT

The present invention provides a 2-aminoquinazolinone derivative. The present invention is a compound represented by formula (1)

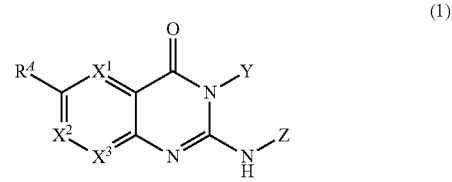

(1)

[wherein $X^1$ represents CR or N, $X^2$ represents $CR^2$ or N, $X^3$ represents $CR^3$ or N, Y represents an optionally substituted $C_{6-10}$ aryl or optionally substituted 6 to 10-membered heteroaryl, Z represents an optionally substituted $C_{6-10}$ aryl, $R^4$ represents a hydrogen atom, halogen, cyano, optionally substituted $C_{1-6}$ alkyl sulfonyl, optionally substituted $C_{1-6}$ alkyl, or optionally substituted $C_{1-6}$ alkoxy, and $R^1$, $R^2$, and $R^3$ independently represent a hydrogen atom, halogen, optionally substituted $C_{1-6}$ alkyl, or optionally substituted $C_{1-6}$ alkoxy] or a pharmaceutically acceptable salt thereof.

12 Claims, 1 Drawing Sheet

(56) References Cited

OTHER PUBLICATIONS

Registry [online], Jul. 20, 2005, [retrieved on Sep. 18, 2020], Retrieved from: STN, CAS Registry No. 856091-54-8, structural formula, 1 page.
Registry [online], Sep. 11, 2008, [retrieved on Sep. 18, 2020], Retrieved from STN, CAS Registry No. 1046700-93-1, structural formula, 1 page.
Registry [online], Sep. 11, 2008, [retrieved on Sep. 18, 2020], Retrieved from STN, CAS Registry No. 1048700-94-2, structural formula, 1 page.
Pacico et al., "New In Vitro Phenotypic Assay for Epilepsy: Fluorescent Measurement of Synchronized Neuronal Calcium Oscillations", PLOS ONE, 2014, vol. 9, Issue 1, pp. 1-9.
Shibuya et al., "Markedly reduced axonal potassium channel expression in human sporadic amyotrophic lateral sclerosis: An immunohistochemical study", Experimental Neurology, 2011, vol. 232, pp. 149-153.
Kanai et al., "Altered axonal excitability properties in amyotrophic lateral sclerosis: impaired potassium channel function related to disease stage", Brain, 2006, vol. 129, pp. 953-962.
Wainger et al., "Intrinsic Membrane Hyperexcitability of Amyotrophic Lateral Sclerosis Patient-Derived Motor Neurons", Cell Reports, 2014, vol. 7, pp. 1-11.
Palop et al., "Aberrant Excitatory Neuronal Activity and Compensatory Remodeling of Inhibitory Hippocampal Circuits in Mouse Models of Alzheimer's Disease", Neuron, 2007, vol. 55. pp. 697-711.
Basso et al., "An Explanation for Reflex Blink Hyperexcitability in Parkinson's Disease. II. Nucleus Raphe Magnus", The Journal of Neuroscience, 1996, vol. 16, No. 22, pp. 7318-7330.
Takarae et al., "Neural Hyperexcitability in Autism Spectrum Disorders", Brain Sciences, 2017, vol. 7, No. 129, pp. 1-12.

\* cited by examiner

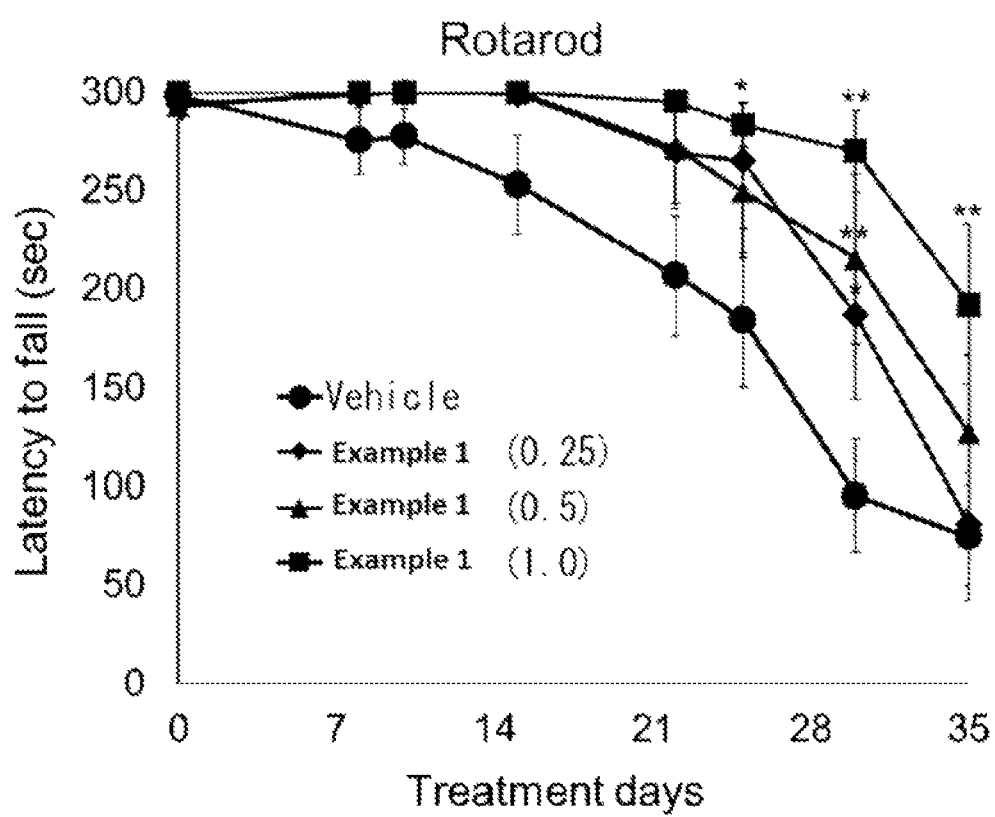

2-AMINOQUINAZOLINONE DERIVATIVE

This application is continuation of application Ser. No. 17/427,831, filed Aug. 2, 2021 which is a national stage application of PCT/JP2020/032622 filed Aug. 28, 2020 which claims priority to Japanese application 2019-158612, filed Aug. 30, 2019. the entire contents of all three applications are incorporated herein in their entirety.

TECHNICAL FIELD

The present invention relates to a 2-aminoquinazolinone derivative and a pharmaceutically acceptable salt thereof having an effect of suppressing nerve hyperexcitation, and a pharmaceutical composition comprising the same as an active ingredient.

BACKGROUND ART

It is known that hyperexcitation of the nerve is associated with various diseases. For example, epilepsy is a chronic disease with repeated paroxysmal motor, conscious, or sensory abnormalities and behavioral abnormalities from hyperexcitation of cerebral neurons. The mechanism of action of many antiepileptic drugs has not been clearly identified. It is understood that an effect is exerted by multifaceted effects of various mechanisms suppressing hyperexcitation of the nerve. In fact, it is reported that several antiepileptic drugs have an effect of suppressing hyperexcitation in neurons, so that compounds with an antiepileptic effect can be screened using the suppression activity as an indicator (Non Patent Literature 1).

It is reported that excitation at the nerve axon is elevated in amyotrophic lateral sclerosis patients (Non Patent Literatures 2 and 3). It is reported that motor neurons induced to differentiate from iPS cells derived from patients exhibits a phenotype of hyperexcitation, and the cell survival rate is improved by suppressing hyperexcitation with retigabine, which is an antiepileptic drug with a Kv7 activation effect (Non Patent Literature 4). In view of the above, an agent that suppresses nerve hyperexcitation has expectations as a therapeutic agent for epilepsy and amyotrophic lateral sclerosis. Hyperexcitation of the nerve is also reported in neurodegenerative diseases including Alzheimer's disease (Non Patent Literature 5) and Parkinson's disease (Non Patent Literature 6) and autism spectrum disorders (Non Patent Literature 7). Therefore, an agent that suppresses hyperexcitation of the nerve can be a therapeutic drug for these diseases.

Patent Literature 1 describes a 2,3-diaminoquinazolinone derivative having a Kv7 activation effect, but the chemical structure differs from that of a compound represented by formula (1) described below.

CITATION LIST

Patent Literature

[PTL 1] International Publication No. WO 2008/142140

Non Patent Literature

[NPL 1] Pacico, N. et al. PLoS One, 2014, 9(1), e84755.
[NPL 2] Shibuya, K. et al. Experimental Neurology, 2011, 232(2), 149-53.
[NPL 3] Kanai, K. et al. Brain, 2006, 129 (Pt4), 953-962.
[NPL 4] Wainger, B. J. et al. Cell Reports, 2014, 7(10), 1-11.
[NPL 5] Palop, J. J. et al. Neuron, 2007, 55, 697-711
[NPL 6] Basso, M. A. et al. The Journal of Neuroscience, 1996, 16, 7318-7330
[NPL 7] Takara, Y. et al. Brain Science, 2017, 7, 129

SUMMARY OF INVENTION

Solution to Problem

The present disclosure provides a 2-aminoquinazolinone derivative and a pharmaceutically acceptable salt thereof, as well as a nerve hyperexcitation suppressing agent comprising said compound or the like as an active ingredient, a drug/medicine/medicament and a pharmaceutical composition that are useful in the treatment or prevention of epilepsy and amyotrophic lateral sclerosis, use thereof, and a prophylactic or therapeutic method using said compound.

As a result of diligent studies, the inventors found that a compound represented by formula (1) described below or a pharmaceutically acceptable salt thereof (hereinafter, also referred to as the "compound of the invention") exhibits a potent nerve hyperexcitation suppressing effect to complete the present invention. The compound of the invention is provided in accordance with the present invention.

Specifically, the present invention is as follows.

[Item 1]

A compound represented by formula (1):

[Chemical Formula 12]

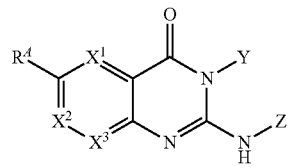

(1)

or a pharmaceutically acceptable salt thereof wherein $X^1$ represents $CR^1$ or N, $X^2$ represents $CR^2$ or N, $X^3$ represents $CR^3$ or N, wherein (1) if $X^1$ is N, then $X^2$ is $CR^2$, and $X^3$ is $CR^3$, (2) if $X^2$ is N, then $X^1$ is $CR^1$, and $X^3$ is $CR^3$, and (3) if $X^3$ is N, then $X^1$ is $CR^1$, and $X^2$ is $CR^2$, Y represents optionally substituted $C_{6-10}$ aryl or optionally substituted 6- to 10-membered heteroaryl, Z represents optionally substituted $C_{6-10}$ aryl, $R^A$ represents a hydrogen atom, halogen, cyano, optionally substituted $C_{1-6}$ alkylsulfonyl, optionally substituted $C_{1-6}$ alkyl, or optionally substituted $C_{1-6}$ alkoxy, and $R^1$, $R^2$, and $R^3$ each independently represent a hydrogen atom, halogen, optionally substituted $C_{1-6}$ alkyl, or optionally substituted $C_{1-6}$ alkoxy, provided that the compound is not a compound represented by formula (W-1):

[Chemical Formula 13]

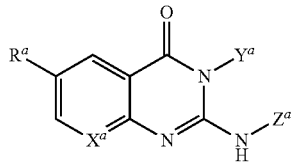

wherein
(A-1) $R^a$ is chloro, $X^a$ is CH, and $Y^a$ and $Z^a$ are both unsubstituted phenyl or 4-chlorophenyl;
(A-2) $R^a$ is chloro, $X^a$ is CH, $Y^a$ is 2-bromophenyl, and $Z^a$ is 4-chlorophenyl;
(B-1) $R^a$ is bromo, $X^a$ is CH, and $Y^a$ and $Z^a$ are both unsubstituted phenyl or 4-chlorophenyl;
(B-2) $R^a$ is bromo, $X^a$ is CBr, $Y^a$ is 2-chlorophenyl, and $Z^a$ is unsubstituted phenyl;
(C-1) $R^a$ is iodo, $X^a$ is CH, $Y^a$ is 4-methylphenyl, and $Z^a$ is unsubstituted phenyl or 4-methylphenyl;
(C-2) $R^a$ is iodo, $X^a$ is CH, $Y^a$ is 2-methylphenyl, and $Z^a$ is unsubstituted phenyl;
(D) $R^a$ is methyl, $X^a$ is CH, and $Y^a$ and $Z^a$ are both unsubstituted phenyl or 4-chlorophenyl;
(E) $R^a$ is cyano, $X^a$ is CH, and $Y^a$ and $Z^a$ are both unsubstituted phenyl;
(F-1) $R^a$ is a hydrogen atom, $X^a$ is CH, $Y^a$ is phenyl having position 2 substituted with ketone, and $Z^a$ is unsubstituted phenyl, 4-methylphenyl, 4-chlorophenyl, or 4-methoxyphenyl;
(F-2) $R^a$ is a hydrogen atom, $X^a$ is CH, $Y^a$ is 4-methylphenyl, and $Z^a$ is unsubstituted phenyl, 2-methylphenyl, 3-methylphenyl, 4-fluorophenyl, 3-chlorophenyl, 4-chlorophenyl, 3-methoxyphenyl, or 4-methoxyphenyl;
(F-3) $R^a$ is a hydrogen atom, $X^a$ is CH, $Y^a$ is 4-chlorophenyl or 4-methoxyphenyl, and $Z^a$ is 4-methylsufonylphenyl or 4-sulfaguanidylphenyl;
(F-4) $R^a$ is a hydrogen atom, $X^a$ is CH, and $Y^a$ and $Z^a$ are both unsubstituted phenyl, 2-methylphenyl, 4-methylphenyl, 4-fluorophenyl, 3-chlorophenyl, 4-chlorophenyl, 4-bromophenyl, 2-methoxyphenyl, 4-methoxyphenyl, 2,4,6-trimethylphenyl, 2,6-diisopropylphenyl, or naphthyl;
(F-5) $R^a$ is a hydrogen atom, $X^a$ is CH, $Y^a$ is unsubstituted phenyl, and $Z^a$ is 2-methylphenyl, 3-methylphenyl, 4-methylphenyl, 4-ethylphenyl, 4-methoxyphenyl, 4-bromophenyl, 4-methanesulfonylphenyl, or 2-hydroxyphenyl;
(F-6) $R^a$ is a hydrogen atom, $X^a$ is CH, $Y^a$ is 2-methylphenyl, 3-methylphenyl, 4-methylesterphenyl, 4-chlorophenyl, or 2-hydroxyphenyl, and $Z^a$ is unsubstituted phenyl;
(F-7) $R^a$ is a hydrogen atom, $X^a$ is CH, $Y^a$ is 2-bromophenyl, and $Z^a$ is 4-cyano-2-hydroxyphenyl;
(F-8) $R^a$ is a hydrogen atom, $X^a$ is CH, $Y^a$ is 2,3-dimethylphenyl, and $Z^a$ is 4-ethylphenyl; or
(F-9) $R^a$ is a hydrogen atom, $X^a$ is CH, $Y^a$ is 2-methylesterphenyl, and $Z^a$ is 3-methylphenyl.

[Item 2]
The compound or the pharmaceutically acceptable salt thereof according to item 1, wherein $X^1$ is $CR^1$.
[Item 3]
The compound or the pharmaceutically acceptable salt thereof according to item 1 or 2, wherein $X^2$ is $CR^2$.

[Item 4]
The compound or the pharmaceutically acceptable salt thereof according to any one of items 1 to 3, wherein $X^3$ is $CR^3$.
[Item 5]
The compound or the pharmaceutically acceptable salt thereof according to any one of items 1 to 4, wherein $R^1$, $R^2$, and $R^3$ are each independently a hydrogen atom, halogen, $C_{1-6}$ alkoxy, or $C_{1-6}$ alkyl (wherein the alkoxy group and the alkyl group are optionally substituted with 1 to 3 of the same or different substituents selected from the group consisting of halogen, hydroxyl, and $C_{1-6}$ alkoxy).
[Item 6]
The compound or the pharmaceutically acceptable salt thereof according to any one of items 1 to 4, wherein $R^1$, $R^2$, and $R^3$ are each independently a hydrogen atom, fluorine, chloro, $C_{1-6}$ alkoxy, or $C_{1-6}$ alkyl.
[Item 7]
The compound or the pharmaceutically acceptable salt thereof according to any one of items 1 to 4, wherein $R^1$, $R^2$, and $R^3$ are all hydrogen atoms.
[Item 8]
The compound or the pharmaceutically acceptable salt thereof according to any one of items 1 to 7, wherein $R^4$ is a hydrogen atom, halogen, cyano, $C_{1-6}$ alkoxy, methanesulfonyl, or $C_{1-6}$ alkyl (wherein the alkoxy group, the methanesulfonyl group, and the alkyl group are optionally substituted with 1 to 3 of the same or different substituents selected from the group consisting of halogen, hydroxy, and $C_{1-6}$ alkoxy).
[Item 9]
The compound or the pharmaceutically acceptable salt thereof according to any one of items 1 to 7, wherein $R^4$ is a hydrogen atom, fluorine, chloro, $C_{1-6}$ alkoxy, or $C_{1-6}$ alkyl (wherein the alkoxy and the alkyl groups are optionally substituted with 1 to 3 fluorine or methoxy).
[Item 10]
The compound or the pharmaceutically acceptable salt thereof according to any one of items 1 to 7, wherein $R^4$ is fluorine or chloro.
[Item 11]
The compound or the pharmaceutically acceptable salt thereof according to any one of items 1 to 10, wherein Y is $C_{6-10}$ aryl optionally substituted with 1 to 5 of the same or different substituents selected from the group consisting of halogen, cyano, $C_{1-6}$ alkoxy, methanesulfonyl, dimethylamino, and $C_{1-6}$ alkyl (wherein the alkoxy group, the methanesulfonyl group, the dimethylamino group, and the alkyl group are optionally substituted with 1 to 3 of the same or different substituents selected from the group consisting of halogen, hydroxy, and $C_{1-6}$ alkoxy), or 6- to 10-membered heteroaryl optionally substituted with 1 to 5 of the same or different substituents selected from the group consisting of halogen, cyano, $C_{1-6}$ alkoxy, methanesulfonyl, dimethylamino, and $C_{1-6}$ alkyl (wherein the alkoxy group, the methanesulfonyl group, the dimethylamino group, and the alkyl group are optionally substituted with 1 to 3 of the same or different substituents selected from the group consisting of halogen, hydroxy, and $C_{1-6}$ alkoxy).
[Item 12]
The compound or the pharmaceutically acceptable salt thereof according to any one of items 1 to 10, wherein Y is phenyl optionally substituted with 1 to 3 of the same or different substituents selected from the group consisting of fluorine, chloro, cyano, $C_{1-6}$ alkoxy, methanesulfonyl, dimethylamino, and $C_{1-6}$ alkyl (wherein the alkoxy group, the methanesulfonyl group, the dimethylamino group, and the alkyl group are optionally substituted with 1 to 3 of the same or different substituents selected from the group consisting of fluorine and hydroxy), or 6-membered heteroaryl optionally substituted with 1 to 3 of the same or different substituents selected from the group consisting of fluorine, chloro, $C_{1-6}$ alkoxy, and $C_{1-6}$ alkyl (wherein the alkoxy and the alkyl groups are optionally substituted with 1 to 3 fluorine).

[Item 13]

The compound or the pharmaceutically acceptable salt thereof according to any one of items 1 to 10, wherein Y is 6-membered unsubstituted heteroaryl or phenyl optionally substituted with 1 to 3 of the same or different substituents selected from the group consisting of fluorine, chloro, cyano, $C_{1-6}$ alkoxy, methanesulfonyl, dimethylamino, and $C_{1-6}$ alkyl (wherein the alkoxy group, the methanesulfonyl group, the dimethylamino group, and the alkyl group are optionally substituted with 1 to 3 of the same or different substituents selected from the group consisting of fluorine and hydroxy).

[Item 14]

The compound or the pharmaceutically acceptable salt thereof according to any one of items 1 to 10, wherein Y is unsubstituted pyridine, unsubstituted pyrimidine or phenyl optionally substituted with 1 to 3 of the same or different substituents selected from the group consisting of fluorine, chloro, cyano, methoxy, methyl, and —$CH_2OH$.

[Item 15]

The compound or the pharmaceutically acceptable salt thereof according to any one of items 1 to 10, wherein Y is unsubstituted phenyl, unsubstituted pyridine, or unsubstituted pyrimidine.

[Item 16]

The compound or the pharmaceutically acceptable salt thereof according to any one of items 1 to 15, wherein Z is $C_{6-10}$ aryl optionally substituted with 1 to 5 of the same or different substituents selected from the group consisting of halogen, cyano, $C_{1-6}$ alkoxy, methanesulfonyl, dimethylamino, $C_{1-6}$ alkyl ester, —$CONH_2$, and $C_{1-6}$ alkyl (wherein the alkoxy group, the methanesulfonyl group, the dimethylamino group, the alkyl ester group, and the alkyl group are optionally substituted with 1 to 3 of the same or different substituents selected from the group consisting of halogen, hydroxy, $C_{1-6}$ alkoxy, and —$NR^4R^5$), and $R^4$ and $R^3$ each independently, and if there are a plurality of instances of $R^4$ and $R^5$, they also independently represent a hydrogen atom, an optionally substituted $C_{3-6}$ alicyclic group, and optionally substituted $C_{1-6}$ alkyl, wherein $R^4$ and $R^5$, together with the nitrogen atom to which they are attached, may form a 4- to 10-membered nitrogen-containing non-aryl heterocycle (wherein the nitrogen-containing non-aryl heterocycle is optionally substituted).

[Item 17]

The compound or the pharmaceutically acceptable salt thereof according to any one of items 1 to 16, wherein Z is phenyl optionally substituted with 1 to 2 of the same or different substituents selected from the group consisting of fluorine, chloro, cyano, $C_{1-6}$ alkoxy, methanesulfonyl, dimethylamino, methyl ester, —$CONH_2$, and $C_{1-6}$ alkyl (wherein the alkoxy group, the methanesulfonyl group, the dimethylamino group, the methyl ester group, and the alkyl group are optionally substituted with 1 to 3 of the same or different substituents selected from the group consisting of fluorine, hydroxy, $C_{1-6}$ alkoxy, and —$NR^4R^5$ and $R^4$ and $R^3$ each independently, and if there are a plurality of instances of $R^4$ and $R^5$, they also independently represent a hydrogen atom, an optionally substituted $C_{3-6}$ alicyclic group, and optionally substituted $C_{1-6}$ alkyl, wherein $R^4$ and $R^5$, together with the nitrogen atom to which they are attached, may form a 4- to 10-membered nitrogen-containing non-aryl heterocycle (wherein the nitrogen-containing non-aryl heterocycle is optionally substituted).

[Item 18]

The compound or the pharmaceutically acceptable salt thereof according to any one of items 1 to 17, wherein Z is phenyl optionally substituted with 1 to 2 of the same or different substituents selected from the group consisting of fluorine, chloro, cyano, $C_{1-6}$ alkoxy, $C_{1-6}$ alkyl, —$CH_2OH$, and —$CH_2NR^4R^5$, and $^4$ and $R^3$ each independently, and if there are a plurality of instances of $R^4$ and $R^5$, they also independently represent a hydrogen atom, an optionally substituted $C_{3-6}$ alicyclic group, and optionally substituted $C_{1-6}$ alkyl, wherein $R^4$ and $R^5$, together with the nitrogen atom to which they are attached, may form a 4- to 10-membered nitrogen-containing non-aryl heterocycle (wherein the nitrogen-containing non-aryl heterocycle is optionally substituted).

[Item 19]

The compound or the pharmaceutically acceptable salt thereof according to any one of items 16 to 18, wherein $R^4$ and $R^3$ each independently, and if there are a plurality of instances of $R^4$ and $R^5$, they also independently represent a hydrogen atom, a $C_{3-6}$ alicyclic group, and $C_{1-6}$ alkyl (wherein the alicyclic group and the alkyl group are optionally substituted with 1 to 3 of the same or different substituents selected from the group consisting of halogen, hydroxy, a $C_{3-10}$ alicyclic group, $C_{1-6}$ alkoxy, a $C_{3-6}$ alicyclic oxy group, and a 4- to 6-membered non-aryl heterocyclic group), wherein $R^4$ and $R^5$, together with the nitrogen atom to which they are attached, may form a 4- to 10-membered nitrogen-containing non-aryl heterocycle (wherein the nitrogen-containing non-aryl heterocycle is optionally substituted with 1 to 5 of the same or different substituents selected from the group consisting of halogen, hydroxy, $C_{1-6}$ alkyl, and $C_{1-6}$ alkoxy).

[Item 20]

The compound or the pharmaceutically acceptable salt thereof according to any one of items 16 to 18, wherein $R^4$ and $R^3$ are each independently, and if there are a plurality of instances of $R^4$ and $R^5$, they are also independently $C_{1-6}$ alkyl (wherein the alkyl group is optionally substituted with 1 to 3 of the same or different substituents selected from the group consisting of fluorine, hydroxy, a $C_{3-7}$ alicyclic group, $C_{1-6}$ alkoxy, and a 4- to 6-membered non-aryl heterocyclic group), wherein $R^4$ and $R^5$, together with the nitrogen atom to which they are attached, may form a 4- to 7-membered nitrogen-containing non-aryl heterocycle.

[Item 21]

The compound or the pharmaceutically acceptable salt thereof according to any one of items 16 to 18, wherein —$NR^4R^5$ is, and if there are a plurality of instances, they are each independently formula (AM-1), (AM-2), (AM-3), (AM-4), (AM-5), (AM-6), (AM-7), (AM-8), (AM-9), (AM-10), (AM-11), (AM-12), (AM-13), (AM-14), (AM-15), (AM-16), or (AM-17):

[Chemical Formula 14]

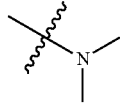

(AM-1)

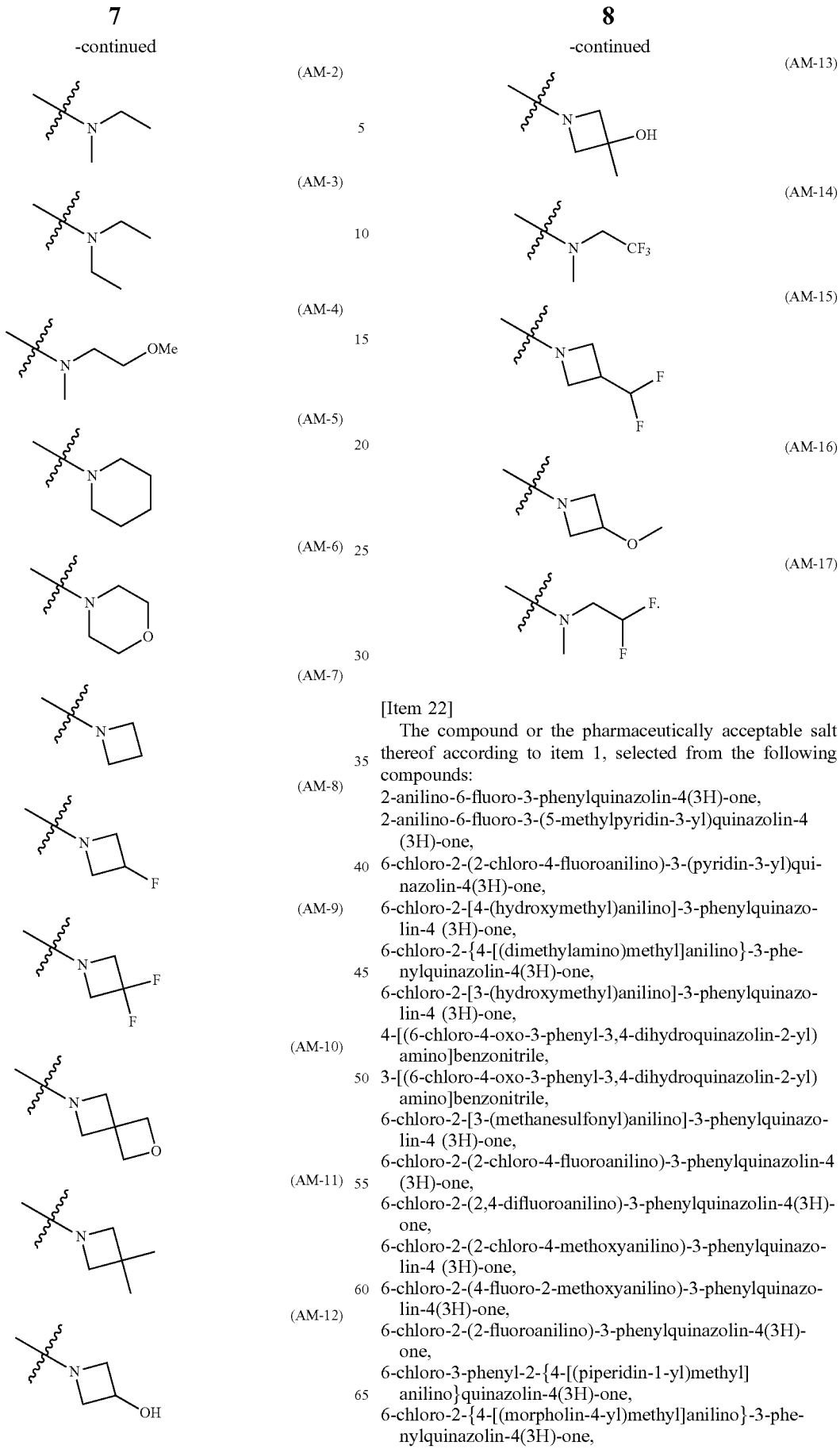

[Item 22]

The compound or the pharmaceutically acceptable salt thereof according to item 1, selected from the following compounds:

2-anilino-6-fluoro-3-phenylquinazolin-4(3H)-one,
2-anilino-6-fluoro-3-(5-methylpyridin-3-yl)quinazolin-4(3H)-one,
6-chloro-2-(2-chloro-4-fluoroanilino)-3-(pyridin-3-yl)quinazolin-4(3H)-one,
6-chloro-2-[4-(hydroxymethyl)anilino]-3-phenylquinazolin-4 (3H)-one,
6-chloro-2-{4-[(dimethylamino)methyl]anilino}-3-phenylquinazolin-4(3H)-one,
6-chloro-2-[3-(hydroxymethyl)anilino]-3-phenylquinazolin-4 (3H)-one,
4-[(6-chloro-4-oxo-3-phenyl-3,4-dihydroquinazolin-2-yl)amino]benzonitrile,
3-[(6-chloro-4-oxo-3-phenyl-3,4-dihydroquinazolin-2-yl)amino]benzonitrile,
6-chloro-2-[3-(methanesulfonyl)anilino]-3-phenylquinazolin-4 (3H)-one,
6-chloro-2-(2-chloro-4-fluoroanilino)-3-phenylquinazolin-4 (3H)-one,
6-chloro-2-(2,4-difluoroanilino)-3-phenylquinazolin-4(3H)-one,
6-chloro-2-(2-chloro-4-methoxyanilino)-3-phenylquinazolin-4 (3H)-one,
6-chloro-2-(4-fluoro-2-methoxyanilino)-3-phenylquinazolin-4(3H)-one,
6-chloro-2-(2-fluoroanilino)-3-phenylquinazolin-4(3H)-one,
6-chloro-3-phenyl-2-{4-[(piperidin-1-yl)methyl]anilino}quinazolin-4(3H)-one,
6-chloro-2-{4-[(morpholin-4-yl)methyl]anilino}-3-phenylquinazolin-4(3H)-one, 2-{4-[(azetidin-1-yl)methyl]anilino}-6-chloro-3-phenylquinazolin-4(3H)-one,
6-chloro-2-(4-{[ethyl(methyl)amino]methyl}anilino)-3-phenylquinazolin-4(3H)-one,
6-chloro-2-{4-[(diethylamino)methyl]anilino}-3-phenylquinazolin-4(3H)-one,
6-chloro-2-(4-{[(2-methoxyethyl)(methyl)amino]methyl}anilino)-3-phenylquinazolin-4(3H)-one,
6-chloro-2-{4-[(2-oxa-6-azaspiro[3.3]heptan-6-yl)methyl]anilino}-3-phenylquinazolin-4(3H)-one,
6-chloro-2-{4-[(3,3-difluoroazetidin-1-yl)methyl]anilino}-3-phenylquinazolin-4(3H)-one,
6-chloro-2-{4-[(3,3-dimethylazetidin-1-yl)methyl]anilino}-3-phenylquinazolin-4(3H)-one,
6-chloro-2-{4-[(3-fluoroazetidin-1-yl)methyl]anilino}-3-phenylquinazolin-4(3H)-one,
6-chloro-2-(4-{[3-(difluoromethyl)azetidin-1-yl]methyl}anilino)-3-phenylquinazolin-4(3H)-one,
6-chloro-2-{4-[(3-methoxyazetidin-1-yl)methyl]anilino}-3-phenylquinazolin-4(3H)-one,
6-chloro-2-(4-{[(2,2-difluoroethyl)(methyl)amino]methyl}anilino)-3-phenylquinazolin-4(3H)-one,
6-chloro-2-(3-fluoroanilino)-3-phenylquinazolin-4(3H)-one,
6-chloro-2-(4-chloroanilino)-3-phenylquinazolin-4(3H)-one,
2-anilino-6-chloro-3-phenylpyrido[3,4-d]pyrimidin-4(3H)-one,
6-chloro-2-(4-chloroanilino)-3-phenylpyrido[3,4-d]pyrimidin-4(3H)-one,
2-anilino-6-chloro-3-phenylpyrido[2,3-d]pyrimidin-4(3H)-one,
2-anilino-6-chloro-3-phenylpyrido[3,2-d]pyrimidin-4(3H)-one,
2-anilino-6-chloro-3-(pyridin-3-yl)quinazolin-4(3H)-one,
2-anilino-6-chloro-3-(pyridin-2-yl)quinazolin-4(3H)-one,
2-anilino-6-chloro-3-(pyridazin-3-yl)quinazolin-4(3H)-one,
2-anilino-6-chloro-3-(pyrazin-2-yl)quinazolin-4(3H)-one,
2-anilino-6-chloro-3-(pyridin-4-yl)quinazolin-4(3H)-one,
2-anilino-6-chloro-3-(pyrimidin-5-yl)quinazolin-4(3H)-one,
2-anilino-6-chloro-3-(5-fluoropyridin-2-yl)quinazolin-4(3H)-one,
2-(2-chloroanilino)-6-fluoro-3-phenylquinazolin-4(3H)-one,
2-anilino-6,8-difluoro-3-phenylquinazolin-4(3H)-one,
6-fluoro-2-[4-(hydroxymethyl)anilino]-3-phenylquinazolin-4 (3H)-one,
6-fluoro-3-phenyl-2-{4-[(piperidin-1-yl)methyl]anilino}quinazolin-4(3H)-one,
6-fluoro-2-{4-[(morpholin-4-yl)methyl]anilino}-3-phenylquinazolin-4(3H)-one,
2-{4-[(azetidin-1-yl)methyl]anilino}-6-fluoro-3-phenylquinazolin-4(3H)-one,
2-(4-{[ethyl(methyl)amino]methyl}anilino)-6-fluoro-3-phenylquinazolin-4(3H)-one,
2-{4-[(diethylamino)methyl]anilino}-6-fluoro-3-phenylquinazolin-4(3H)-one,
6-fluoro-2-(4-{[(2-methoxyethyl)(methyl)amino]methyl}anilino)-3-phenylquinazolin-4(3H)-one,
2-{4-[(3,3-difluoroazetidin-1-yl)methyl]anilino}-6-fluoro-3-phenylquinazolin-4(3H)-one,
2-{4-[(3,3-dimethylazetidin-1-yl)methyl]anilino}-6-fluoro-3-phenylquinazolin-4(3H)-one,
2-anilino-6-(methoxymethyl)-3-phenylquinazolin-4(3H)-one,
2-anilino-6-methoxy-3-phenylquinazolin-4(3H)-one,
2-anilino-6-methyl-3-(pyridin-3-yl)quinazolin-4(3H)-one,
2-{3-[(dimethylamino)methyl]anilino}-3-phenylquinazolin-4(3H)-one,
6-fluoro-2-[3-(hydroxymethyl)anilino]-3-phenylquinazolin-4 (3H)-one,
2-{3-[(azetidin-1-yl)methyl]anilino}-6-fluoro-3-phenylquinazolin-4(3H)-one,
6-ethyl-2-[4-(hydroxymethyl)anilino]-3-phenylquinazolin-4 (3H)-one, and
6-chloro-2-(4-chloroanilino)-3-phenylpyrido[2,3-d]pyrimidin-4(3H)-one.

[Item 23]
A medicament comprising the compound or the pharmaceutically acceptable salt thereof according to any one of items 1 to 22 as an active ingredient.

[Item 24]
The medicament according to item 23, which is a therapeutic drug or a prophylactic drug for epilepsy or amyotrophic lateral sclerosis.

[Item 25]
The medicament according to item 23, which is a therapeutic drug or a prophylactic drug for amyotrophic lateral sclerosis.

[Item 26]
A nerve hyperexcitation suppressing agent comprising the compound or the pharmaceutically acceptable salt thereof according to any one of items 1 to 22 as an active ingredient.

[Item 27]
A pharmaceutical composition comprising the compound or the pharmaceutically acceptable salt thereof according to any one of items 1 to 22.

[Item 28]
The pharmaceutical composition according to item 27, which is a therapeutic drug or a prophylactic drug for epilepsy or amyotrophic lateral sclerosis.

[Item 29]
A method for treating epilepsy or amyotrophic lateral sclerosis, comprising administering a therapeutically effective amount of the compound or the pharmaceutically acceptable salt thereof according to any one of items 1 to 22 to a patient in need thereof.

[Item 30]
Use of the compound or the pharmaceutically acceptable salt thereof according to any one of items 1 to 22 for the manufacture of a therapeutic agent for epilepsy or amyotrophic lateral sclerosis.

[Item 31]
The compound or the pharmaceutically acceptable salt thereof according to any one of items 1 to 22 for use in the treatment of epilepsy or amyotrophic lateral sclerosis.

[Item 32]
A pharmaceutical composition comprised of the compound or the pharmaceutically acceptable salt thereof according to any one of items 1 to 22 in combination with at least one agent selected from agents classified as an antiepileptic drug, an anti-amyotrophic lateral sclerosis drug, an antioxidant, or an anti-inflammatory drug.

[Item 33]
A pharmaceutical composition comprising the compound or the pharmaceutically acceptable salt thereof according to any one of items 1 to 22 for the treatment of epilepsy or amyotrophic lateral sclerosis used concomitantly with at least one agent selected from agents classified as an antiepileptic drug, an anti-amyotrophic lateral sclerosis drug, an antioxidant, or an anti-inflammatory drug.

[Item 34]

A medicament, which is a therapeutic drug or a prophylactic drug for epilepsy or amyotrophic lateral sclerosis, comprising, as an active ingredient, a compound represented by

[Chemical Formula 15]

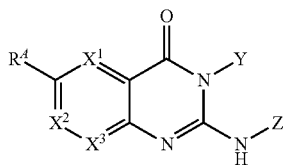
(1)

or a pharmaceutically acceptable salt thereof, wherein,
$X^1$ represents $CR^1$ or N,
$X^2$ represents $CR^2$ or N,
$X^3$ represents $CR^3$ or N,
wherein (1) if $X^1$ is N, then $X^2$ is $CR^2$, and $X^3$ is $CR^3$, (2) if $X^2$ is N, then $X^1$ is $CR^1$, and $X^3$ is $CR^3$, and (3) if $X^3$ is N, then $X^1$ is $CR^1$, and $X^2$ is $CR^2$,
Y represents optionally substituted $C_{6-10}$ aryl or optionally substituted 6- to 10-membered heteroaryl,
Z represents optionally substituted $C_{6-10}$ aryl,
$R^A$ represents a hydrogen atom, halogen, cyano, optionally substituted $C_{1-6}$ alkylsulfonyl, optionally substituted $C_{1-6}$ alkyl, or optionally substituted $C_{1-6}$ alkoxy, and
$R^1$, $R^2$, and $R^3$ each independently represent a hydrogen atom, halogen, optionally substituted $C_{1-6}$ alkyl, or optionally substituted $C_{1-6}$ alkoxy.

[Item 35]

The medicament according to item 34, which is a therapeutic drug or a prophylactic drug for amyotrophic lateral sclerosis.

[Item 36]

A nerve hyperexcitation suppressing agent comprising, as an active ingredient, a compound represented by

[Chemical Formula 16]

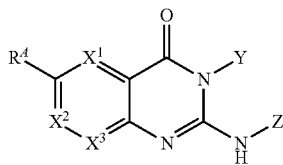
(1)

or a pharmaceutically acceptable salt thereof,
wherein,
$X^1$ represents $CR^1$ or N,
$X^2$ represents $CR^2$ or N,
$X^3$ represents $CR^3$ or N,
wherein (1) if $X^1$ is N, then $X^2$ is $CR^2$, and $X^3$ is $CR^3$, (2) if $X^2$ is N, then $X^1$ is $CR^1$, and $X^3$ is $CR^3$, and (3) if $X^3$ is N, then $X^1$ is $CR^1$, and $X^2$ is $CR^2$,
Y represents optionally substituted $C_{6-10}$ aryl or optionally substituted 6- to 10-membered heteroaryl,
Z represents optionally substituted $C_{6-10}$ aryl,
$R^A$ represents a hydrogen atom, halogen, cyano, optionally substituted $C_{1-6}$ alkylsulfonyl, optionally substituted $C_{1-6}$ alkyl, or optionally substituted $C_{1-6}$ alkoxy, and $R^1$, $R^2$, and $R^3$ each independently represent a hydrogen atom, halogen, optionally substituted $C_{1-6}$ alkyl, or optionally substituted $C_{1-6}$ alkoxy.

[Item 37]

A pharmaceutical composition, which is a therapeutic drug or a prophylactic drug for epilepsy or amyotrophic lateral sclerosis, comprising a compound represented by

[Chemical Formula 17]

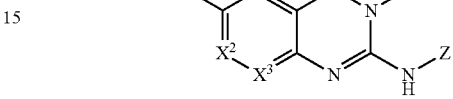
(1)

or a pharmaceutically acceptable salt thereof,
wherein,
$X^1$ represents $CR^1$ or N,
$X^2$ represents $CR^2$ or N,
$X^3$ represents $CR^3$ or N,
wherein (1) if $X^1$ is N, then $X^2$ is $CR^2$, and $X^3$ is $CR^3$, (2) if $X^2$ is N, then $X^1$ is $CR^1$, and $X^3$ is $CR^3$, and (3) if $X^3$ is N, then $X^1$ is $CR^1$, and $X^2$ is $CR^2$,
Y represents optionally substituted $C_{6-10}$ aryl or optionally substituted 6- to 10-membered heteroaryl,
Z represents optionally substituted $C_{6-10}$ aryl,
$R^A$ represents a hydrogen atom, halogen, cyano, optionally substituted $C_{1-6}$ alkylsulfonyl, optionally substituted $C_{1-6}$ alkyl, or optionally substituted $C_{1-6}$ alkoxy, and
$R^1$, $R^2$, and $R^3$ each independently represent a hydrogen atom, halogen, optionally substituted $C_{1-6}$ alkyl, or optionally substituted $C_{1-6}$ alkoxy.

[Item 38]

A method for treating epilepsy or amyotrophic lateral sclerosis, comprising administering, to a patient in need thereof, a therapeutically effective amount of a compound represented by

[Chemical Formula 18]

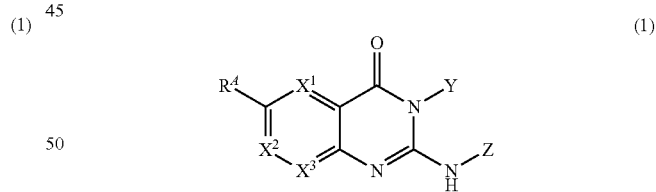
(1)

or a pharmaceutically acceptable salt thereof,
wherein,
$X^1$ represents $CR^1$ or N,
$X^2$ represents $CR^2$ or N,
$X^3$ represents $CR^3$ or N,
wherein (1) if $X^1$ is N, then $X^2$ is $CR^2$, and $X^3$ is $CR^3$, (2) if $X^2$ is N, then $X^1$ is $CR^1$, and $X^3$ is $CR^3$, and (3) if $X^3$ is N, then $X^1$ is $CR^1$, and $X^2$ is $CR^2$,
Y represents optionally substituted $C_{6-10}$ aryl or optionally substituted 6- to 10-membered heteroaryl,
Z represents optionally substituted $C_{6-10}$ aryl,
$R^A$ represents a hydrogen atom, halogen, cyano, optionally substituted $C_{1-6}$ alkylsulfonyl, optionally substituted $C_{1-6}$ alkyl, or optionally substituted $C_{1-6}$ alkoxy, and R$^1$, R$^2$, and R$^3$ each independently represent a hydrogen atom, halogen, optionally substituted C$_{1-6}$ alkyl, or optionally substituted C$_{1-6}$ alkoxy.

[Item 39]

Use of a compound represented by

[Chemical Formula 19]

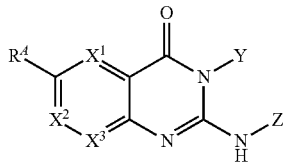

(1)

or a pharmaceutically acceptable salt thereof,
wherein,
X$^1$ represents CR$^1$ or N,
X$^2$ represents CR$^2$ or N,
X$^3$ represents CR$^3$ or N,
wherein (1) if X$^1$ is N, then X$^2$ is CR$^2$, and X$^3$ is CR$^3$, (2) if X$^2$ is N, then X$^1$ is CR$^1$, and X$^3$ is CR$^3$, and (3) if X$^3$ is N, then X$^1$ is CR$^1$, and X$^2$ is CR$^2$,
Y represents optionally substituted C$_{6-10}$ aryl or optionally substituted 6- to 10-membered heteroaryl,
Z represents optionally substituted C$_{6-10}$ aryl,
R$^A$ represents a hydrogen atom, halogen, cyano, optionally substituted C$_{1-6}$ alkylsulfonyl, optionally substituted C$_{1-6}$ alkyl, or optionally substituted C$_{1-6}$ alkoxy, and
R$^1$, R$^2$, and R$^3$ each independently represent a hydrogen atom, halogen, optionally substituted C$_{1-6}$ alkyl, or optionally substituted C$_{1-6}$ alkoxy, for the manufacture of a therapeutic agent for epilepsy or amyotrophic lateral sclerosis.

[Item 40]

A compound represented by

[Chemical Formula 20]

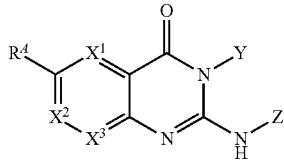

(1)

or a pharmaceutically acceptable salt thereof,
wherein,
X$^1$ represents CR$^1$ or N,
X$^2$ represents CR$^2$ or N,
X$^3$ represents CR$^3$ or N,
wherein (1) if X$^1$ is N, then X$^2$ is CR$^2$, and X$^3$ is CR$^3$, (2) if X$^2$ is N, then X$^1$ is CR$^1$, and X$^3$ is CR$^3$, and (3) if X$^3$ is N, then X$^1$ is CR$^1$, and X$^2$ is CR$^2$,
Y represents optionally substituted C$_{6-10}$ aryl or optionally substituted 6- to 10-membered heteroaryl,
Z represents optionally substituted C$_{6-10}$ aryl,
R$^A$ represents a hydrogen atom, halogen, cyano, optionally substituted C$_{1-6}$ alkylsulfonyl, optionally substituted C$_{1-6}$ alkyl, or optionally substituted C$_{1-6}$ alkoxy, and
R$^1$, R$^2$, and R$^3$ each independently represent a hydrogen atom, halogen, optionally substituted C$_{1-6}$ alkyl, or optionally substituted C$_{1-6}$ alkoxy, for use in the treatment of epilepsy or amyotrophic lateral sclerosis.

[Item 41]

A medicament comprised of a compound represented by

[Chemical Formula 21]

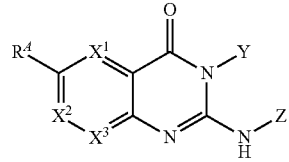

(1)

or a pharmaceutically acceptable salt thereof,
wherein,
X$^1$ represents CR$^1$ or N,
X$^2$ represents CR$^2$ or N,
X$^3$ represents CR$^3$ or N,
wherein (1) if X$^1$ is N, then X$^2$ is CR$^2$, and X$^3$ is CR$^3$, (2) if X$^2$ is N, then X$^1$ is CR$^1$, and X$^3$ is CR$^3$, and (3) if X$^3$ is N, then X$^1$ is CR$^1$, and X$^2$ is CR$^2$,
Y represents optionally substituted C$_{6-10}$ aryl or optionally substituted 6- to 10-membered heteroaryl,
Z represents optionally substituted C$_{6-10}$ aryl,
R$^A$ represents a hydrogen atom, halogen, cyano, optionally substituted C$_{1-6}$ alkylsulfonyl, optionally substituted C$_{1-6}$ alkyl, or optionally substituted C$_{1-6}$ alkoxy, and
R$^1$, R$^2$, and R$^3$ each independently represent a hydrogen atom, halogen, optionally substituted C$_{1-6}$ alkyl, or optionally substituted C$_{1-6}$ alkoxy, in combination with at least one agent selected from agents classified as an antiepileptic drug, an anti-amyotrophic lateral sclerosis drug, an antioxidant, or an anti-inflammatory drug.

[Item 42]

A pharmaceutical composition comprising a compound represented by

[Chemical Formula 22]

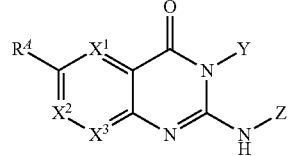

(1)

or a pharmaceutically acceptable salt thereof,
wherein,
X$^1$ represents CR$^1$ or N,
X$^2$ represents CR$^2$ or N, and
X$^3$ represents CR$^3$ or N,
wherein (1) if X$^1$ is N, then X$^2$ is CR$^2$, and X$^3$ is CR$^3$, (2) if X$^2$ is N, then X$^1$ is CR$^1$, and X$^3$ is CR$^3$, and (3) if X$^3$ is N, then X$^1$ is CR$^1$, and X$^2$ is CR$^2$,
Y represents optionally substituted C$_{6-10}$ aryl or optionally substituted 6- to 10-membered heteroaryl,
Z represents optionally substituted C$_{6-10}$ aryl,
R$^A$ represents a hydrogen atom, halogen, cyano, optionally substituted C$_{1-6}$ alkylsulfonyl, optionally substituted C$_{1-6}$ alkyl, or optionally substituted C$_{1-6}$ alkoxy, and
R$^1$, R$^2$, and R$^3$ each independently represent a hydrogen atom, halogen, optionally substituted C$_{1-6}$ alkyl, or optionally substituted C$_{1-6}$ alkoxy, for treating epilepsy or amyotrophic lateral sclerosis in concomitant use with at least one agent selected from agents classified as an antiepileptic drug, an anti-amyotrophic lateral sclerosis drug, an antioxidant, or an anti-inflammatory drug.

The present invention is intended so that one or more of the features described above can be provided not only as the explicitly disclosed combinations, but also as other combinations thereof. Additional embodiments and advantages of the invention are recognized by those skilled in the art by reading and understanding the following detailed description as needed.

Advantageous Effects of Invention

The compound of the invention is useful as a nerve hyperexcitation suppressing agent. The compound of the invention is also useful as a therapeutic drug or a prophylactic drug for epilepsy or amyotrophic lateral sclerosis.

BRIEF DESCRIPTION OF DRAWINGS

FIG. 1 is a diagram showing the effect of suppressing progression in movement disorders of the compound of Example 1 in the Wobbler mice (amyotrophic lateral sclerosis model) of Test Example 4. A motor function test was conducted through a rotarod test. The vertical axis represents the Latency to fall (seconds), and the horizontal axis represents the number of days of treatment (days). The black circles indicate results for a control group (no drug: only medium). The rhombuses are results from administering the compound of Example 1 at a concentration of 0.25 mg/g of feed. The triangles are results from administering the compound of Example 1 at a concentration of 0.5 mg/g of feed. The squares are results from administering the compound of Example 1 at a concentration of 1.0 mg/g of feed. The error bars represent the standard error. * indicates p<0.05, and ** indicates p<0.01.

DESCRIPTION OF EMBODIMENTS

The present invention is described hereinafter in more detail.

The number of substituents in a group defined as "optionally substituted" or "substituted" is not particularly limited herein, as long as a substitution is possible. Moreover, unless indicated otherwise, the description for each group is also applicable when the group is a part of, or a substituent of, another group.

A substituent in "optionally substituted" is selected from substituent group α that consists of the following, and such an optional substitution is made with 1 to 5 of the same or different substituents. While not particularly limited by the type of substituent, if an atom to which the substituent attaches is an oxygen atom, a nitrogen atom, or a sulfur atom, the substituent is limited to the following substituents that attach to a carbon atom.

Substituent group α includes
1) a halogen atom
2) a hydroxyl group
3) a carboxyl group
4) a cyano group
5) a $C_{1-6}$ alkyl group
6) a $C_{2-6}$ alkenyl group
7) a $C_{2-6}$ alkynyl group
8) a $C_{1-6}$ alkoxy group
9) a $C_{1-6}$ alkylthio group
10) a $C_{1-6}$ alkylcarbonyl group
11) a $C_{1-6}$ alkylsulfonyl group (wherein each substituent from 5) to 11) is optionally substituted with 1 to 5 of the same or different substituents selected from substituent group β)
12) a $C_{3-10}$ alicyclic group
13) a $C_{3-10}$ alicyclic oxy group
14) a $C_{6-10}$ aryloxy group
15) a 5- or 6-membered heteroaryloxy group
16) a 4- to 10-membered non-aryl heterocyclyl oxy group
17) a $C_{3-10}$ alicyclic thio group
18) a $C_{6-10}$ arylthio group
19) a 5- or 6-membered heteroarylthio group
20) a 4- to 10-membered non-aryl heterocyclyl thio group
21) $C_{6-10}$ aryl
22) 5- or 6-membered heteroaryl
23) a 4- to 10-membered non-aryl heterocycle
24) a $C_{3-10}$ alicyclic carbonyl group
25) a $C_{6-10}$ arylcarbonyl group
26) a 5- or 6-membered heteroarylcarbonyl group
27) a 4- to 10-membered non-aryl heterocyclyl carbonyl group
28) a $C_{3-10}$ alicyclic sulfonyl group
29) a $C_{6-10}$ arylsulfonyl group
30) a 5- or 6-membered heteroarylsulfonyl group
31) a 4- to 10-membered non-aryl heterocyclyl sulfonyl group
(wherein each substituent from 12) to 31) is optionally substituted with 1 to 5 of substituent group β or 1) a $C_{1-6}$ alkyl group)
32) —$NR^{10a}R^{11a}$
33) —$SO_2$—$NR^{10b}R^{11b}$
34) —$NR^{10c}$—$C(=O)R^{11c}$
35) —$NR^{10d}$—$C(=O)OR^{11d}$
36) —$NR^{12a}$—$C(=O)NR^{10e}R^{11e}$
37) —$NR^{10f}$—$C(=S)R^{11f}$
38) —$NR^{10g}$—$C(=S)OR^{11g}$,
39) —$NR^{12b}$—$C(=S)NR^{10h}R^{11h}$
40) —$NR^{10i}$—$SO_2$—$R^{11i}$
41) —$NR^{12c}$—$SO_2$—$NR^{10j}R^{11j}$
42) —$C(=O)OR^{10k}$
43) —$C(=O)NR^{10l}R^{11k}$
44) —$C(=O)NR^{10m}OR^{11l}$
45) —$C(=O)NR^{12d}$—$NR^{10n}R^{11m}$
46) —$C(=S)OR^{10o}$
47) —$C(=S) NR^{10p}R^{11n}$
48) —$C(=S) NR^{10q}OR^{11o}$
49) —$C(=S)NR^{12e}$—$NR^{10r}R^{11p}$
50) —$C(=NR^{13a})R^{10s}$
51) —$C(=NR^{13b})CHO$
52) —$C(=NR^{13c})NR^{10t}R^{11q}$
53) —$C(=NR^{13d})NR^{12f}$—$NR^{10u}R^{11r}$
54) —$NR^{17c}$—$C(=NR^{13k})R^{17d}$
55) —$NR^{12g}$—$C(=NR^{13e})$—$NR^{10v}R^{11s}$
56) —$NR^{14}$—$C(=NR^{13f})NR^{12h}$—$NR^{10w}R^{11t}$
57) —$OC(=O)R^{10x}$
58) —$OC(=O)OR^{10y}$
59) —$OC(=O)NR^{10z1}R^{11u}$
60) —$NR^{12i}$—$NR^{10z2}R^{11v}$
61) —$NR^{10z3}OR^{11w}$
62) —$C(=N$—$OR^{13a})R^{10s}$
63) —$C(=N$—$OR^{13b})CHO$
64) —$C(=N$—$OR^{13c})NR^{10t}R^{11q}$
65) —$C(=N$—$OR^{13d})NR^{12f}$—$NR^{10u}R^{11r}$ and
66) —$C(=O)H$,
substituent group B is a group consisting of
1) a halogen atom,
2) a hydroxyl group,
3) a carboxyl group, 4) a cyano group,
5) a $C_{3-10}$ alicyclic group,
6) a $C_{1-6}$ alkoxy group,
7) a $C_{3-10}$ alicyclic oxy group,
8) a $C_{1-6}$ alkylthio group,
9) a 5- or 6-membered heteroarylthio group,
10) $C_{6-10}$ aryl,
11) 5- or 6-membered heteroaryl,
12) a 4- to 10-membered non-aryl heterocycle,
13) a $C_{1-6}$ alkylcarbonyl group,
14) a $C_{3-10}$ alicyclic carbonyl group,
15) a $C_{6-10}$ arylcarbonyl group,
16) a 5- or 6-membered heteroarylcarbonyl group,
17) a 4- to 10-membered non-aryl heterocyclyl carbonyl group,
18) —$NR^{15a}R^{16a}$,
19) —$SO_2$—$NR^{15b}R^{16b}$,
20) —$NR^{15c}$—$C(=O)R^{16c}$,
21) —$NR^{17a}$—$C(=O)$ $NR^{15d}R^{16d}$,
22) —$C(=O)$ $NR^{15e}R^{16e}$,
23) —$C(=NR^{13g})R^{15f}$,
24) —$C(=NR^{13h})$ $NR^{15g}R^{16f}$,
25) —$NR^{16g}$—$C(=NR^{13i})R^{15h}$,
26) —$NR^{17b}$—$C(=NR^{13j})$—$NR^{15i}R^{16h}$,
27) —$C(=N$—$OR^{13g})R^{15f}$, and
28) —$C(=N$—$OR^{13h})$ $NR^{15g}R^{16f}$
(wherein each substituent from 5) to 17) in substituent group β is optionally substituted with 1 to 5 substituents selected from the group consisting of a halogen atom, a hydroxyl group, a cyano group, a carboxyl group, and —$NR^{18a}R^{18b}$),
$R^{13a}$, $R^{13b}$, $R^{13c}$, $R^{13d}$, $R^{13e}$, $R^{13f}$, $R^{13g}$, $R^{13h}$, $R^{13i}$, $R^{13j}$ and $R^{13k}$ are the same or different, each independently a hydrogen atom, a hydroxyl group, a $C_{1-6}$ alkyl group, or a $C_{1-6}$ alkoxy group,
$R^{10a}$, $R^{10b}$, $R^{10c}$, $R^{10d}$, $R^{10e}$, $R^{10f}$, $R^{10g}$, $R^{10h}$, $R^{10i}$, $R^{10j}$, $R^{10k}$, $R^{10l}$, $R^{10m}$, $R^{10n}$, $R^{10o}$, $R^{10p}$, $R^{10q}$, $R^{10r}$, $R^{10s}$, $R^{10t}$, $R^{10u}$, $R^{10v}$, $R^{10w}$, $R^{10x}$, $R^{10y}$, $R^{10z1}$, $R^{10z2}$, $R^{10z3}$, $R^{11a}$, $R^{11b}$, $R^{11c}$, $R^{11d}$, $R^{11e}$, $R^{11f}$, $R^{11g}$, $R^{11h}$, $R^{11i}$, $R^{11j}$, $R^{11k}$, $R^{11l}$, $R^{11m}$, $R^{11n}$, $R^{11o}$, $R^{11p}$, $R^{11q}$, $R^{11r}$, $R^{11s}$, $R^{11t}$, $R^{11u}$, $R^{11v}$, $R^{11w}$, $R^{12a}$, $R^{12b}$, $R^{12c}$, $R^{12d}$, $R^{12e}$, $R^{12f}$, $R^{12g}$, $R^{12h}$, $R^{12i}$, $R^{14}$, $R^{15a}$, $R^{15b}$, $R^{15c}$, $R^{15d}$, $R^{15e}$, $R^{15f}$, $R^{15g}$, $R^{15h}$, $R^{15i}$, $R^{16a}$, $R^{16b}$, $R^{16c}$, $R^{16d}$, $R^{16e}$, $R^{16f}$, $R^{16g}$, $R^{16h}$, $R^{17a}$, $R^{17b}$, $R^{17c}$, and $R^{17d}$ are the same or different, each independently a hydrogen atom or a $C_{1-6}$ alkyl group (wherein the alkyl group is optionally substituted with 1 to 3 of the same or different substituents selected from a hydroxyl group, a cyano group, a $C_{1-6}$ alkoxy group, and —$NR^{18a}R^{18b}$), and
$R^{18a}$ and $R^{18b}$ are the same or different, each independently a hydrogen atom or a $C_{1-6}$ alkyl group.
Preferred examples of substituents in "optionally substituted" include the following substituents.
Preferred substituent group α includes
1) a halogen atom
2) a hydroxyl group
3) a carboxyl group
4) a cyano group
5) a $C_{1-6}$ alkyl group
6) a $C_{1-6}$ alkoxy group
7) a $C_{1-6}$ alkylthio group
8) a $C_{1-6}$ alkylcarbonyl group
(wherein each substituent from 5) to 8) is optionally substituted with 1 to 5 of the same or different substituents selected from substituent group β)
9) a $C_{3-10}$ alicyclic group
10) a $C_{3-10}$ alicyclic oxy group
11) a $C_{6-10}$ aryloxy group
12) a 5- or 6-membered heteroaryloxy group
13) a 4- to 10-membered non-aryl heterocyclyl oxy group
14) a $C_{3-10}$ alicyclic thio group
15) a $C_{6-10}$ arylthio group
16) a 5- or 6-membered heteroarylthio group
17) a 4- to 10-membered non-aryl heterocyclyl thio group
18) $C_{6-10}$ aryl
19) 5- or 6-membered heteroaryl
20) a 4- to 10-membered non-aryl heterocycle
21) a $C_{3-10}$ alicyclic carbonyl group
22) a $C_{6-10}$ arylcarbonyl group
23) a 5- or 6-membered heteroarylcarbonyl group
24) a 4- to 10-membered non-aryl heterocyclyl carbonyl group
(wherein each substituent from 9) to 24) is optionally substituted with 1 to 5 of substituent group β or 1) a $C_{1-6}$ alkyl group)
25) —$NR^{10a}R^{11a}$
26) —$SO_2$—$NR^{10b}R^{11b}$
27) —$NR^{10c}$—$C(=O)R^{11c}$
28) —$NR^{12a}$—$C(=O)NR^{10d}R^{11d}$
29) —$NR^{10e}$—$SO_2$—$R^{11e}$
30) —$NR^{12b}$—$SO_2$—$NR^{10f}R^{11f}$
31) —$C(=O)NR^{10g}R^{11g}$
32) —$C(=NR^{11a}R^{10h}$
33) —$C(=NR^{13a})NR^{10i}R^{11h}$
34) —$NR^{11f}$—$C(=NR^{13c})R^{10g}$
35) —$NR^{12c}$—$C(=NR^{13d})$—$NR^{10j}R^{11i}$
36) —$C(=N$—$OR^{13a})R^{10h}$ and
37) —$C(=N$—$OR^{13b})NR^{10i}R^{11h}$
preferred substituent group β is a group consisting of
1) a halogen atom
2) a hydroxyl group
3) a cyano group
4) a $C_{3-10}$ alicyclic group
5) a $C_{1-6}$ alkoxy group
6) a $C_{1-6}$ alkylthio group
7) a 5- or 6-membered heteroarylthio group
8) 5- or 6-membered heteroaryl
9) a 4- to 10-membered non-aryl heterocycle
10) a $C_{1-6}$ alkylcarbonyl group
11) a $C_{3-10}$ alicyclic carbonyl group
12) a $C_{6-10}$ arylcarbonyl group
13) a 5- or 6-membered heteroarylcarbonyl group
14) a 4- to 10-membered non-aryl heterocyclyl carbonyl group
15) —$NR^{15a}R^{16a}$
16) —$NR^{15b}$—$C(=O)R^{16b}$
17) —$NR^{17a}$—$C(=O)NR^{15c}R^{16C}$
18) —$C(=O)NR^{15d}R^{16d}$
19) —$C(=NR^{13e})R^{15e}$
20) —$C(=NR^{13f})$ $NR^{15f}R^{16e}$
21) —$NR^{16f}$—$C(=NR^{13g})R^{15g}$
22) —$NR^{17b}$—$C(=NR^{13h})$—$NR^{15h}R^{16g}$
23) —$C(=N$—$OR^{13e})R^{15e}$ and
24) —$C(=N$—$OR^{13f})$ $NR^{15f}R^{16e}$
(wherein each substituent from 4) to 14) in substituent group β is optionally substituted with 1 to 5 substituents selected from the group consisting of a halogen atom, a hydroxyl group, a cyano group, a carboxyl group, and —$NR^{18a}R^{18b}$),
$R^{13a}$, $R^{13b}$, $R^{13c}$, $R^{13d}$, $R^{13e}$, $R^{13f}$, $R^{13g}$, and $R^{13h}$ are the same or different, each independently a hydrogen atom, a hydroxyl group, a $C_{1-6}$ alkyl group, or a $C_{1-6}$ alkoxy group,
$R^{10a}$, $R^{10b}$, $R^{10c}$, $R^{10d}$, $R^{10e}$, $R^{10f}$, $R^{10g}$, $R^{10h}$, $R^{10i}$, $R^{10j}$, $R^{11a}$, $R^{11b}$, $R^{11c}$, $R^{11d}$, $R^{11e}$, $R^{11f}$, $R^{11g}$, $R^{11h}$, $R^{11i}$, $R^{12a}$, $R^{12b}$, $R^{12c}$, $R^{15a}$, $R^{15b}$, $R^{15c}$, $R^{15d}$, $R^{15e}$, $R^{15f}$, $R^{15g}$, $R^{15h}$, $R^{16a}$, $R^{16b}$, $R^{16c}$, $R^{16d}$, $R^{16e}$, $R^{16f}$, $R^{16g}$, $R^{17a}$, and $R^{17b}$ are the same or different, each independently a hydrogen atom or a $C_{1-6}$ alkyl group (wherein the alkyl group is optionally substituted with 1 to 3 of the same or different substituents selected from a hydroxyl group, a cyano group, a $C_{1-6}$ alkoxy group, and —$NR^{18a}R^{18b}$), and $R^{18a}$ are $R^{18b}$ are the same or different, each independently a hydrogen atom or a $C_{1-6}$ alkyl group.

More preferred examples of substituents in "optionally substituted" include the following substituents.

More preferred substituent group α includes
1) a halogen atom
2) a hydroxyl group
3) a cyano group
4) a $C_{1-6}$ alkyl group
5) a $C_{1-6}$ alkoxy group
6) a $C_{1-6}$ alkylthio group
7) a $C_{1-6}$ alkylcarbonyl group
(wherein each substituent from 4) to 7) is optionally substituted with 1 to 5 of the same or different substituents selected from substituent group β)
8) a 5- or 6-membered heteroaryloxy group
9) a 4- to 10-membered non-aryl heterocyclyl oxy group
10) a 5- or 6-membered heteroarylthio group
11) a 4- to 10-membered non-aryl heterocyclyl thio group
12) $C_{6-10}$ aryl
13) 5- or 6-membered heteroaryl
14) a 4- to 10-membered non-aryl heterocycle
(wherein each substituent from 4) to 14) is optionally substituted with 1 to 5 of substituent group β or 1) a $C_{1-6}$ alkyl group)
15) —$NR^{10a}R^{11a}$
16) —$NR^{11b}$—$C(=O)R^{10b}$
17) —$NR^{12a}$—$C(=O)$ $NR^{10c}R^{11c}$
18) —$C(=O)$ $NR^{10d}R^{11d}$
19) —$C(=NR^{13a})R^{10e}$
20) —$C(=NR^{13b})$ $NR^{10f}R^{11e}$
21) —$NR^{11f}$—$C(=NR^{13c})R^{10g}$
22) —$NR^{12b}$—$C(=NR^{13d})$—$NR^{10h}R^{11g}$
23) —$C(=N$—$OR^{13a})R^{10e}$ and
24) —$C(=N$—$OR^{13b})$ $NR^{10f}R^{11e}$,
substituent group β is more preferably
1) a halogen atom,
2) a hydroxyl group,
3) a cyano group,
4) —$NR^{15a}R^{16a}$,
5) —$NR^{15b}$—$C(=O)R^{16b}$,
6) —$NR^{17a}$—$C(=O)$ $NR^{15c}R^{16c}$,
7) —$C(=O)$ $NR^{15d}R^{16d}$,
8) —$C(=NR^{13e})R^{15e}$,
9) —$C(=NR^{13f})$ $NR^{15f}R^{16e}$,
10) —$NR^{16f}$—$C(=NR^{13g})R^{15g}$,
11) —$NR^{17b}$—$C(=NR^{13h})$—$NR^{15h}R^{16g}$,
12) —$C(=N$—$OR^{13e})R^{15e}$, and
13) —$C(=N$—$OR^{13f})NR^{15f}R^{16e}$, $R^{13a}$, $R^{13b}$, $R^{13c}$, $R^{13d}$, $R^{13e}$, $R^{13f}$, $R^{13g}$, and $R^{13h}$ are the same or different, each independently a hydrogen atom, a hydroxyl group, a $C_{1-6}$ alkyl group, or a $C_{1-6}$ alkoxy group, $R^{10a}$, $R^{10b}$, $R^{10c}$, $R^{10d}$, $R^{10e}$, $R^{10f}$, $R^{10g}$, $R^{10h}$, $R^{11a}$, $R^{11b}$, $R^{11c}$, $R^{11d}$, $R^{11e}$, $R^{11f}$, $R^{11g}$, $R^{12a}$, $R^{12b}$, $R^{15a}$, $R^{15b}$, $R^{15c}$, $R^{15d}$, $R^{15e}$, $R^{15f}$, $R^{15g}$, $R^{15h}$, $R^{16a}$, $R^{16b}$, $R^{16c}$, $R^{16d}$, $R^{16e}$, $R^{16f}$, $R^{16g}$, $R^{17a}$, and $R^{17b}$ are the same or different, each independently a hydrogen atom or a $C_{1-6}$ alkyl group (wherein the alkyl group is optionally substituted with 1 to 3 of the same or different substituents selected from a hydroxyl group, a cyano group, a $C_{1-6}$ alkoxy group, and —$NR^{18a}R^{18b}$), and $R^{18a}$ and $R^{18b}$ are the same or different, each independently a hydrogen atom or a $C_{1-6}$ alkyl group.

"$C_{1-6}$" means that the number of carbon atoms is 1 to 6. The same applies to other numbers. For example, "$C_{1-4}$" means that the number of carbon atoms is 1 to 4.

"Heteroatom" refers to an oxygen atom, a nitrogen atom, a sulfur atom, or the like.

"Halogen atom" refers to a fluorine atom, chlorine atom, bromine atom, or iodine atom, and is preferably a fluorine atom or chlorine atom. A "halogen atom" is also referred to as "halogen".

"$C_{1-6}$ alkyl" or "$C_{1-6}$ alkyl group" refers to a linear or branched saturated hydrocarbon group with 1 to 6 carbon atoms. A $C_{1-6}$ alkyl group is preferably a "$C_{1-4}$ alkyl group", and more preferably a "$C_{1-3}$ alkyl group". Specific examples of "$C_{1-3}$ alkyl group" include methyl, ethyl, propyl, 1-methylethyl, and the like. Specific examples of "$C_{1-4}$ alkyl group" include, in addition to the specific examples specified for the "$C_{1-3}$ alkyl group" described above, butyl, 1,1-dimethylethyl, 1-methylpropyl, 2-methylpropyl, and the like. Specific examples of "$C_{1-6}$ alkyl group" include, in addition to the specific examples specified for the "$C_{1-4}$ alkyl group" described above, pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, hexyl, and the like.

"$C_{2-6}$ alkenyl" or "$C_{2-6}$ alkenyl group" refers to a linear or branched unsaturated hydrocarbon group with 2 to 6 carbon atoms, comprising one or more carbon-carbon double bonds. "$C_{2-6}$ alkenyl group" is preferably a "$C_{2-4}$ alkenyl group". Specific examples of "$C_{2-6}$ alkenyl group" include, but are not limited to, a vinyl group, 1-propylenyl group, 2-propylenyl group, 1-butenyl group, 2-butenyl group, 3-butenyl group, 2-methyl-1-propylenyl group, 2-methyl-2-propylenyl group, and the like.

"$C_{2-6}$ alkynyl" or "$C_{2-6}$ alkynyl group" refers to a linear or branched unsaturated aliphatic hydrocarbon group comprising one or more triple bonds. "$C_{2-6}$ alkynyl group" is preferably a "$C_{2-4}$ alkynyl group". Specific examples thereof include, but are not limited to, an ethynyl group, 1-propynyl group, 2-propynyl group, 1-butynyl group, 1-methyl-2-propynyl group, 3-butynyl group, 1-pentynyl group, 1-hexynyl group, and the like.

"$C_{3-20}$ alicyclic group" refers to a monocyclic or bicyclic non-aromatic hydrocarbon ring group with 3 to 20 carbon atoms, including those with a partially unsaturated bond, those with a partially crosslinked structure, those that have a partially spiro form, and those having one or more carbonyl structures. "Alicyclic group" encompasses cycloalkyl groups, cycloalkenyl groups, and cycloalkynyl groups. "$C_{3-20}$ alicyclic group" is preferably a "$C_{3-10}$ alicyclic group", and more preferably a "$C_{3-7}$ alicyclic group". Specific examples of "$C_{3-7}$ alicyclic group" include cyclopropyl, cyclobutyl, cyclopentyl, cyclohexyl, cycloheptyl, and the like. Specific examples of "$C_{3-10}$ alicyclic group" include, in addition to the specific examples specified for the "$C_{3-7}$ alicyclic group" described above, cycloheptyl, cyclooctyl, cyclononyl, cyclodecyl, adamantyl, and the like.

Specific examples of "$C_{3-20}$ alicyclic group" with a partially crosslinked structure include, but are not limited to, those with a structure shown below and the like.

[Chemical Formula 23]

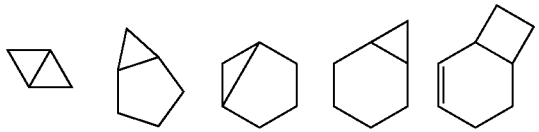

-continued

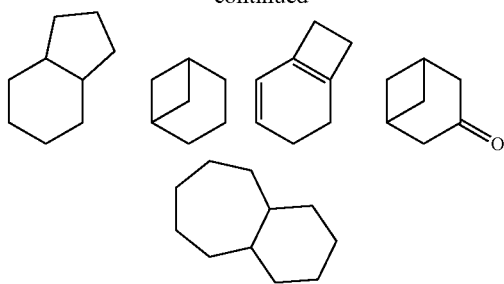

"C$_{3-20}$ alicyclic group" also encompasses compounds fused to an aromatic ring. Specific examples thereof include the groups represented by the following and the like.

[Chemical Formula 24]

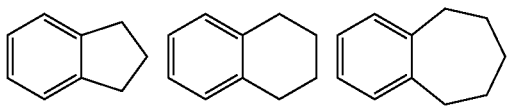

"C$_{3-10}$ alicyclic group" refers to the "C$_{3-20}$ alicyclic group" described above wherein the "C$_{3-10}$ alicyclic group" is a monovalent group.

"C$_{6-10}$ aryl" refers to a monocyclic or bicyclic aromatic hydrocarbon group with 6 to 10 carbon atoms. "C$_{6-10}$ aryl" may be fused to the "alicyclic group" or "non-aryl heterocycle" at any possible position. Specific examples of "C$_{6-10}$ aryl" include phenyl, 1-naphthyl, 2-naphthyl, and the like. Preferred examples of "C$_{6-10}$ aryl" include phenyl. Specific examples of the fused ring structure include the groups represented by the following and the like.

[Chemical Formula 25]

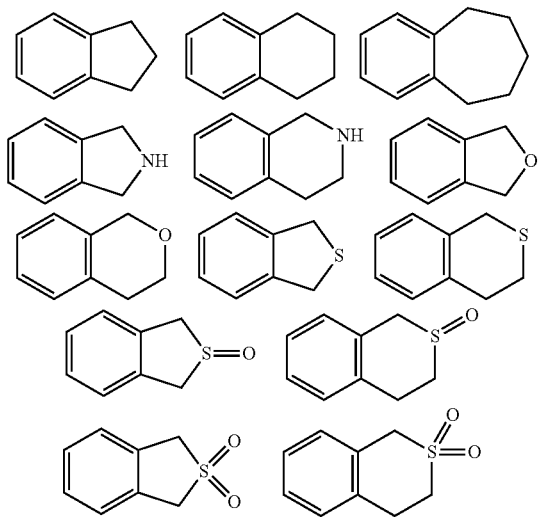

[Chemical Formula 26]

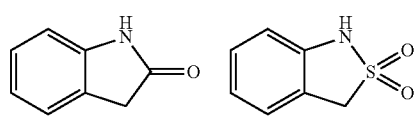

-continued

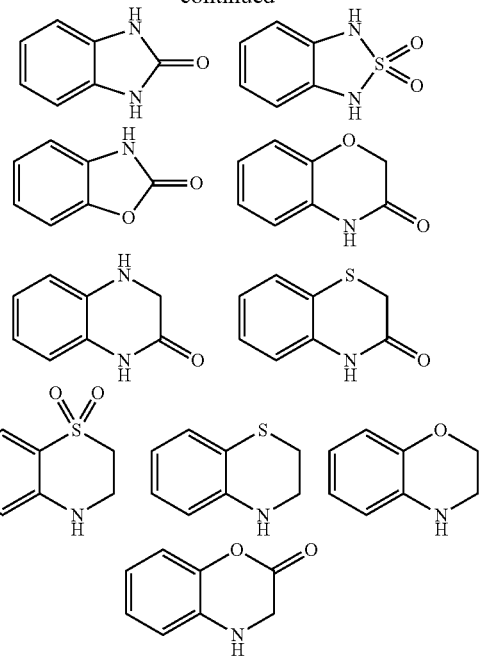

"6- to 10-membered heteroaryl" refers to a monocyclic or bicyclic aromatic heterocyclic group comprised of 6 to 10 atoms, comprising 1 to 4 atoms independently selected from the group consisting of a nitrogen atom, an oxygen atom, and a sulfur atom. "6- to 10-membered heteroaryl" may be fused to the "alicyclic group" or "non-aryl heterocycle" at any possible position. "6- to 10-membered heteroaryl" is preferably "6-membered heteroaryl", more preferably pyridyl, pyrazyl, pyrimidyl, or pyridazinyl, and still more preferably pyridyl or pyrimidyl. Specific examples of "6-membered heteroaryl" include pyridyl, pyrazinyl, pyrimidinyl, and pyridazinyl. Specific examples of "6- to 10-membered heteroaryl" include, in addition to the specific examples specified for the "6-membered heteroaryl" described above, quinoxalyl, triazolopyridyl, and the like.

Specific examples of "9- or 10-membered heteroaryl" include, but are not limited to, compounds with the structures described below and the like.

[Chemical Formula 27]

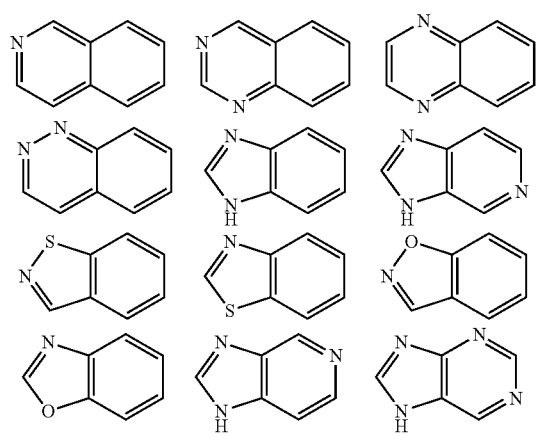

-continued

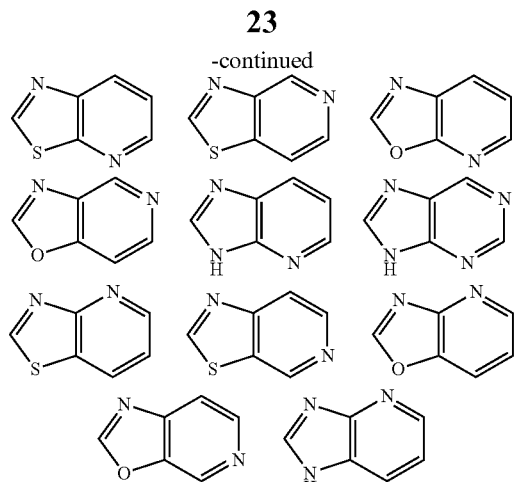

[Chemical Formula 28]

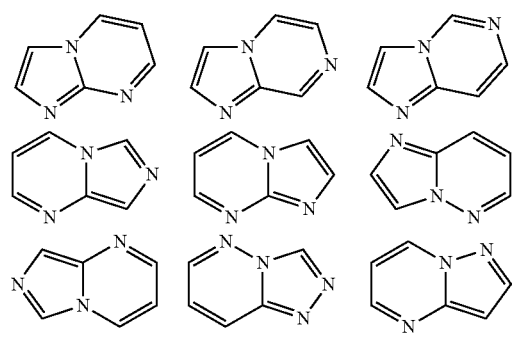

Specific examples of "5-membered heteroaryl" include, but are not limited to, thiophene, pyrrole, thiazole, isothiazole, pyrazole, imidazole, furan, oxazole, isoxazole, oxadiazole, thiadiazole, triazole, tetrazole, and the like. 5-membered heteroaryl is preferably pyrazole, imidazole, oxazole, triazole, tetrazole, or thiadiazole, and more preferably imidazole or thiadiazole.

Specific examples of "5- or 6-membered heteroaryl" include the specific examples for the "5-membered heteroaryl" and "6-membered heteroaryl" described above. The "5- or 6-membered heteroaryl" or "5- to 10-membered heteroaryl" may form a fused ring structure with a $C_{5-10}$ alicyclic group, or a fused ring structure with a 5- to 10-membered non-aryl heterocycle. Specific examples thereof include the groups represented by the following and the like.

[Chemical Formula 29]

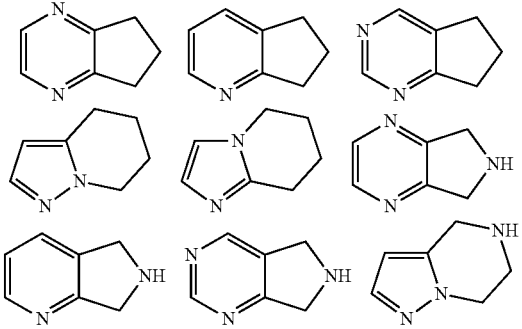

-continued

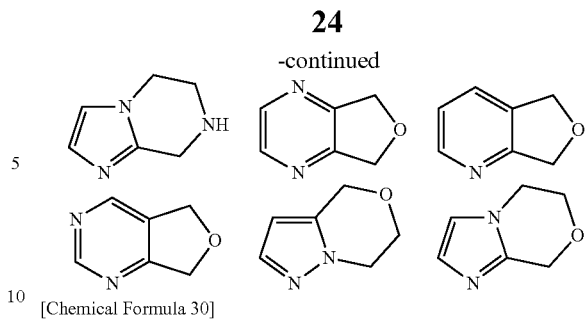

[Chemical Formula 30]

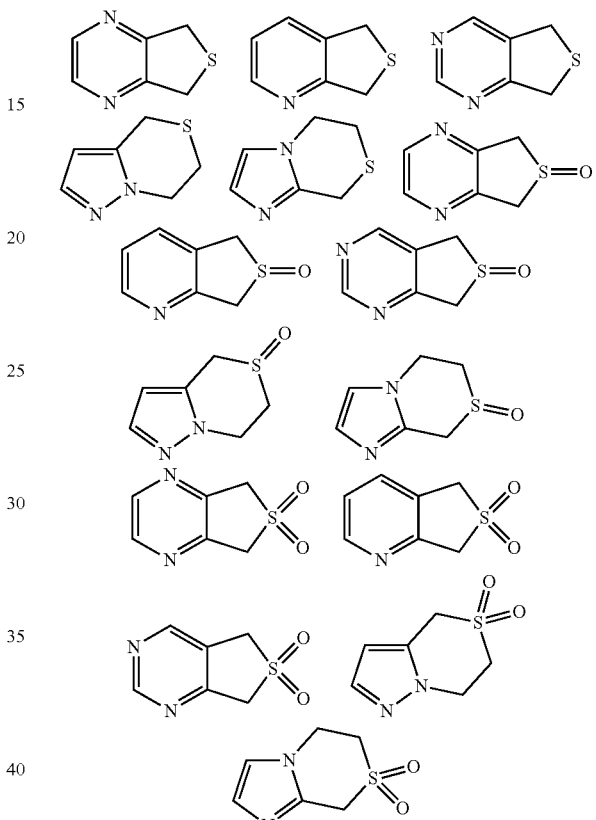

[Chemical Formula 31]

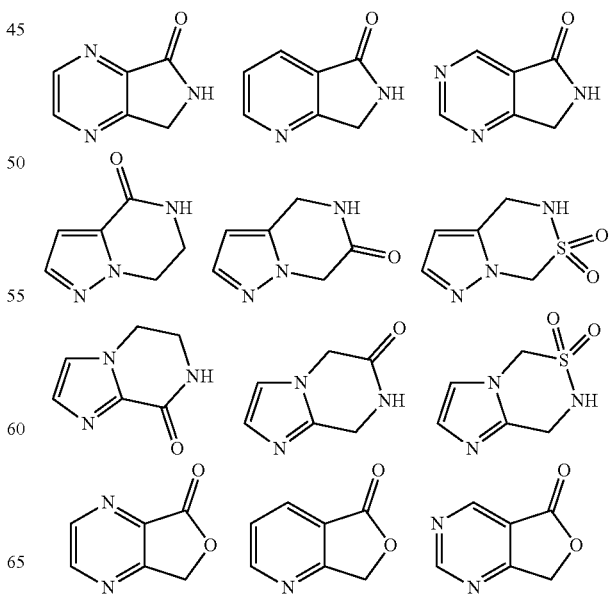

-continued

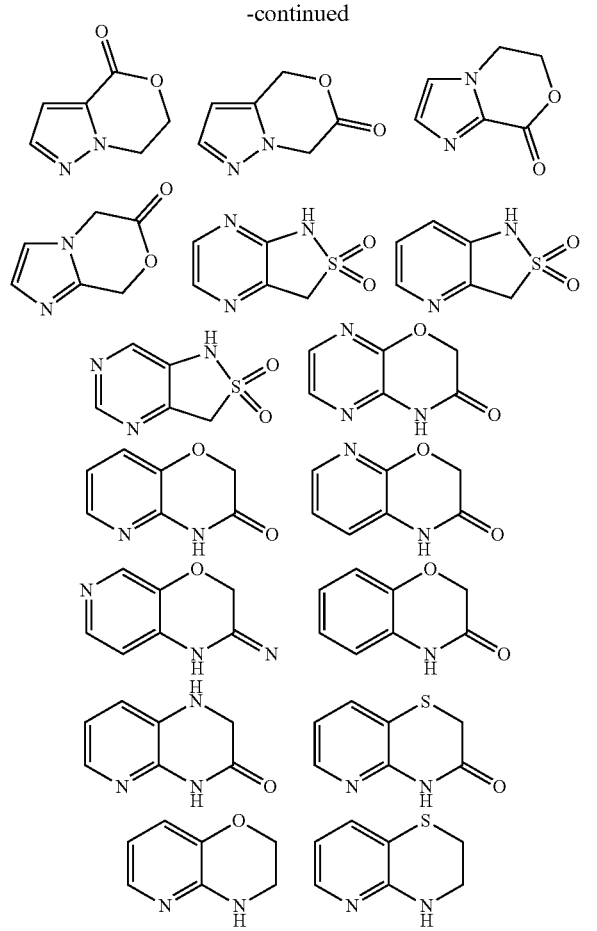

"4- to 20-membered non-aryl heterocyclic group" refers to a monocyclic or bicyclic non-aromatic heterocycle comprised of 4 to 20 atoms, comprising 1 to 2 of the same or different heteroatoms independently selected from the group consisting of a nitrogen atom, an oxygen atom, and a sulfur atom in addition to carbon atoms, including those with a partially unsaturated bond, those with a partially crosslinked structure, and those that have a partially spiro form. "4- to 20-membered non-aryl heterocyclic group" is preferably "4- to 6-membered non-aryl heterocyclic group". Specific examples of "4- to 6-membered non-aryl heterocyclic group" include azetidinyl, pyrrolidinyl, piperidyl, piperazinyl, morpholinyl, tetrahydrofuranyl, tetrahydropyranyl, and the like. In particular, azetidinyl, pyrrolidinyl, piperidyl, morpholinyl, and oxetanyl are preferable. A non-aryl heterocycle may form a fused ring with aryl or heteroaryl. Non-aryl heterocycles also encompass those that are fused with, for example, $C_{6-10}$ aryl or 5- or 6-membered heteroaryl. Further, the non-aryl heterocycle may be comprised by including one or more carbonyl, thiocarbonyl, sulfinyl, or sulfonyl. The non-aryl heterocycles also encompass, for example, lactam, thiolactam, lactone, thiolactone, cyclic imide, cyclic carbamate, cyclic thiocarbamate, and other cyclic groups. In this regard, oxygen atoms of carbonyl, sulfinyl, and sulfonyl and sulfur atoms of thiocarbonyl are not included in the number of 4 to 20 members (size of ring) or in the number of heteroatoms constituting a ring. Specific examples of "4- to 20-membered non-aryl heterocycle" include, but are not limited to, azetidine, pyrrolidine, piperidine, piperazine, morpholine, homopiperidine, oxetane, tetrahydrofuran, tetrahydropyran, heterocycles with the following structure, and the like.

[Chemical Formula 32]

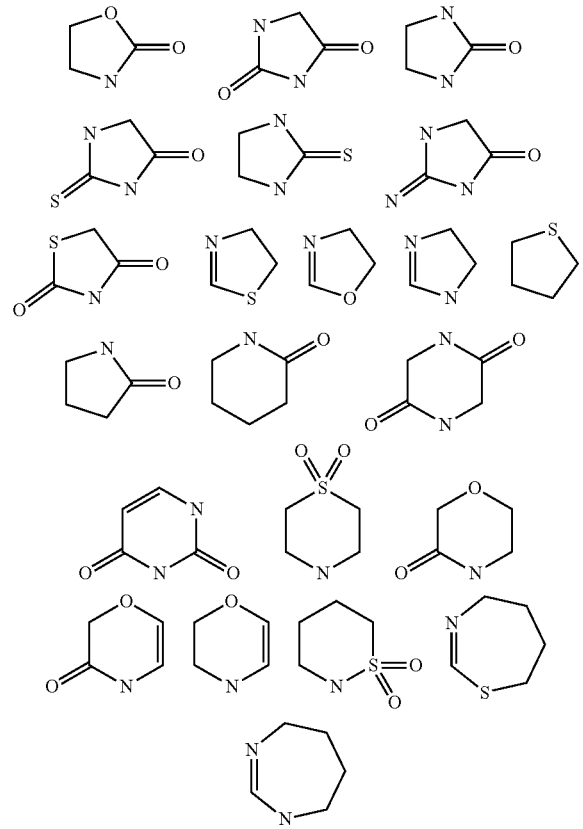

Specific examples of "4- to 20-membered non-aryl heterocycle" with partial crosslinking or spiro structure include, but are not limited to, those with a structure shown below and the like.

[Chemical Formula 33]

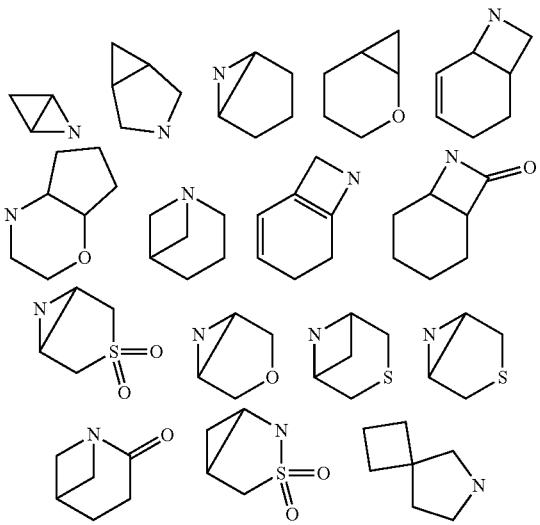

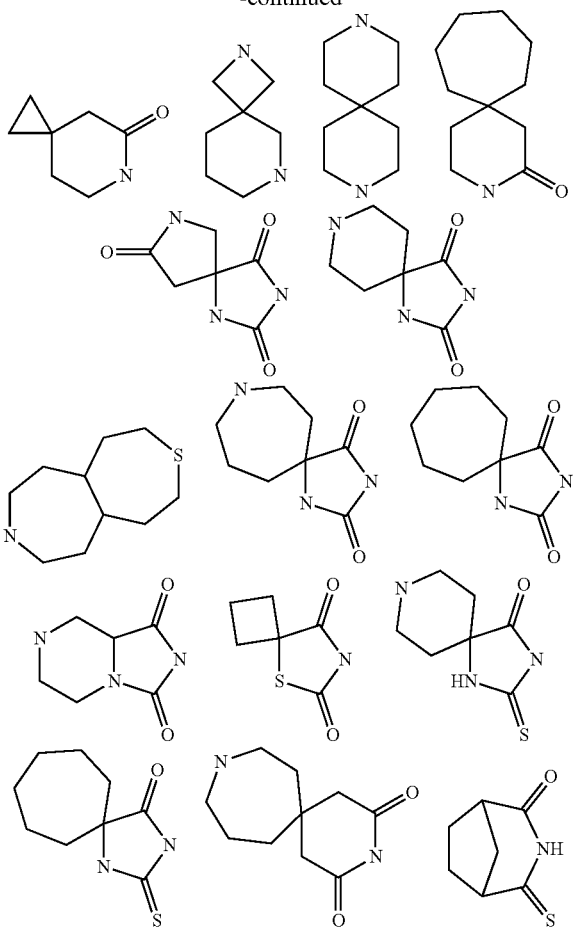

"4- to 20-membered nitrogen-containing non-aryl heterocycle" refers to a monocyclic or bicyclic non-aromatic heterocycle comprised of 4 to 20 atoms, comprising 0 or more of the same or different heteroatoms selected from the group consisting of an oxygen atom, a nitrogen atom, and a sulfur atom, in addition to 1 nitrogen atom, including those with a partially unsaturated bond, those with a partially crosslinked structure, and those that have a partially spiro form. Examples of "4- to 20-membered nitrogen-containing non-aryl heterocycle" include "4- to 10-membered nitrogen-containing non-aryl heterocycle" and "4- to 7-membered nitrogen-containing non-aryl heterocycle".

Specific examples of "4-membered non-aryl heterocycle" having a partially unsaturated bond include, but are not limited to, those with a structure shown below and the like.

[Chemical Formula 34]

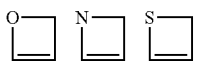

Specific examples of "5-membered non-aryl heterocycle" with a partially unsaturated bond include, but are not limited to, those with a structure shown below and the like.

[Chemical Formula 35]

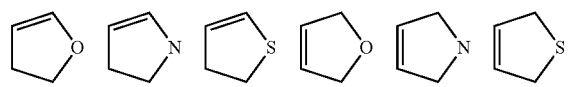

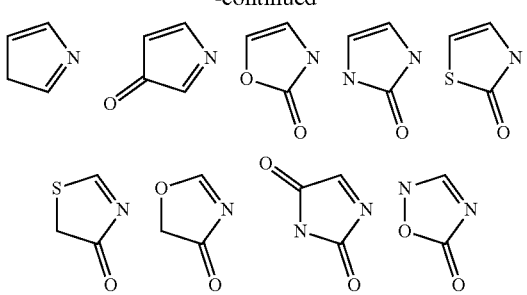

Specific examples of "5-membered non-aryl heterocycle" with a partially crosslinked structure include, but are not limited to, those with a structure shown below and the like.

[Chemical Formula 36]

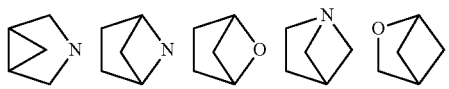

Specific examples of "5-membered non-aryl heterocycle" comprising carbonyl, thiocarbonyl, or the like include, but are not limited to, those with a structure shown below and the like.

[Chemical Formula 37]

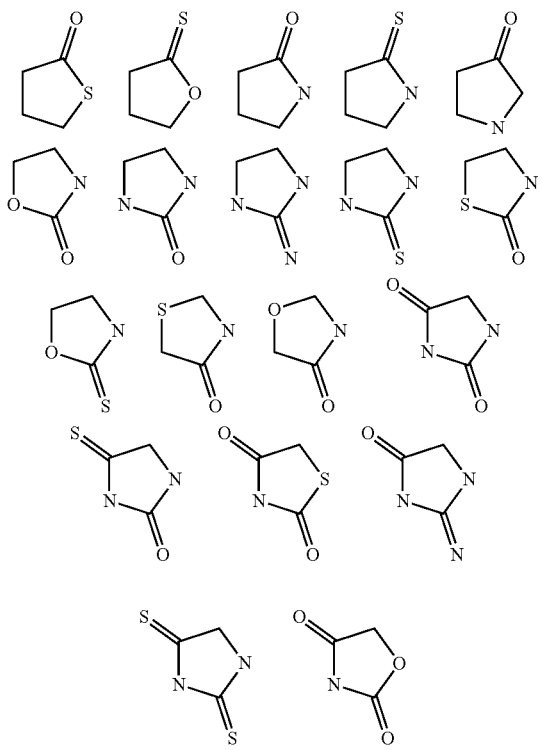

Specific examples of "6-membered non-aryl heterocycle" with a partially unsaturated bond include, but are not limited to, those with a structure shown below and the like.

[Chemical Formula 38]

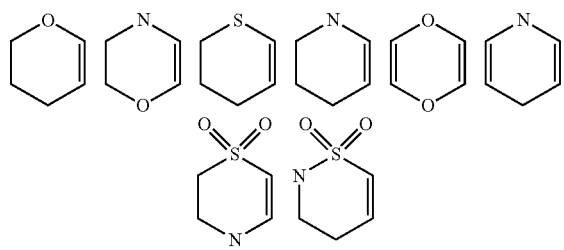

Specific examples of "6-membered non-aryl heterocycle" with a partially crosslinked structure include, but are not limited to, those with a structure shown below and the like.

[Chemical Formula 39]

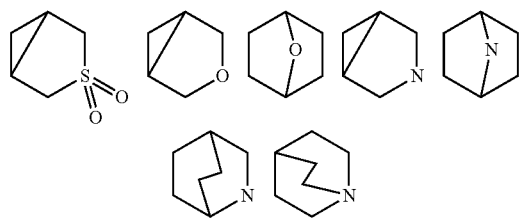

"$C_{1-6}$ alkoxy" or "$C_{1-6}$ alkoxy group" refers to "$C_{1-6}$ alkyloxy", and the "$C_{1-6}$ alkyl" moiety is defined the same as the "$C_{1-6}$ alkyl" described above. "$C_{1-6}$ alkoxy" is preferably "$C_{1-4}$ alkoxy", and more preferably "$C_{1-3}$ alkoxy". Specific examples of "$C_{1-3}$ alkoxy" include methoxy, ethoxy, propoxy, 1-methylethoxy, and the like. Specific examples of "$C_{1-4}$ alkoxy" include, in addition to the specific examples specified for the "$C_{1-3}$ alkoxy" described above, butoxy, 1,1-dimethylethoxy, 1-methylpropoxy, 2-methylpropoxy, and the like. Specific examples of "$C_{1-6}$ alkoxy" include, in addition to the specific examples specified for the "$C_{1-4}$ alkoxy" described above, pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, hexyloxy, and the like.

"$C_{3-6}$ alicyclic oxy" or "$C_{3-6}$ alicyclic oxy group" refers to a ($C_{3-6}$ alicyclic group)-O-group, and the $C_{3-6}$ alicyclic moiety is defined the same as a $C_{3-6}$ alicyclic group. "$C_{3-6}$ alicyclic oxy group" includes "$C_{3-6}$ cycloalkoxy group". "Cycloalkoxy group" refers to "cycloalkyloxy", and the "cycloalkyl" moiety is defined the same as the "cycloalkyl" described above. Specific examples of "$C_{3-6}$ alicyclic oxy group" include a cyclopropoxy group, cyclobutoxy group, cyclopentoxy group, cyclohexoxy group, and the like.

The $C_{6-10}$ aryl moiety of "$C_{6-10}$ aryloxy group" is defined the same as the $C_{6-10}$ aryl described above. "$C_{6-10}$ aryloxy group" is preferably a "$C_6$ or $C_{10}$ aryloxy group". Specific examples of "$C_{6-10}$ aryloxy group" include, but are not limited to, a phenoxy group, 1-naphthyloxy group, 2-naphthyloxy group, and the like.

The 5- or 6-membered heteroaryl moiety of "5- or 6-membered heteroaryloxy group" is defined the same as the "5-membered heteroaryl" or "6-membered heteroaryl" described above. Specific examples of "5- or 6-membered heteroaryloxy group" include, but are not limited to, a pyrazoyloxy group, triazoyloxy group, thiazoyloxy group, thiadiazoyloxy group, pyridyloxy group, pyridazoyloxy group, and the like.

The 4- to 10-membered non-aryl heterocycle moiety of "4- to 10-membered non-aryl heterocyclyl oxy group" is defined the same as the "4- to 10-membered non-aryl heterocycle" described above. "4- to 10-membered non-aryl heterocyclyl oxy group" is preferably a "4- to 6-membered non-aryl heterocyclyl oxy group". Specific examples of "4- to 10-membered non-aryl heterocyclyl oxy group" include, but are not limited to, a tetrahydrofuranyloxy group, tetrahydropyranyloxy group, azetidinyloxy group, pyrrolidinyloxy group, piperidinyloxy group, and the like.

The $C_{1-6}$ alkyl moiety of "$C_{1-6}$ alkylthio group" is defined the same as the $C_{1-6}$ alkyl described above. "$C_{1-6}$ alkylthio group" is preferably a "$C_{1-4}$ alkylthio group", and more preferably a "$C_{1-3}$ alkylthio group". Specific examples of "$C_{1-6}$ alkylthio group" include, but are not limited to, a methylthio group, ethylthio group, propylthio group, butylthio group, isopropylthio group, isobutylthio group, tert-butylthio group, sec-butylthio group, isopentylthio group, neopentylthio group, tert-pentylthio group, 1,2-dimethylpropylthio group, and the like.

"$C_{3-10}$ alicyclic thio" or "$C_{3-10}$ alicyclic thio group" refers to a ($C_{3-10}$ alicyclic group)-S-group, and the $C_{3-10}$ alicyclic moiety is defined the same as the $C_{3-10}$ alicyclic group described above. "$C_{3-10}$ alicyclic thio group" is preferably a "$C_{3-6}$ alicyclic thio group". Specific examples of "$C_{3-6}$ alicyclic thio group" include, but are not limited to, a cyclopropylthio group, cyclobutylthio group, cyclopentylthio group, cyclohexylthio group, and the like.

The $C_{6-10}$ aryl moiety of "$C_{6-10}$ arylthio" or "$C_{6-10}$ arylthio group" is defined the same as the $C_{6-10}$ aryl described above. "$C_{6-10}$ arylthio group" is preferably a "$C_6$ or $C_{10}$ arylthio group". Specific examples of "$C_{6-10}$ arylthio group" include, but are not limited to, a phenylthio group, 1-naphthylthio group, 2-naphthylthio group, and the like.

The 5- or 6-membered heteroaryl moiety of "5- or 6-membered heteroarylthio" or "5- or 6-membered heteroarylthio group" is defined the same as the "5-membered heteroaryl" or "6-membered heteroaryl" described above. Specific examples of "5- or 6-membered heteroarylthio group" include, but are not limited to, a pyrazoylthio group, triazoylthio group, thiazoylthio group, thiadiazoylthio group, pyridylthio group, pyridazoylthio group, and the like.

The 4- to 10-membered non-aryl heterocycle moiety of "4- to 10-membered non-aryl heterocyclyl thio" or "4- to 10-membered non-aryl heterocyclyl thio group" is defined the same as the "4- to 10-membered non-aryl heterocycle" described above. "4- to 10-membered non-aryl heterocyclyl thio group" is preferably a "4- to 6-membered non-aryl heterocyclyl thio group". Specific examples of "4- to 10-membered non-aryl heterocyclyl thio group" include, but are not limited to, a tetrahydropyranylthio group, piperidinylthio group, and the like.

"$C_{1-6}$ alkylcarbonyl" or "$C_{1-6}$ alkylcarbonyl group" refers to a carbonyl group substituted with the "$C_{1-6}$ alkyl group" described above. "$C_{1-6}$ alkylcarbonyl group" is preferably a "$C_{1-4}$ alkylcarbonyl group". Specific examples of "$C_{1-6}$ alkylcarbonyl group" include, but are not limited to, an acetyl group, propionyl group, butyryl group, and the like.

"$C_{3-10}$ alicyclic carbonyl" or "$C_{3-10}$ alicyclic carbonyl group" refers to a carbonyl group substituted with the "$C_{3-10}$ alicyclic group" described above. "$C_{3-10}$ alicyclic carbonyl group" is preferably a "$C_{3-6}$ alicyclic carbonyl group". Specific examples of "$C_{3-10}$ alicyclic carbonyl group" include, but are not limited to, a cyclopropylcarbonyl group, cyclopentylcarbonyl group, and the like.

"$C_{6-10}$ arylcarbonyl" or "$C_{6-10}$ arylcarbonyl group" refers to a carbonyl group substituted with the "$C_{6-10}$ aryl"

described above. "$C_{6-10}$ arylcarbonyl group" is preferably a "$C_6$ or $C_{10}$ arylcarbonyl group". Specific examples of "$C_{6-10}$ arylcarbonyl group" include, but are not limited to, a benzoyl group, 1-naphthylcarbonyl group, 2-naphthylcarbonyl group, and the like.

"5- or 6-membered heteroarylcarbonyl" or "5- or 6-membered heteroarylcarbonyl group" refers to a carbonyl group substituted with the "5- or 6-membered heteroaryl" described above. Specific examples of "5- or 6-membered heteroarylcarbonyl group" include, but are not limited to, a pyrazoylcarbonyl group, triazoylcarbonyl group, thiazoylcarbonyl group, thiadiazoylcarbonyl group, pyridylcarbonyl group, pyridazoylcarbonyl group, and the like.

"4- to 10-membered non-aryl heterocyclyl carbonyl" or "4- to 10-membered non-aryl heterocyclyl carbonyl group" refers to a carbonyl group substituted with the "4- to 10-membered non-aryl heterocycle" described above. "4- to 10-membered non-aryl heterocyclyl carbonyl group" is preferably a "4- to 6-membered non-aryl heterocyclyl carbonyl group". Specific examples of "4- to 10-membered non-aryl heterocyclyl carbonyl group" include, but are not limited to, an azetidinylcarbonyl group, pyrrolidinylcarbonyl group, piperidinylcarbonyl group, morpholinylcarbonyl group, and the like.

"$C_{1-6}$ alkylsulfonyl" or "$C_{1-6}$ alkylsulfonyl group" refers to a sulfonyl group substituted with the "$C_{1-6}$ alkyl group" described above. "$C_{1-6}$ alkylsulfonyl group" is preferably a "$C_{1-4}$ alkylsulfonyl group". Specific examples of "$C_{1-6}$ alkylsulfonyl group" include, but are not limited to, a methylsulfonyl group, propionylsulfonyl group, butyrylsulfonyl group, and the like.

"$C_{3-10}$ alicyclic sulfonyl" or "$C_{3-10}$ alicyclic sulfonyl group" refers to a sulfonyl group substituted with the "$C_{3-10}$ alicyclic group" described above. "$C_{3-10}$ alicyclic sulfonyl group" is preferably a "$C_{3-6}$ alicyclic sulfonyl group". Specific examples of "$C_{3-10}$ alicyclic sulfonyl group" include, but are not limited to, a cyclopropylsulfonyl group, cyclobutylsulfonyl group, cyclopentylsulfonyl group, cyclohexylsulfonyl group, and the like.

"$C_{6-10}$ arylsulfonyl" or "$C_{6-10}$ arylsulfonyl group" refers to a sulfonyl group substituted with the "$C_{6-10}$ aryl" described above. "$C_{6-10}$ arylsulfonyl group" is preferably a "$C_6$ or $C_{10}$ arylsulfonyl group". Specific examples of "$C_{6-10}$ arylsulfonyl group" include, but are not limited to, a phenylsulfonyl group, 1-naphthylsulfonyl group, 2-naphthylsulfonyl group, and the like.

"5- or 6-membered heteroarylsulfonyl" or "5- or 6-membered heteroarylsulfonyl group" refers to a sulfonyl group substituted with the "5- or 6-membered heteroaryl" described above. Specific examples of "5- or 6-membered heteroarylsulfonyl group" include a pyrazoylsulfonyl group, triazoylsulfonyl group, thiazoylsulfonyl group, thiadiazoylsulfonyl group, pyridylsulfonyl group, pyridazoylsulfonyl group, and the like.

Preferred $X^1$, $X^2$, $X^3$, $R^1$, $R^2$, $R^3$, $R^4$, $R^5$, $R^A$, Y, and Z in the compound of the invention represented by formula (1) are the following, but the technical scope of the present invention is not limited to the following scope of the compounds.

Preferred embodiments of $X^1$ include $CR^1$.
Preferred embodiments of $X^2$ includes $CR^2$.
Preferred embodiments of $X^3$ includes $CR^3$.
Preferred embodiments of $R^1$, $R^2$, and $R^3$ include
(1) a hydrogen atom,
(2) halogen,
(3) $C_{1-6}$ alkoxy, and
(4) $C_{1-6}$ alkyl (wherein the alkyl group is optionally substituted with 1 to 3 of the same or different substituents selected from the group consisting of halogen, hydroxy, and $C_{1-6}$ alkoxy).

More preferred embodiments of $R^1$, $R^2$, and $R^3$ include
(1) a hydrogen atom,
(2) fluorine, chloro,
(3) $C_{1-3}$ alkoxy, and
(4) $C_{1-6}$ alkyl.

Still more preferred embodiments of $R^1$, $R^2$, and $R^3$ include
(1) a hydrogen atom, and
(2) fluorine or chloro.

The most preferred embodiments of $R^1$, $R^2$, and $R^3$ include a hydrogen atom.

Preferred embodiments of $R^4$ include
(1) a hydrogen atom,
(2) halogen,
(3) cyano,
(4) $C_{1-6}$ alkoxy, and
(5) $C_{1-6}$ alkyl (wherein the alkyl group is optionally substituted with 1 to 3 of the same or different substituents selected from the group consisting of halogen, hydroxy, and $C_{1-6}$ alkoxy).

More preferred embodiments of $R^4$ include
(1) a hydrogen atom,
(2) fluorine, chloro
(3) $C_{1-3}$ alkoxy, and
(4) $C_{1-3}$ alkyl.

The most preferred embodiments of $R^4$ include fluorine and chloro.

Preferred embodiments of Y include
(1) $C_{6-10}$ aryl optionally substituted with 1 to 5 of the same or different substituents selected from the group consisting of halogen, cyano, $C_{1-6}$ alkoxy, and $C_{1-6}$ alkyl (wherein the alkoxy group and the alkyl group are optionally substituted with 1 to 3 of the same or different substituents selected from the group consisting of halogen, hydroxy, and $C_{1-6}$ alkoxy), and
(2) 6- to 10-membered heteroaryl optionally substituted with 1 to 5 of the same or different substituents selected from the group consisting of halogen, cyano, $C_{1-6}$ alkoxy, and $C_{1-6}$ alkyl (wherein the alkoxy group and the alkyl group are optionally substituted with 1 to 3 of the same or different substituents selected from the group consisting of halogen, hydroxy, and $C_{1-6}$ alkoxy).

More preferred embodiments of Y include
(1) phenyl optionally substituted with 1 to 5 of the same or different substituents selected from the group consisting of halogen, cyano, $C_{1-3}$ alkoxy, and $C_{1-3}$ alkyl (wherein the alkoxy group and the alkyl group are optionally substituted with 1 to 3 of the same or different substituents selected from the group consisting of halogen and hydroxy), and
(2) 6-membered heteroaryl optionally substituted with 1 to 5 of the same or different substituents selected from the group consisting of halogen, cyano, $C_{1-3}$ alkoxy, and $C_{1-3}$ alkyl (wherein the alkoxy group and the alkyl group are optionally substituted with 1 to 3 fluorine).

Still more preferred embodiments of Y include
(1) phenyl optionally substituted with 1 to 3 of the same or different substituents selected from the group consisting of fluorine, chloro, cyano, methoxy, methyl, and —$CH_2OH$, and (2) 6-membered unsubstituted heteroaryl.

The most preferred embodiments of Y include unsubstituted phenyl.

Preferred embodiments of Z include $C_{6-10}$ aryl optionally substituted with 1 to 5 of the same or different substituents selected from the group consisting of halogen, cyano, $C_{1-6}$ alkoxy, methanesulfonyl, dimethylamino, methyl ester, —$CONH_2$, and $C_{1-6}$ alkyl (wherein the alkoxy group, the methanesulfonyl group, the dimethylamino group, the methyl ester group, and the alkyl group are optionally substituted with 1 to 3 of the same or different substituents selected from the group consisting of halogen, hydroxy, $C_{1-6}$ alkoxy, and —$NR^4R^5$).

More preferred embodiments of Z include phenyl optionally substituted with 1 to 2 of the same or different substituents selected from the group consisting of fluorine, chloro, cyano, $C_{1-6}$ alkoxy, methanesulfonyl, dimethylamino, and $C_{1-6}$ alkyl (wherein the alkoxy group, the methanesulfonyl group, the dimethylamino group, and the alkyl group are optionally substituted with 1 to 3 of the same or different substituents selected from the group consisting of fluorine, hydroxy, $C_{1-6}$ alkoxy, and —$NR^4R^5$).

Still more preferred embodiments of Z include phenyl optionally substituted with 1 to 2 of the same or different substituents selected from the group consisting of fluorine, chloro, cyano, methoxy, $C_{1-3}$ alkyl, —$CH_2OH$, and —$CH_2NR^4R^5$.

Preferred embodiments of $R^4$ and $R^5$ include
(1) a hydrogen atom,
(2) $C_{3-6}$ cycloalkyl, and
(3) $C_{1-6}$ alkyl (wherein the alkyl group is optionally substituted with 1 to 3 of the same or different substituents selected from the group consisting of halogen, hydroxy, $C_{3-8}$ cycloalkyl, $C_{1-6}$ alkoxy, $C_{3-6}$ cycloalkoxy, and 4- to 6-membered non-aryl heterocyclic group).

More preferred embodiments of $R^4$ and $R^5$ include $C_{1-6}$ alkyl (wherein the alkyl group is optionally substituted with 1 to 3 of the same or different substituents selected from the group consisting of halogen, hydroxy, $C_{3-8}$ cycloalkyl, $C_{1-6}$ alkoxy, $C_{3-6}$ cycloalkoxy, and 4- to 6-membered non-aryl heterocyclic group).

Preferred embodiments of —$NR^4R^5$ include formulas (AM-1), (AM-2), (AM-3), (AM-4), (AM-5), (AM-6), (AM-7), (AM-8) (AM-9), (AM-10), (AM-11), (AM-12), (AM-13), (AM-14), (AM-15), (AM-16), and (AM-17).

[Chemical Formula 40]

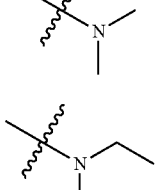
(AM-1)

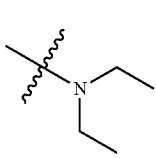
(AM-2)

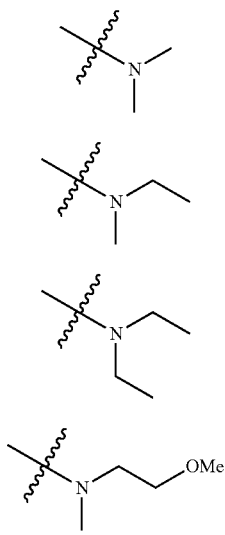
(AM-3)

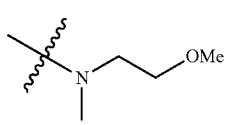
(AM-4)

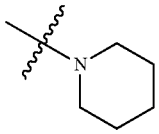
(AM-5)

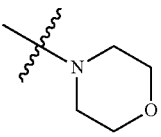
(AM-6)

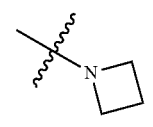
(AM-7)

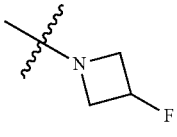
(AM-8)

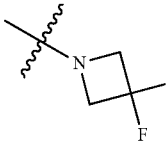
(AM-9)

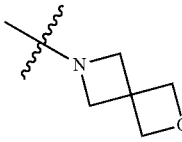
(AM-10)

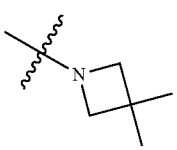
(AM-11)

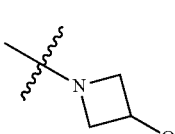
(AM-12)

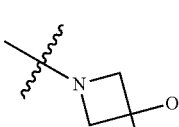
(AM-13)

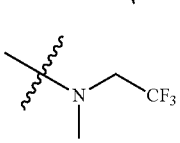
(AM-14)

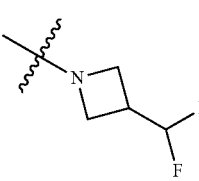
(AM-15)

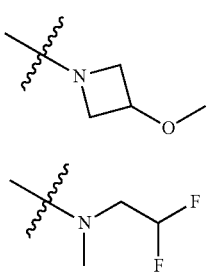

(AM-16)

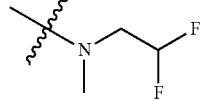

(AM-17)

More preferred embodiments of —NR⁴R⁵ include formulas (AM-1), (AM-2), (AM-4), (AM-6), (AM-7), (AM-8), (AM-9), and (AM-10).

Still more preferred embodiments of —NR⁴R⁵ include formulas (AM-1), (AM-7), (AM-8), (AM-9), and (AM-10).

An embodiment of the compound represented by formula (1) includes the following (A).

(A)

A compound or a pharmaceutically acceptable salt thereof, wherein
$X^1$ is $CR^1$ or N,
$X^2$ is $CR^2$ or N,
$X^3$ is $CR^3$ or N,
wherein (1) if $X^1$ is N, then $X^2$ is $CR^2$, and $X^3$ is $CR^3$, (2) if $X^2$ is N, then $X^1$ is $CR^1$, and $X^3$ is $CR^3$, and (3) if $X^3$ is N, then $X^1$ is $CR^1$, and $X^2$ is $CR^2$
$R^1$, $R^2$, and $R^3$ are each independently
(1) a hydrogen atom,
(2) halogen,
(3) $C_{1-6}$ alkoxy, or
(4) $C_{1-6}$ alkyl (wherein the alkyl group is optionally substituted with 1 to 3 of the same or different substituents selected from the group consisting of halogen, hydroxy, and $C_{1-6}$ alkoxy),
$R^A$ is a hydrogen atom, halogen, $C_{1-6}$ alkoxy, or $C_{1-6}$ alkyl (optionally substituted with 1 to 3 of the same or different substituents selected from the group consisting of halogen and $C_{1-6}$ alkoxy),
Y is
(1) $C_{6-10}$ aryl optionally substituted with 1 to 5 of the same or different substituents selected from the group consisting of halogen, cyano, $C_{1-6}$ alkoxy, methanesulfonyl, dimethylamino, and $C_{1-6}$ alkyl (wherein the alkoxy group, the methanesulfonyl group, the dimethylamino group, and the alkyl group are optionally substituted with 1 to 3 of the same or different substituents selected from the group consisting of halogen, hydroxy, and $C_{1-6}$ alkoxy), or
(2) 6- to 10-membered heteroaryl optionally substituted with 1 to 5 of the same or different substituents selected from the group consisting of halogen, cyano, $C_{1-6}$ alkoxy, methanesulfonyl, dimethylamino, and $C_{1-6}$ alkyl (wherein the alkoxy group, the methanesulfonyl group, the dimethylamino group, and the alkyl group are optionally substituted with 1 to 3 of the same or different substituents selected from the group consisting of halogen, hydroxy, and $C_{1-6}$ alkoxy),
Z is $C_{6-10}$ aryl optionally substituted with 1 to 5 of the same or different substituents selected from the group consisting of halogen, cyano, $C_{1-6}$ alkoxy, methanesulfonyl, dimethylamino, $C_{1-6}$ alkyl ester, —CONH₂, and $C_{1-6}$ alkyl (wherein the alkoxy group, the methanesulfonyl group, the dimethylamino group, the alkyl ester group, and the alkyl group are optionally substituted with 1 to 3 of the same or different substituents selected from the group consisting of halogen, hydroxy, $C_{1-6}$ alkoxy, and —NR⁴R⁵)
$R^4$ and $R^5$ are each independently, and if there are a plurality of instances of $R^4$ and $R^5$, they are also independently
(1) a hydrogen atom,
(2) $C_{3-6}$ cycloalkyl, or
(3) $C_{1-6}$ alkyl (wherein the alkyl group is optionally substituted with 1 to 3 of the same or different substituents selected from the group consisting of halogen, hydroxy, $C_{3-8}$ cycloalkyl, $C_{1-6}$ alkoxy, $C_{3-6}$ cycloalkoxy, and a 4- to 6-membered non-aryl heterocyclic group), wherein $R^4$ and $R^5$, together with the nitrogen atom to which they are attached, may form a 4- to 10-membered nitrogen-containing non-aryl heterocycle (wherein the nitrogen-containing non-aryl heterocycle is optionally substituted with 1 to 5 of the same or different substituents selected from the group consisting of halogen, hydroxy, $C_{1-6}$ alkyl, and $C_{1-6}$ alkoxy).

An embodiment of the compound represented by formula (1) include the following (B).

(B)

A compound or a pharmaceutically acceptable salt thereof, wherein
$X^1$ is $CR^1$,
$X^2$ is $CR^2$
$X^3$ is $CR^3$,
$R^1$, $R^2$, and $R^3$ are each independently
(1) a hydrogen atom,
(2) halogen,
(3) $C_{1-6}$ alkoxy, or
(4) $C_{1-6}$ alkyl (wherein the alkyl group is optionally substituted with 1 to 3 of the same or different substituents selected from the group consisting of halogen, hydroxy, and $C_{1-6}$ alkoxy),
$R^A$ is a hydrogen atom, fluorine, chloro, $C_{1-6}$ alkoxy, or $C_{1-6}$ alkyl (wherein the alkoxy group and the alkyl group are optionally substituted with 1 to 3 fluorine or methoxy),
Y is
(1) phenyl optionally substituted with 1 to 5 of the same or different substituents selected from the group consisting of halogen, cyano, $C_{1-6}$ alkoxy, methanesulfonyl, dimethylamino, and $C_{1-6}$ alkyl (wherein the alkoxy group, the methanesulfonyl group, the dimethylamino group, and the alkyl group are optionally substituted with 1 to 3 of the same or different substituents selected from the group consisting of halogen and hydroxy), or
(2) 6-membered heteroaryl optionally substituted with 1 to 5 of the same or different substituents selected from the group consisting of halogen, cyano, $C_{1-6}$ alkoxy, and $C_{1-6}$ alkyl (wherein the alkoxy group and the alkyl group are optionally substituted with 1 to 3 fluorine),
Z is phenyl optionally substituted with 1 to 2 of the same or different substituents selected from the group consisting of fluorine, chloro, cyano, $C_{1-6}$ alkoxy, methanesulfonyl, dimethylamino, methyl ester, —CONH₂, and $C_{1-6}$ alkyl (wherein the alkoxy group, the methanesulfonyl group, the dimethylamino group, the methyl ester group, and the alkyl group are optionally substituted with 1 to 3 of the same or different substituents selected from the group consisting of fluorine, hydroxy, $C_{1-6}$ alkoxy, and —NR⁴R⁵ and
$R^4$ and $R^5$ are each independently, and if there are a plurality of instances of $R^4$ and $R^3$, they are also independently $C_{1-6}$ alkyl (wherein the alkyl group is optionally substituted with 1 to 3 of the same or different substituents selected from the group consisting of halogen, hydroxy, $C_{3-8}$ cycloalkyl, $C_{1-6}$ alkoxy, $C_{3-6}$ cycloalkoxy, and 4- to 6-membered non-aryl heterocyclic group), wherein $R^4$ and $R^5$, together with the nitrogen atom to which they are attached, may form a 4- to 10-membered nitrogen-containing non-aryl heterocycle.

An embodiment of the compound represented by formula (1) include the following (C).

(C)

A compound or a pharmaceutically acceptable salt thereof, wherein
$X^1$ is $CR^1$,
$X^2$ is $CR^2$
$X^3$ is $CR^3$,
$R^1$, $R^2$, and $R^3$ are each independently
(1) a hydrogen atom,
(2) fluorine, or chloro,
$R^4$ is fluorine or chloro,
Y is
(1) phenyl optionally substituted with 1 to 3 of the same or different substituents selected from the group consisting of fluorine, chloro, cyano, methoxy, methyl, and —CH$_2$OH, or
(2) 6-membered unsubstituted heteroaryl,
Z is phenyl optionally substituted with 1 to 2 of the same or different substituents selected from the group consisting of fluorine, chloro, cyano, $C_{1-6}$ alkoxy, $C_{1-6}$ alkyl, —CH$_2$OH, and —CH$_2$NR$^4$R$^5$, and
$R^4$ and $R^5$ are each independently, and if there are a plurality of instances of $R^4$ and $R^5$, they are also independently $C_{1-6}$ alkyl (wherein the alkyl group is optionally substituted with 1 to 3 of the same or different substituents selected from the group consisting of halogen, hydroxy, $C_{3-8}$ cycloalkyl, $C_{1-6}$ alkoxy, $C_{3-6}$ cycloalkoxy, and 4- to 6-membered non-aryl heterocyclic group), wherein $R^4$ and $R^5$, together with the nitrogen atom to which they are attached, may form a 4- to 10-membered nitrogen-containing non-aryl heterocycle.

An embodiment of the compound represented by formula (1) include the following (D).

(D)

A compound or a pharmaceutically acceptable salt thereof, wherein
$X^1$ is $CR^1$,
$X^2$ is $CR^2$,
$X^3$ is $CR^3$,
$R^1$, $R^2$, and $R^3$ are all hydrogen atoms,
$R^4$ is fluorine or chloro,
Y is unsubstituted phenyl, unsubstituted pyridine, or unsubstituted pyrimidine,
Z is phenyl optionally substituted with 1 to 2 of the same or different substituents selected from the group consisting of fluorine, chloro, cyano, $C_{1-6}$ alkoxy, $C_{1-6}$ alkyl, —CH$_2$OH, and —CH$_2$NR$^4$R$^5$, and
—NR$^4$R$^5$ is, and if there are a plurality of instances, they are each independently formula (AM-1), (AM-2), (AM-3), (AM-4), (AM-5), (AM-6), (AM-7), (AM-8), (AM-9), (AM-10) (AM-11), (AM-12), (AM-13), (AM-14), (AM-15), (AM-16), or (AM-17):

[Chemical Formula 41]

(AM-1)

(AM-2)
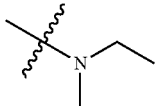

(AM-3)
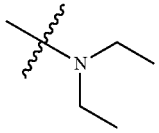

(AM-4)
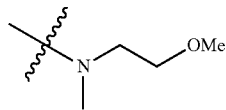

(AM-5)
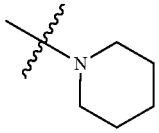

(AM-6)
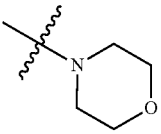

(AM-7)
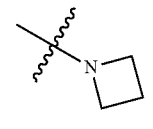

(AM-8)
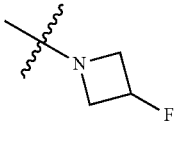

(AM-9)
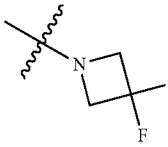

(AM-10)
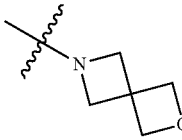

(AM-11)
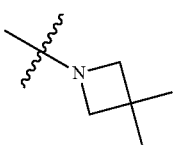

(AM-12)
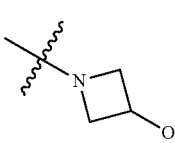

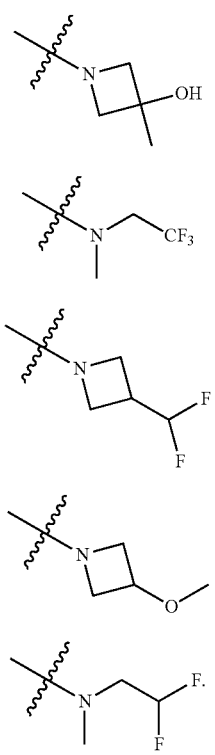

(AM-13)
(AM-14)
(AM-15)
(AM-16)
(AM-17)

Examples of "pharmaceutically acceptable salt" include acid addition salts and base addition salts. Examples of acid addition salts include inorganic acid salts such as hydrochloric acid salt, hydrobromic acid salt, sulfuric acid salt, hydroiodic acid salt, nitric acid salt, and phosphoric acid salt, and organic acid salts such as citric acid salt, oxalic acid salt, phthalic acid salt, fumaric acid salt, maleic acid salt, succinic acid salt, malic acid salt, acetic acid salt, formic acid salt, propionic acid salt, benzoic acid salt, trifluoroacetic acid salt, methanesulfonic acid salt, benzenesulfonic acid salt, para-toluenesulfonic acid salt, and camphorsulfonic acid salt. Examples of base addition salts include inorganic base salts such as sodium salt, potassium salt, calcium salt, magnesium salt, barium salt, and aluminum salt, organic base salts such as trimethylamine, triethylamine, pyridine, picoline, 2,6-lutidine, ethanolamine, diethanolamine, triethanolamine, tromethamine [tris(hydroxymethyl)methylamine], tert-butylamine, cyclohexylamine, dicyclohexylamine, and N—N-dibenzylethylamine, and the like. Furthermore, examples of "pharmaceutically acceptable salt" include amino acid salts of an acidic amino acid or basic amino acid such as arginine, lysine, ornithine, aspartic acid, and glutamic acid.

Salts that are preferable for a raw material compound and intermediate and salts that are acceptable as a raw material of a pharmaceutical product are conventionally used nontoxic salts. Such salts can be acid addition salts such as organic acid salts (e.g., acetic acid salt, trifluoroacetic acid salt, maleic acid salt, furamic acid salt, citric acid salt, tartaric acid salt, methanesulfonic acid salt, benzenesulfonic acid salt, formic acid salt, p-toluenesulfonic acid salt, etc.) and inorganic acid salts (e.g., hydrochloric acid salt, hydrobromic acid salt, hydroiodic acid salt, sulfuric acid salt, nitric acid salt, phosphoric acid salt, etc.), salts of amino acid (e.g., arginine, asparaginic acid, glutamic acid, etc.), metal salts such as alkali metal salts (e.g., sodium salt, potassium salt, etc.) and alkali earth metal salts (e.g., calcium salt, magnesium salt, etc.), ammonium salts, organic base salts (e.g., trimethylamine salt, triethylamine salt, pyridine salt, picoline salt, dicyclohexylamine salt, N,N'-dibenzylethylenediamine salt, etc.), and the like. Those skilled in the art can also appropriately select other salts.

When it is desirable to obtain a salt of the compound of the invention, the compound of the invention can be directly purified if the compound is obtained in a form of a salt, and if the compound is obtained in a free form, the compound can be dissolved or suspended in a suitable organic solvent, and an acid or base is added to form a salt by a conventional method.

Deuterated compounds prepared by converting any one or more of 1H of a compound represented by formula (1) to 2H(D) are also encompassed by the compound represented by formula (1) in the present invention.

The present invention encompasses the compound represented by formula (1) and a pharmaceutically acceptable salt thereof. The compound of the invention can also be in a form of a hydrate and/or solvate of various solvents (ethanolate, etc.) Thus, such hydrates and/or solvates are also encompassed by the compound of the invention. Furthermore, the present invention also encompasses any tautomer, any existing stereoisomer, and crystalline forms in any form of the compound (1) of the invention, and mixtures thereof.

Some of the compounds (1) of the invention can be enantiomers based on an optically-active center, atropisomers based on axial or planar chirality resulting from restriction of intramolecular rotation, other stereoisomers, tautomers, geometric isomers, and the like. Meanwhile, all possible isomers and mixtures thereof, including the isomers mentioned, are encompassed within the scope of the present invention.

In particular, an enantiomer and an atropisomer can be obtained as a racemate and an optically-active form if an optically-active starting material or intermediate is used, respectively. If necessary, a corresponding starting material, intermediate, or final product racemate can be physically or chemically resolved, during an appropriate step of the manufacturing method described below, into their optical enantiomers by a known separation method, such as a method using an optically active column or a fractional crystallization method. Specifically, a diastereomer method, for example, forms two types of diastereomers from a racemate by a reaction using an optical active resolving agent. Since the different diastereomers generally have different physical properties, they can be resolved by a known method such as fractional crystallization.

While manufacturing methods of the compound of the invention are described below, the manufacturing method of the compound of the invention is not limited thereto.

The compound of the invention can be manufactured by, for example, the manufacturing methods described below, but the method is not limited thereto. Such manufacturing methods can be appropriately modified based on the knowledge of those skilled in the art of organic synthetic chemistry. For the compounds used as a raw material, the salts thereof can also be used in the following manufacturing methods, as long as the reaction is not affected.

In the manufacturing methods described below, even if use of a protecting group is not specifically described, a functional group other than those at the reaction point can be protected as needed and deprotected after the completion of a reaction or after a series of reactions to obtain a compound of interest if one of the functional groups other than those at the reaction point is altered under the reaction condition or if it is unsuitable for post-reaction processing. Common protecting groups described in references (T. W. Greene and P. G. M. Wuts, "Protective Group in Organic Synthesis", $3^{rd}$ Ed., John Wiley and Sons, Inc., New York (1999)) or the like can be used as the protecting groups used in these processes. A protecting group can be introduced or removed by a method that is commonly used in organic synthetic chemistry (e.g., method described in the aforementioned reference or the like) or a method in accordance therewith.

The starting material and intermediate in the manufacturing methods described below can be purchased as a commercially available product or are available by synthesis in accordance with a method described in a known document or a known method from a known compound. Salts of the starting material and intermediate can also be used, as long as the reaction is not affected.

The intermediate and compound of interest in the manufacturing methods described below can also be converted into another compound encompassed by the present invention by appropriately converting their functional groups. A functional group can be converted by a method that is commonly used in organic synthetic chemistry (e.g., the method described in R. C. Larock, "Comprehensive Organic Transformations", $2^{nd}$ Ed., John Wiley and Sons, Inc., New York (1999) or the like) or a method in accordance therewith.

An inert solvent in the manufacturing methods described below refers to a solvent that does not react with raw materials, reagents, bases, acids, catalysts, ligands, or the like that are used in a reaction (hereinafter, also referred to as "raw materials or the like used in a reaction"). A solvent used in each step can be used as an inert solvent even if the solvent reacts with the raw materials or the like used in the reaction, as long as the reaction of interest proceeds to yield a compound of interest.

The compound of the invention represented by formula (1) can be manufactured by, for example, the following Manufacturing Methods 1 to 3.

Manufacturing Method 1

The compound represented by formula (1), which can be represented by formula [A1], can be manufactured, for example, by the following manufacturing method.

[Chemical Formual 42]

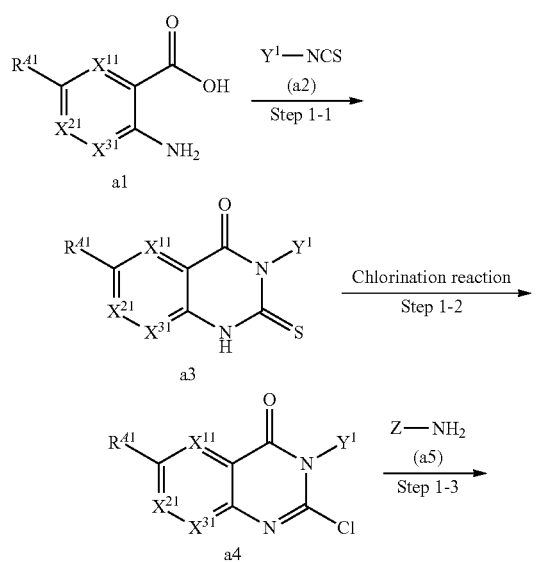

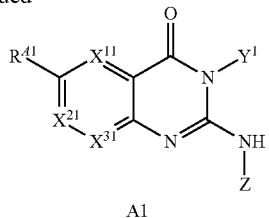

wherein $R^{41}$ is a hydrogen atom, halogen, optionally substituted $C_{1-6}$ alkyl, or optionally substituted $C_{1-6}$ alkoxy, $X^{11}$ is $CR^1$, $X^{21}$ is $CR^2$, $X^{31}$ is $CR^3$, Y is optionally substituted $C_{6-10}$ aryl, and Z, $R^1$, $R^2$, and $R^3$ are defined the same as item 1.

As compound a1, a commercially available product can be used, or the compound can be manufactured in accordance with a known method, e.g., the method described in Anais da Academia Brasileira de Ciencias 2015, 87(3), 1525-1529 or the like.

As compound a2, a commercially available product can be used, or the compound can be manufactured in accordance with a known method, e.g., the method described in International Publication No. WO 2009/131926, Organic Letters (2016), 18(2), 188-191, or the like.

[Step 1-1: Cyclization Reaction]

Compound a3 can be manufactured by reacting compound a1 with compound a2 in the presence of a suitable base, without a solvent or in a suitable solvent, at normal pressure or under pressure. The base can be appropriately selected from the bases exemplified below or the like. Preferred examples thereof include triethylamine and N,N-diisopropylethylamine. The solvent can be appropriately selected from solvents exemplified below or the like. Preferred examples thereof include ethanol and isopropanol. The reaction time is generally 5 minutes to 48 hours, and preferably 1 hour to 12 hours. The reaction temperature is generally −78° C. to 150° C., and preferably 25° C. to 150° C.

This reaction can be performed in accordance with the method described in European Journal of Medicinal Chemistry 2016, 112, 106-113, Synthetic Communications 2017, 47(11), 1040-1045 or the like.

[Step 1-2: Chlorination Reaction]

Compound a4 can be manufactured by reacting compound a3 with a suitable chlorination reagent, without a solvent or in a suitable solvent. The solvent can be appropriately selected from the solvents exemplified below or the like. Preferred examples thereof include toluene and chloroform. The chlorination reagent should be appropriately selected in accordance with the type of raw material compound or the like. Examples thereof include phosphoryl chloride, phosphorus pentachloride, thionyl chloride, sulfuryl chloride, and the like. Such chlorination reagents are used alone or as a mixture of two or more chlorination reagents, preferably as a mixture of phosphoryl chloride and phosphorous pentachloride. The reaction time is generally 5 minutes to 48 hours, and preferably 1 hour to 12 hours. The reaction temperature is generally −78° C. to 150° C., and preferably 25° C. to 150° C.

This reaction can be performed in accordance with the method described in Journal of Medicinal Chemistry 2014, 57(5), 2091-2106, Bioorganic & Medicinal Chemistry 2010, 18(8), 2836-2848, or the like.

[Step 1-3: Substitution Reaction]

Compound A1 can be manufactured by reacting compound a4 with compound a5, without a solvent or in a suitable solvent, under normal pressure or under pressure. The solvent is appropriately selected from the solvents exemplified below or the like. Examples thereof include N-methylpyrrolidone, dimethyl sulfoxide, and the like. The reaction time is generally 5 minutes to 48 hours, and preferably 5 minutes to 12 hours. The reaction temperature is generally 0° C. to 250° C., and preferably 50° C. to 200° C. This reaction can be performed in the presence of base as needed. The base is appropriately selected from the bases exemplified below or the like. Preferred examples thereof include potassium fluoride.

As compound a5, a commercially available product can be used, or the compound can be manufactured in accordance with a known method, e.g., the method described in The Journal of Organic Chemistry 2009, 74 (12), 4542-4546 or the like.

Manufacturing Method 2

The compound represented by formula (1), which can be represented by formula [B1], can be manufactured, for example, by the following manufacturing method.

[Chemical Formula 43]

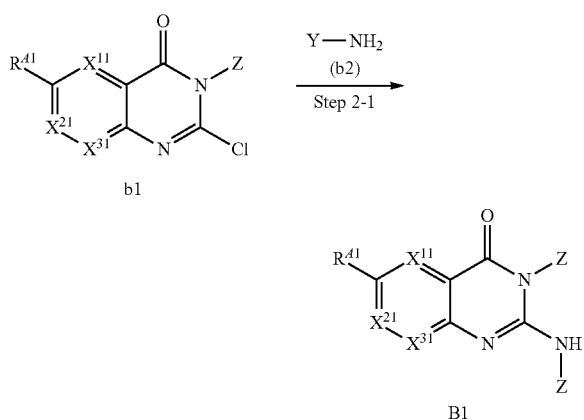

wherein $R^{41}$ is a hydrogen atom, halogen, optionally substituted $C_{1-6}$ alkyl, or optionally substituted $C_{1-6}$ alkoxy, $X^{11}$ is $CR^1$, $X^{21}$ is $CR^2$, $X^{31}$ is $CR^3$, and $R^1$, $R^2$, $R^3$, Y, and Z are defined the same as item 1.

Compound b1 and compound b2 can be manufactured in accordance with the manufacturing methods of compound a1 and compound a5, respectively, in Manufacturing Method 1.

[Step 2-1: Substitution Reaction]

Compound B1 can be manufactured in accordance with step 1-3 in Manufacturing Method 1 by using a suitable base and a suitable solvent. The solvent is appropriately selected from the solvents exemplified below or the like. Preferred examples thereof include N-methylpyrrolidone, tetrahydrofuran, and dimethyl sulfoxide. The base is appropriately selected from the bases exemplified below or the like. Preferred examples thereof include lithium bis(trimethylsilyl)amide and sodium hydride. The reaction time is generally 5 minutes to 48 hours, and preferably 5 minutes to 12 hours. The reaction temperature is generally −78° C. to 150° C., and preferably 0° C. to 100° C.

Manufacturing Method 3

The compound represented by formula (1), which can be represented by formula [C1], can be manufactured, for example, by the following manufacturing method.

[Chemical Formula 44]

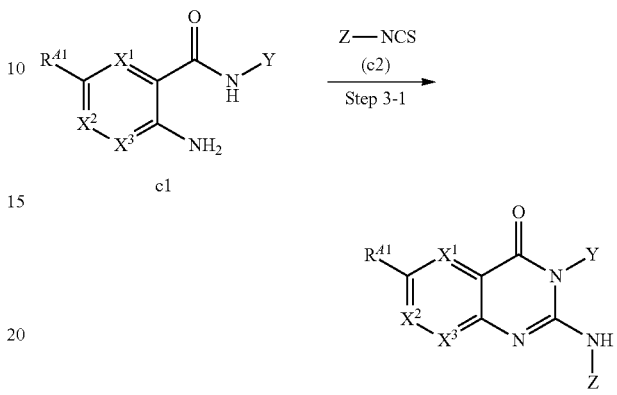

wherein $R^A$, $X^1$, $X^2$, $X^3$, Y, and Z are defined the same as item 1.

[Step 3-1: Cyclization Reaction]

Compound C1 can be manufactured by reacting compound c1 with compound c2 in the presence of copper bromide and a base, without a solvent or in a suitable solvent, under normal pressure or under pressure in accordance with the method described in Helvetica Chimica Acta (2016), 99(5), 378-383. The base can be appropriately selected from the bases exemplified below or the like. Preferred examples thereof include triethylamine and N,N-diisopropylethylamine. The solvent is appropriately selected from the solvents exemplified below or the like. Preferred examples thereof include dimethylformamide. The reaction time is generally 5 minutes to 48 hours, and preferably 1 hour to 48 hours. The reaction temperature is generally 0° C. to 150° C., and preferably 25° C. to 100° C.

As compound c1, a commercially available product can be used, or the compound can be manufactured in accordance with a known method, e.g., the method described in International Publication No. WO 2001/018536, International Publication No. WO 2001/19788, or the like.

As compound c2, a commercially available product can be used, or the compound can be manufactured from compound a5 in accordance with a known method, e.g., the method described in International Publication No. WO 2009/131926, Journal of Organic Chemistry (1986), 51(13), 2613-15, or the like.

The base used in each step of each of the manufacturing methods described above should be appropriately selected depending on the type of reaction or raw material compound or the like. Examples thereof include alkali bicarbonates such as sodium bicarbonate and potassium bicarbonate, alkali carbonates such as sodium carbonate and potassium carbonate, metal fluorides such as potassium fluoride and cesium fluoride, metal hydrides such as sodium hydride and potassium hydride, alkali metal hydroxides such as sodium hydroxide and potassium hydroxide, alkali metal alkoxides such as sodium methoxide and sodium t-butoxide, organic metal bases such as butyllithium, lithium diisopropylamide, and lithium bis(trimethylsilyl)amide, and organic bases such as triethylamine, diisopropylethylamine, pyridine, 4-dimethylaminopyridine (DMAP), and 1,8-diazabicyclo[5.4.0]-7-undecene (DBU).

The solvent used in each step of each of the manufacturing methods described above should be appropriately selected depending on the type of reaction or raw material compound or the like. Examples thereof include alcohols such as methanol, ethanol, and isopropanol, ketones such as acetone and methyl ketone, halogenated hydrocarbons such as methylene chloride and chloroform, ethers such as tetrahydrofuran (THF) and dioxane, aromatic hydrocarbons such as toluene and benzene, aliphatic hydrocarbons such as hexane and heptane, esters such as ethyl acetate and propyl acetate, amides such as N,N-dimethylformamide (DMF) and N-methyl-2-pyrrolidone, sulfoxides such as dimethyl sulfoxide (DMSO), and nitriles such as acetonitrile. These solvents can be used alone or as a mixture of two or more solvents. An organic base can also be used as a solvent depending on the type of reaction.

The compound of the invention represented by formula (1) or an intermediate thereof can be separated or purified by a method that is known to those skilled in the art. Examples thereof include extraction, partition, re-precipitation, column chromatography (e.g., silica gel column chromatography, ion exchange column chromatography, and preparative liquid chromatography), recrystallization, and the like.

Examples of recrystallization solvents that can be used include alcohol solvents such as methanol, ethanol, and 2-propanol, ether solvents such as diethyl ether, ester solvents such as ethyl acetate, aromatic hydrocarbon solvents such as benzene and toluene, ketone solvents such as acetone, halogen solvents such as dichloromethane and chloroform, hydrocarbon solvents such as hexane, aprotic solvents such as dimethylformamide and acetonitrile, water, mixtures thereof, and the like. The methods described in Jikken Kagaku Koza [*Experimental Chemistry*] (Ed. by The Chemical Society of Japan, Maruzen) Vol. 1 and the like can be used as other purification methods. The molecular structure of the compound of the invention can be readily determined by a spectroscopic method such as nuclear magnetic resonance, infrared spectroscopy, or circular dichroism spectroscopy, or mass spectrometry by referring to the structure derived from each raw material compound.

The intermediate or final product in the manufacturing method described above can lead to another compound encompassed by the present invention by appropriately converting the functional group thereof, extending various side changes from especially an amino, hydroxyl group, carbonyl, halogen, or the like, and, in doing so, applying protection and deprotection described below as needed. Conversion of a functional group and extension of a side chain can be performed using a common method that is routinely used (see, for example, Comprehensive Organic Transformations, R. C. Larock, John Wiley & Sons Inc. (1999) or the like).

Examples of protecting groups of amino that can be used include alkylcarbonyl (e.g., acetyl and propionyl), formyl, phenylcarbonyl, alkyloxycarbonyl (e.g., methoxycarbonyl, ethoxycarbonyl, and tert-butoxycarbonyl), phenyloxycarbonyl, arylalkyloxycarbonyl (e.g., benzyloxycarbonyl), trityl, phthaloyl, tocyl, and benzyl.

Examples of protecting groups of carboxyl that can be used include alkyl (e.g., methyl, ethyl, propyl, isopropyl, butyl, and tert-butyl), phenyl, benzyl, trityl, and silyl (e.g., trimethylsilyl and tert-butyldimethylsilyl).

Examples of protecting groups of hydroxy that can be used include methyl, tert-butyl, allyl, substituted methyl (e.g., methoxymethyl and methoxyethoxymethyl), ethoxyethyl, tetrahydropyranyl, tetrahydrofuranyl, trityl, arylalkyl (e.g., benzyl), alkylcarbonyl (e.g., acetyl and propionyl), formyl, benzoyl, arylalkyloxycarbonyl (e.g., benzyloxycarbonyl), and silyl (e.g., trimethylsilyl and tert-butyldimethylsilyl).

Carbonyl can be protected by converting carbonyl into acyclic ketal (dimethyl ketal, diethyl ketal, or the like) or cyclic ketal (1,3-dioxolane, 1,3-dioxane, or the like).

The compound of the invention represented by formula (1) or a pharmaceutically acceptable salt thereof can have asymmetry or a substituent having an asymmetric carbon. Such a compound has an enantiomer. The compound of the invention also encompasses mixtures of each isomer and isolated isomers, which can be manufactured in accordance with a conventional method.

Examples of the manufacturing method include a method using a raw material having an asymmetric point and a method of introducing asymmetry during the process. Enantiomers for example can be obtained by using an optically active raw material, or performing optical resolution, or the like at a suitable stage of a manufacturing step. Examples of optical resolution methods include a diastereomer method of forming a salt, when the compound represented by formula (1) or intermediate thereof has a basic functional group, in an inert solvent (e.g., an alcohol solvent such as methanol, ethanol, or 2-propanol; an ether solvent such as diethyl ether; an ester solvent such as ethyl acetate; a hydrocarbon solvent such as toluene; an aprotic solvent such as acetonitrile; or a mixture of two or more thereof) using an optically active acid (e. g., monocarboxylic acid such as mandelic acid, N-benzyloxyalanine, or lactic acid, dicarboxylic acid such as tartaric acid, ortho-diisopropylidene tartaric acid, or malic acid, or sulfonic acid such as camphorsulfonic acid or bromocamphorsulfonic acid).

When the compound of the invention represented by formula (1) or an intermediate thereof has an acidic functional group such as a carboxyl group, optical resolution can be performed by forming a salt using an optically active amine (e.g., organic amines such as 1-phenylethylamine, quinine, quinidine, cinchonidine, cinchonine, or strychnine).

A temperature for the formation of a salt is selected from the range from −50° C. to the boiling point of a solvent, preferably the range from −0° C. to the boiling point, and more preferably the range from room temperature to the boiling point of a solvent. To improve the optical purity, it is desirable to first raise the temperature to a temperature near the boiling point of a solvent. When filtering out a precipitated salt, the temperature can be cooled as needed to improve the yield. The amount of an optically active acid or amine used in the range from about 0.5 to about 2.0 equivalents and preferably approximately 1 equivalent relative to a substrate is suitable. A crystal can be recrystallized in an inert solvent (e.g., an alcohol solvent such as methanol, ethanol, or 2-propanol; an ether solvent such as diethyl ether; an ester solvent such as ethyl acetate; a hydrocarbon solvent such as toluene; an aprotic solvent such as acetonitrile; or a mixture of two or more thereof) as needed to obtain an optically active salt with high purity. An optically resolved salt can also be treated with an acid or a base by a conventional method to obtain its free form as needed.

Raw materials and intermediates in each of the manufacturing methods described above without a specific description of the manufacturing method are commercially available compounds, or compounds that can be synthesized from a commercially available compound by a method known to those skilled in the art or a method in accordance thereto.

The compound of the invention has an effect of suppressing hyperexcitation of the nerve and can be used as a therapeutic drug or a prophylactic drug for epilepsy and amyotrophic lateral sclerosis. The compound of the invention can also be used as a therapeutic drug or prophylactic drug for other diseases associated with hyperexcitation of the nerve such as autism, Parkinson's disease, Alzheimer's disease, or cognitive disorder.

As used herein, "prevention (prophylaxis)" is an act of administering an active ingredient of the invention to a healthy individual who has not developed a disease in order to, for example, prevent the onset of the disease. "Treatment (therapy)" is an act of administering an active ingredient of the invention to a person (patient) diagnosed as having developed a disease by a physician.

The route of administration of the compound of the invention can be oral administration, parenteral administration, or rectal administration. The daily dosage thereof varies by the type of compound, administration method, patient's symptom or age, or the like. For oral administration, generally about 0.01 to 1000 mg and still more preferably about 0.1 to 500 mg per 1 kg of body weight of a human or mammal can be administered in one to several doses. For parenteral administration such as intravenous administration, generally about 0.01 mg to 300 mg and still more preferably about 1 mg to 100 mg per 1 kg of body weight of a human or mammal can be administered.

The compound of the invention can be administered directly or after being formulated into a suitable dosage form by parenteral or oral administration. Examples of the dosage form include, but are not limited to, a tablet, a capsule, powder, a granule, a liquid agent, a suspension, an injection, a patch, a poultice, and the like. A formulation can be manufactured by a known method using a pharmaceutically acceptable additive. An excipient, disintegrant, binding agent, fluidizer, lubricant, coating agent, solubilizing agent, solubilizing adjuvant, thickener, dispersant, stabilizing agent, sweetener, flavoring agent, and the like can be used as an additive in accordance with the objective. Specific examples thereof include lactose, mannitol, crystalline cellulose, low substituted hydroxypropyl cellulose, corn starch, partially pregelatinized starch, carmellose calcium, croscarmellose sodium, hydroxypropyl cellulose, hydroxypropylmethyl cellulose, polyvinyl alcohol, magnesium stearate, sodium stearyl fumarate, polyethylene glycol, propylene glycol, titanium oxide, talc, and the like.

The compound of the invention can be used concomitantly with another amyotrophic lateral sclerosis drug or antiepileptic drug. Examples of amyotrophic lateral sclerosis drugs include riluzole, edaravone, and the like. Examples of antiepileptic drugs include phenytoin, carbamazepine, phenobarbital, zonisamide, sodium valproate, and the like.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present invention has been described while showing preferred embodiments to facilitate understanding. While the present invention is described hereinafter based on the Examples, the above descriptions and the following Examples are provided for the sole purpose of exemplification, not limitation of the present invention. Thus, the scope of the present invention is not limited to the embodiments and Examples that are specifically described herein and is limited only by the scope of claims.

EXAMPLES

While the present invention is described more specifically with Reference Examples, Examples, and Test Examples hereinafter, the preset invention is not limited thereto. The compound names denoted in the following Reference Examples and Examples do not necessarily follow the IUPAC nomenclature.

The following abbreviations may be used in the Reference Examples, Examples, and Tables in the Examples to simplify the descriptions herein. As abbreviations used for a substituent, Me refers to methyl, Ms refers to methanesulfonyl, Ph refers to phenyl, and TFA refers to trifluoroacetic acid. As symbols used for NMR, s refers to singlet, d refers to doublet, dd refers to double doublet, t refers to triplet, td refers to 3 doublet, q refers to quartet, m refers to multiplet, br refers to broad, brs refers to broad singlet, brs refers to broad multiplet, and J refers to a coupling constant.

High performance liquid chromatography-mass spectrometer; measurement conditions of LCMS are as follows. The observed mass spectrometry value [MS (m/z)] is indicated by MH$^+$, and time of retention is indicated by Rt (min). The measurement conditions used for measurement are described for each of the actual measurement values.
Measurement Condition A
Detector: Agilent 1200 series, Agilent 6110 Quadrupole LC/MS
Column: SunFire C18 (3×30 mm, 2.5 μm)
Solvent:
  Solution A: 0.01% TFA/H$_2$O, solution B: 0.01% TFA/MeCN Gradient Condition:
  0.0-0.2 minutes; A/B=95:5
  0.2-1.5 minutes; A/B=95:5 to 5:95 (linear gradient)
  1.5-2.8 minutes; A/B=5:95
Flow rate; 1.5 ml/minute
UV: 254 nm
Column temperature: 50° C.

Reference Example 1

2-chloro-6-fluoro-3-phenylquinazolin-4(3H)-one

[Chemical Formula 45]

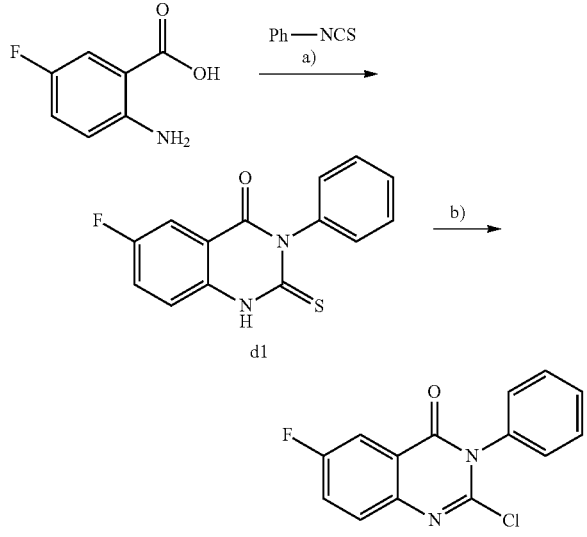

Reference Example 1 a) Manufacture of 6-fluoro-3-phenyl-2-sulfa-nylidene-2,3-dihydroquinazolin-4(1H)-one (Compound d1)

Phenyl isothiocyanate (2.02 g) was added to an ethanol (35 ml) solution of 5-fluoroanthranilic acid (1.55 g) and N,N-diisopropylethylamine (2.58 g). The mixture was stirred for 8 hours while heating under reflux. After cooling the reaction solution to room temperature, the resulting solid was filtered out and washed with ethanol. The solid was dried under reduced pressure at room temperature to obtain compound d1 (2.5 g).
LC-MS (measurement condition A), m/z; 457 (M+H)+ ESI, Rt; 1.58 b) Manufacture of 2-chloro-6-fluoro-3-phenylqui-nazolin-4(3H)-one (Reference Example 1)

A mixture of compound d1 (2.17 g), phosphorus pentachloride (4.16 g), and phosphorus oxychloride (18.3 g) was stirred for 6 hours while heating under reflux. The reaction solution was poured into ice water. The resulting solid was filtered out and washed with water. The crude product was dissolved in ethyl acetate and washed with saturated saline and subsequently with saturated sodium bicarbonate water. The organic layer was dried with anhydrous sodium sulfate, filtered, and concentrated under reduced pressure to obtain Reference Example 1 (2.0 g).
$^1$H NMR (400 MHz, CDCl$_3$) δ: 7.29-7.32 (2H, m), 7.52-7.61 (4H, m), 7.72-7.75 (1H, m), 7.90-7.93 (1H, m).

Reference Example 2

2-amino-5-chloro-N-(pyridin-3-yl)benzamide

[Chemical Formula 46]

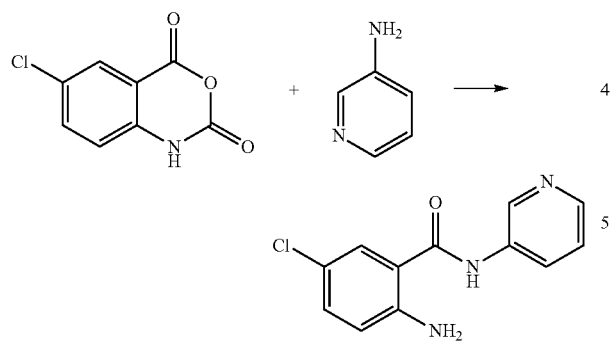

Reference Example 2

6-chloro-2H-3,1-benzoxazine-2,4(1H)-dione (400 mg) and pyridin-3-amine (950 mg) were stirred for 5 hours at 110° C. The reaction solution was purified in an amino silica gel column (eluent; hexane: ethyl acetate) to obtain Reference Example 2 (240 mg).
$^1$H NMR (400 MHz, DMSO-D$_6$) δ: 6.54 (2H, s), 6.80 (1H, d, J=7.2 Hz), 7.25-7.27 (1H, m), 7.37-7.40 (1H, m), 7.73 (1H, d, J=1.6 Hz), 8.10-8.12 (1H, m), 8.30-8.31 (1H, m), 8.87 (1H, d, J=1.6 Hz), 10.27 (1H, s).

Reference Example 3

2-chloro-4-fluoro-1-isothiocyanatobenzene

[Chemical Formula 47]

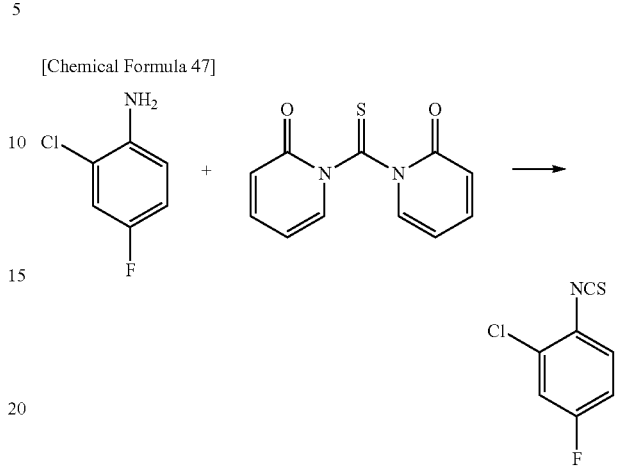

Reference Example 3

A dichloromethane (10 ml) solution of 2-chloro-4-fluoroaniline (1.0 g) and 1,1'-carbonothionyldi(pyridin-(1H)-one) (1.6 g) was stirred for 3 hours at room temperature. The reaction solution was purified by silica gel column chromatography (eluent; hexane: ethyl acetate) to obtain Reference Example 3 (1.3 g).
$^1$H-NMR (400 MHz, CDCl$_3$) δ: 6.91-7.02 (1H, m), 7.13-7.28 (2H, m).

Reference Example 4

(4-isothiocyanatophenyl)methanol

[Chemical Formula 48]

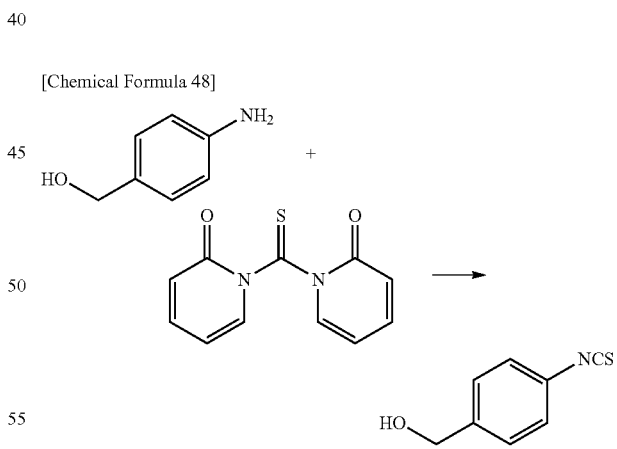

Reference Example 4

A dichloromethane (400 ml) solution of (4-aminophenyl)methanol (25.0 g) and 1,1'-carbonothionyldi(pyridin-(1H)-one) (47.1 g) was stirred for 5 hours at room temperature. The reaction solution was purified by silica gel column chromatography (eluent; hexane: ethyl acetate) to obtain Reference Example 4 (23.5 g)
$^1$H NMR (400 MHz, DMSO-D$_6$) δ: 4.49 (2H, d, J=5.6 Hz), 5.30 (1H, t, J=5.6 Hz), 7.40-7.35 (4H, m).

Example 1

2-anilino-6-fluoro-3-phenylquinazolin-4 (3H)-one

[Chemical Formula 49]

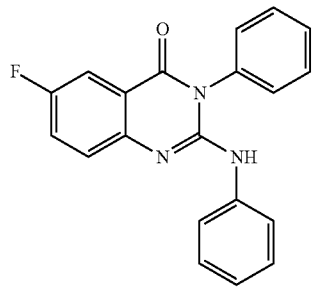

An N-methylpyrrolidone (10 ml) solution of Reference Example 1 (5 g) and aniline (5.1 g) was stirred for 3 hours at 130° C. The reaction solution was poured into an aqueous 0.2 mol/L sodium hydroxide solution (100 ml). The resulting solid was filtered out and washed with water. The solid was suspended in methanol, filtered out, and dried to obtain Example 1 (4.4 g).

$^1$H NMR (400 MHz, CDCl$_3$) δ: 5.95 (1H, s), 7.09-7.14 (1H, m), 7.31-7.56 (8H, m), 7.62-7.71 (3H, m), 7.81-7.84 (1H, m).

Example 2

2-anilino-6-fluoro-3-(5-methylpyridin-3-yl)quinazolin-4(3H)-one

[Chemical Formula 50]

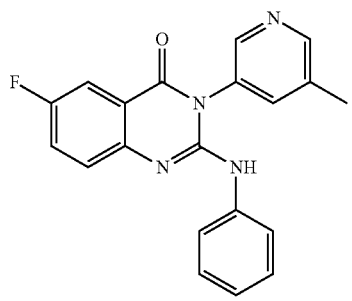

Lithium bis(trimethylsilyl)amide (91 mg) was added to a dimethyl sulfoxide (1 mL) solution of Reference Example 1 (50 mg) and 5-methylpyridin-3-amine (59.1 mg). The mixture was stirred for 30 minutes at room temperature. An aqueous saturated ammonium chloride solution was added to the reaction solution. The resulting solid was filtered out. The crude product was generated by silica gel column chromatography (eluent; hexane: ethyl acetate) to obtain Example 2 (20.0 mg).

$^1$H-NMR (400 MHz, CDCl$_3$) δ: 2.43 (3H, s), 7.05 (1H, t, J=7.3 Hz), 7.25 (2H, t, J=7.6 Hz), 7.34 (1H, td, J=8.4, 2.8 Hz), 7.38-7.47 (3H, m), 7.56 (1H, s), 7.72 (1H, dd, J=8.2, 2.7 Hz), 8.43 (1H, s), 8.58 (1H, s).

Example 3

6-chloro-2-(2-chloro-4-fluoroanilino)-3-(pyridin-3-yl)quinazolin-4(3H)-one

[Chemical Formula 51]

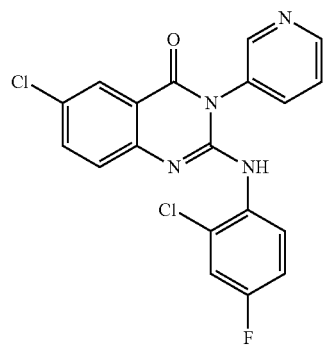

A dimethylformamide (2 mL) solution of Reference Example 2 (100 mg), Reference Example 3 (76.0 mg), copper bromide (57.9 mg), and triethylamine (40.9 mg) was stirred for 4 hours at 80° C. The reaction solution was purified by amino silica gel column chromatography (eluent; hexane:ethyl acetate) to obtain Example 3 (10.1 mg).

$^1$H-NMR (400 MHz, CDCl$_3$) δ: 6.35 (1H, s), 7.04-7.12 (2H, m), 7.49 (1H, d, J=8.5 Hz), 7.61-7.68 (2H, m), 7.80-7.86 (1H, m), 8.15 (1H, d, J=2.4 Hz), 8.56-8.63 (1H, m), 8.74 (1H, d, J=1.8 Hz), 8.89 (1H, d, J=3.7 Hz).

Example 4

6-chloro-2-[4-(hydroxymethyl)anilino]-3-phenylquinazolin-4 (3H)-one

[Chemical Formula 52]

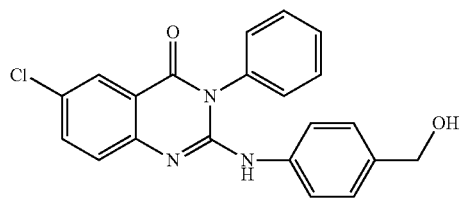

A reaction was performed in the same manner as Example 3 using a corresponding raw material compound (Reference Example 4) to obtain Example 4.

$^1$H NMR (400 MHz, DMSO-D$_6$) δ: 4.45 (2H, d, J=5.2 Hz), 5.13 (1H, t, J=5.2 Hz), 7.24 (2H, d, J=8.4 Hz), 7.32 (1H, d, J=8.8 Hz), 7.39-7.41 (2H, m), 7.49-7.67 (7H, m), 7.88 (1H, d, J=2.4 Hz).

Example 5

4-[(6-chloro-4-oxo-3-phenyl-3,4-dihydroquinazolin-2-yl)amino]benzaldehyde

[Chemical Formula 53]

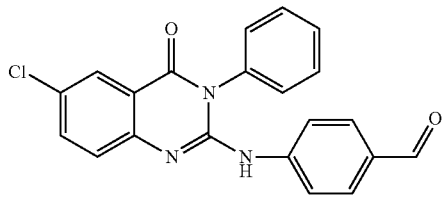

Manganese dioxide (851 mg) was added to a dichloromethane (3 ml) solution of Example 4 (370 mg). The mixture was stirred for 3 hours at room temperature. The reaction solution was filtered through Celite, and the filtrate was concentrated under reduced pressure to obtain Example 5 (368 mg).
$^1$H-NMR (400 MHz, DMSO-D$_6$) δ: 7.46 (1H, d, J=8.5 Hz), 7.50 (2H, d, J=6.7 Hz), 7.53-7.63 (3H, m), 7.72-7.84 (5H, m), 7.93 (1H, d, J=2.4 Hz), 8.00 (1H, s), 9.88 (1H, s).

Example 6

6-chloro-2-{4-[(dimethylamino)methyl]anilino}-3-phenylquinazolin-4(3H)-one

[Chemical Formula 54]

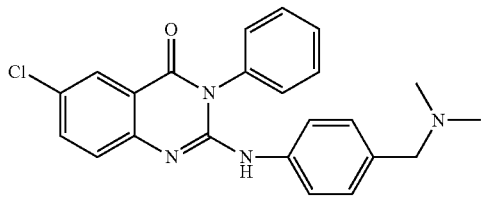

Sodium triacetoxyborohydride (60 mg) was added to a dichloromethane (1 ml) solution of Example 5 (50 mg) and 10% dimethylamine THF solution (0.13 ml). The mixture was stirred for 12 hours at room temperature. The reaction solution was purified by amino silica gel column chromatography (eluent; hexane: ethyl acetate) to obtain Example 6 (17 mg).
$^1$H-NMR (400 MHz, DMSO-D$_6$) δ: 2.11 (6H, s), 3.32 (2H, s), 7.18 (2H, d, J=8.5 Hz), 7.33 (1H, d, J=9.2 Hz), 7.40 (2H, d, J=7.9 Hz), 7.46-7.51 (3H, m), 7.52-7.63 (3H, m), 7.65 (1H, dd, J=9.2, 2.4 Hz), 7.87 (1H, d, J=2.4 Hz).

Example 30

6-chloro-2-{4-[(3,3-difluoroazetidin-1-yl)methyl]anilino}-3-phenylquinazolin-4(3H)-one

[Chemical Formula 55]

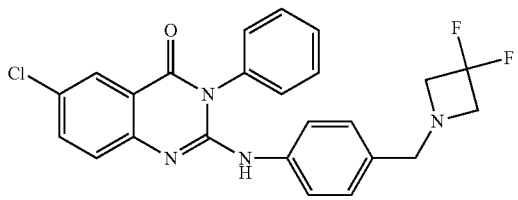 [SMILES: O=c1c2cc(Cl)ccc2nc(Nc2ccc(CN3CC(F)(F)C3)cc2)n1-c1ccccc1]

Acetic acid (0.64 g) was added to a dimethyl sulfoxide (12 ml) solution of Example 5 (1 g), 3,3-difluoroazetidine hydrochloride (0.69 g), and N,N-diisopropylethylamine (0.67 g). The mixture was stirred for 20 minutes at 60° C. Sodium triacetoxyborohydride (1.13 g) was added, and the mixture was stirred for 6 hours at 60° C. The reaction solution was poured into an aqueous 0.5 mol/L sodium hydroxide solution. The eluted solid was filtered out. After drying, the crude product was purified by silica gel column chromatography (eluent; hexane: ethyl acetate) to obtain Example 30 (0.98 g).
$^1$H-NMR (400 MHz, DMSO-D$_6$) δ: 3.55 (4H, t, J=12.3 Hz), 3.66 (2H, s), 7.21 (2H, d, J=8.7 Hz), 7.33 (1H, d, J=9.1 Hz), 7.42 (2H, d, J=8.7 Hz), 7.46-7.53 (3H, m), 7.53-7.63 (4H, m), 7.66 (1H, dd, J=8.9, 2.5 Hz), 7.87 (1H, d, J=2.3 Hz).

Examples 7 to 188

Reactions/treatment were performed in the same manner as Examples 1 to 6 using a corresponding raw material compound to obtain the compounds shown in Table 1.

TABLE 1

| Example | Structural formula | $^1$H NMR |
| --- | --- | --- |
| 7 |  | $^1$H NMR (400 MHz, DMSO-D$_6$) δ: 2.86 (6H, s), 6.46 (1H, dd, J = 2.0, 8.0 Hz), 6.71 (1H, d, J = 8.8 Hz), 6.97 (1H, s), 7.07 (1H, t, J = 8.4 Hz), 7.25 (1H, s), 7.33 (1H, d, J = 8.4 Hz), 7.48-7.50 (2H, m), 7.54-7.68 (4H, m), 7.88 (1H, d, J = 2.8 Hz). |

TABLE 1-continued

| Example | Structural formula | $^1$H NMR |
|---|---|---|
| 8 | | $^1$H NMR (400 MHz, CDCl$_3$) δ: 1.71 (1H, t, J = 5.6 Hz), 4.70 (2H, d, J = 5.6 Hz), 6.01 (1H, s,), 7.10 (1H, d, J = 7.6 Hz), 7.33 (1H, t, J = 7.6 Hz), 7.41-7.44 (3H, m), 7.48 (1H, d, J = 8.4 Hz), 7.54-7.55 (1H, m), 7.57-7.60 (1H, m), 7.59-7.70 (3H, m), 8.14 (1H, d, J = 2.4 Hz). |
| 9 | | $^1$H NMR (400 MHz, CDCl$_3$) δ: 6.21 (1H, s), 7.26-7.42 (2H, m,), 7.52-7.60 (3H, m,), 7.64-7.70 (6H, m,), 8.16 (1H, d, J = 2.4 Hz,). |
| 10 | | $^1$H NMR (400 MHz, CDCl$_3$) δ: 6.09 (1H, s), 7.39-7.44 (4H, m), 7.53 (1H, d, J = 8.4 Hz), 7.56-7.59 (1H, m), 7.64-7.73 (4H, m), 8.08-8.09 (1H, m), 8.15-8.16 (1H, m). |
| 11 | | $^1$H NMR (400 MHz, DMSO-D$_6$) δ: 3.81 (3H, s), 7.43 (1H, d, J = 8.8 Hz), 7.48-7.50 (2H, m), 7.55-7.74 (6H, m), 7.86-7.91 (4H, m). |

TABLE 1-continued

| Example | Structural formula | ¹H NMR |
|---|---|---|
| 12 | | ¹H NMR (400 MHz, DMSO-D₆) δ: 3.18 (3H, s), 7.36 (1H, d, J = 8.8 Hz), 7.50-7.52 (2H, m), 7.56-7.61 (5H, m), 7.72 (1H, dd, J = 2.8, 8.8 Hz), 7.91-7.94 (2H, m), 8.09 (2H, s). |
| 13 | | ¹H NMR (400 MHz, CDCl₃) δ: 6.60 (1H, s), 6.98-7.11 (2H, m), 7.43 (2H, d, J = 7.9 Hz), 7.47 (1H, d, J = 9.2 Hz), 7.55-7.74 (4H, m), 8.15 (1H, d, J = 2.4 Hz), 8.67 (1H, dd, J = 9.8, 5.5 Hz). |
| 14 | | ¹H NMR (400 MHz, CDCl₃) δ: 5.94 (1H, s), 6.88-6.93 (1H, m), 7.06 (1H, q, J = 9.2 Hz), 7.38-7.42 (2H, m), 7.48 (1H, d, J = 9.2 Hz), 7.58-7.71 (4H, m), 7.73-7.80 (1H, m), 8.13 (1H, d, J = 2.4 Hz). |
| 15 | | ¹H NMR (400 MHz, DMSO-D₆) δ: 7.24 (1H, s), 7.40 (1H, d, J = 8.8 Hz), 7.50-7.52 (2H, m), 7.58-7.63 (5H, m), 7.71 (1H, dd, J = 2.8, 8.8 Hz), 7.75 (1H, s), 7.79-7.82 (2H, m), 7.86 (1H, s), 7.91 (1H, d, J = 2.8 Hz). |

TABLE 1-continued

| Example | Structural formula | ¹H NMR |
|---|---|---|
| 16 | 6-chloro-3-phenyl-2-[(2-chlorophenyl)amino]quinazolin-4(3H)-one | ¹H NMR (400 MHz, CDCl₃) δ: 6.81 (1H, s), 7.00 (1H, td, J = 7.8, 1.4 Hz), 7.28 (1H, dd, J = 7.8, 1.2 Hz), 7.31-7.35 (1H, m), 7.44 (2H, d, J = 7.3 Hz), 7.51 (1H, d, J = 8.5 Hz), 7.59-7.72 (4H, m), 8.16 (1H, d, J = 2.4 Hz), 8.75 (1H, dd, J = 8.2, 1.5 Hz). |
| 17 | 6-chloro-3-phenyl-2-[(2-chloro-4-cyanophenyl)amino]quinazolin-4(3H)-one | ¹H NMR (400 MHz, CDCl₃) δ: 7.15 (1H, s), 7.43 (2H, d, J = 7.3 Hz), 7.54-7.58 (2H, m), 7.61-7.74 (5H, m), 8.19 (1H, d, J = 2.4 Hz), 9.11 (1H, d, J = 8.5 Hz). |
| 18 | 6-chloro-3-phenyl-2-[(2-chloro-4-methylphenyl)amino]quinazolin-4(3H)-one | ¹H NMR (400 MHz, CDCl₃) δ: 2.29 (3H, s), 6.66 (1H, s), 7.12 (2H, d, J = 9.8 Hz), 7.43 (2H, dd, J = 7.0, 1.5 Hz), 7.48 (1H, d, J = 8.5 Hz), 7.59-7.63 (2H, m), 7.66-7.70 (2H, m), 8.15 (1H, d, J = 2.4 Hz), 8.54 (1H, d, J = 7.9 Hz). |
| 19 | 6-chloro-3-phenyl-2-[(2,4-difluorophenyl)amino]quinazolin-4(3H)-one | ¹H NMR (400 MHz, CDCl₃) δ: 6.12 (1H, s), 6.78-6.83 (1H, m), 6.88-6.98 (1H, m), 7.39-7.44 (2H, m), 7.45 (1H, d, J = 8.5 Hz), 7.57-7.71 (4H, m), 8.14 (1H, d, J = 2.4 Hz), 8.40-8.47 (1H, m) |

TABLE 1-continued

| Example | Structural formula | ¹H NMR |
|---|---|---|
| 20 | | ¹H NMR (400 MHz, CDCl₃) δ: 3.78 (3H, s), 6.44 (1H, s), 6.84-6.91 (2H, m), 7.41-7.46 (3H, m), 7.55-7.71 (4H, m), 8.14 (1H, d, J = 2.4 Hz), 8.45 (1H, t, J = 7.3 Hz). |
| 21 | | ¹H NMR (400 MHz, CDCl₃) δ: 3.59 (3H, s), 6.53 (1H, dd, J = 10.1, 2.7 Hz), 6.72 (2H, td, J = 8.6, 2.8 Hz), 7.38-7.42 (2H, m), 7.49 (1H, d, J = 8.6 Hz), 7.56-7.71 (4H, m), 8.13 (1H, d, J = 2.4 Hz), 8.61 (1H, dd, J = 8.5, 6.1 Hz). |
| 22 | | ¹H NMR (400 MHz, DMSO-D₆) δ: 7.17-7.23 (3H, m), 7.31 (1H, d, J = 8.8 Hz), 7.43 (1H, s), 7.53 (2H, d, J = 7.2 Hz), 7.57-7.68 (4H, m), 7.71-7.75 (1H, m), 7.90 (1H, d, J = 2.8 Hz). |
| 23 | | ¹H NMR (400 MHz, DMSO-D₆) δ: 2.28-2.37 (4H, m), 3.40 (2H, s), 3.55 (4H, t, J = 4.6 Hz), 7.21 (2H, d, J = 8.5 Hz), 7.33 (1H, d, J = 8.5 Hz), 7.41 (2H, d, J = 8.5 Hz), 7.46-7.52 (3H, m), 7.52-7.63 (3H, m), 7.66 (1H, dd, J = 8.9, 2.7 Hz), 7.87 (1H, d, J = 3.1 Hz). |
| 24 | | ¹H NMR (400 MHz, DMSO-D₆) δ: 2.29-2.36 (4H, m), 3.40 (2H, s), 3.55 (4H, t, J = 4.6 Hz), 7.21 (2H, d, J = 8.5 Hz), 7.33 (1H, d, J = 8.5 Hz), 7.41 (2H, d, J = 8.5 Hz), 7.45-7.52 (3H, m), 7.52-7.63 (3H, m), 7.66 (1H, dd, J = 8.9, 2.7 Hz), 7.87 (1H, d, J = 3.1 Hz). |

TABLE 1-continued

| Example | Structural formula | ¹H NMR |
|---|---|---|
| 25 | | ¹H NMR (400 MHz, DMSO-D$_6$) δ: 1.90-1.99 (2H, m), 3.07 (4H, t, J = 6.9 Hz), 3.44 (2H, s), 7.16 (2H, d, J = 8.2 Hz), 7.32 (1H, d, J = 8.7 Hz), 7.37 (2H, d, J = 8.2 Hz), 7.45-7.50 (3H, m), 7.52-7.63 (3H, m), 7.65 (1H, dd, J = 8.7, 2.7 Hz), 7.87 (1H, d, J = 2.7 Hz). |
| 26 | | ¹H NMR (400 MHz, DMSO-D$_6$) δ: 1.00 (3H, t, J = 7.0 Hz), 2.07 (3H, s), 2.35 (2H, q, J = 7.0 Hz), 3.38 (2H, s), 7.19 (2H, d, J = 8.2 Hz), 7.32 (1H, d, J = 8.7 Hz), 7.36-7.43 (2H, m), 7.44-7.51 (3H, m), 7.52-7.70 (4H, m), 7.87 (1H, d, J = 2.3 Hz). |
| 27 | | ¹H NMR (400 MHz, DMSO-D$_6$) δ: 0.95 (6H, t, J = 7.1 Hz), 2.42 (4H, q, J = 7.1 Hz), 3.46 (2H, s), 7.21 (2H, d, J = 8.2 Hz), 7.32 (1H, d, J = 8.7 Hz), 7.38 (2H, d, J = 7.8 Hz), 7.45-7.51 (3H, m), 7.52-7.63 (3H, m), 7.65 (1H, dd, J = 9.1, 2.3 Hz), 7.87 (1H, d, J = 2.3 Hz). |
| 28 | | ¹H NMR (400 MHz, DMSO-D$_6$) δ: 2.12 (3H, s), 2.45-2.53 (2H, m), 3.21 (3H, s), 3.38-3.46 (4H, m), 7.17-7.20 (2H, m), 7.25-7.41 (3H, m), 7.43-7.51 (3H, m), 7.51-7.69 (4H, m), 7.86 (1H, d, J = 2.3 Hz). |
| 29 | | ¹H NMR (400 MHz, DMSO-D$_6$) δ: 3.24 (4H, s), 3.42 (2H, s), 4.58 (4H, s), 7.13 (2H, d, J = 8.2 Hz), 7.31 (1H, d, J = 9.6 Hz), 7.36 (2H, d, J = 7.3 Hz), 7.43-7.69 (7H, m), 7.87 (1H, s). |
| 30 | | ¹H NMR (400 MHz, DMSO-D$_6$) δ: 3.55 (4H, t, J = 12.3 Hz), 3.66 (2H, s), 7.21 (2H, d, J = 8.7 Hz), 7.33 (1H, d, J = 9.1 Hz), 7.42 (2H, d, J = 8.7 Hz), 7.46-7.53 (3H, m), 7.53-7.63 (4H, m), 7.66 (1H, dd, J = 8.9, 2.5 Hz), 7.87 (1H, d, J = 2.3 Hz). |
| 31 | | ¹H NMR (400 MHz, DMSO-D$_6$) δ: 1.15 (6H, s), 2.85 (4H, s), 3.47 (2H, s), 7.16 (2H, d, J = 8.7 Hz), 7.32 (1H, d, J = 8.7 Hz), 7.36 (2H, d, J = 8.7 Hz), 7.45-7.51 (3H, m), 7.53-7.63 (3H, m), 7.65 (1H, dd, J = 8.7, 2.7 Hz), 7.87 (1H, d, J = 2.3 Hz). |

TABLE 1-continued

| Example | Structural formula | ¹H NMR |
|---|---|---|
| 32 | | ¹H NMR (400 MHz, DMSO-D₆) δ: 2.71 (2H, td, J = 6.0, 1.9 Hz), 3.43 (2H, td, J = 6.0, 1.9 Hz), 3.48 (2H, s), 4.15 (1H, q, J = 6.2 Hz), 5.25 (1H, d, J = 6.4 Hz), 7.15 (2H, d, J = 8.2 Hz), 7.32 (1H, d, J = 8.7 Hz), 7.37 (2H, d, J = 8.7 Hz), 7.45-7.51 (3H, m), 7.52-7.63 (3H, m), 7.65 (1H, dd, J = 8.7, 2.3 Hz), 7.87 (1H, d, J = 2.3 |
| 33 | | ¹H NMR (400 MHz, DMSO-D₆) δ: 1.33 (3H, s), 2.84 (2H, d, J = 7.3 Hz), 3.12 (2H, dd, J = 5.7, 1.6 Hz), 3.50 (2H, s), 5.11 (1H, s), 7.16 (2H, d, J = 8.7 Hz), 7.33 (1H, d, J = 8.7 Hz), 7.37 (2H, d, J = 8.2 Hz), 7.46-7.51 (3H, m), 7.52-7.63 (3H, m), 7.65 (1H, dd, J = 8.7, 2.7 Hz), 7.87 (1H, d, J = 2.3 Hz). |
| 34 | | ¹H NMR (400 MHz, DMSO-D₆) δ: 2.30 (3H, s), 3.20 (2H, q, J = 10.2 Hz), 3.64 (2H, s), 7.22 (2H, d, J = 8.2 Hz), 7.33 (1H, t, J = 4.3 Hz), 7.43 (2H, d, J = 8.2 Hz), 7.46-7.64 (6H, m), 7.66 (1H, dd, J = 8.7, 2.7 Hz), 7.88 (1H, d, J = 2.7 Hz). |
| 35 | | ¹H NMR (400 MHz, DMSO-D₆) δ: 3.03-3.17 (2H, m), 3.45-3.58 (4H, m), 5.05-5.24 (1H, m), 7.18 (2H, d, J = 8.5 Hz), 7.32 (1H, d, J = 9.2 Hz), 7.40 (2H, d, J = 8.5 Hz), 7.44-7.52 (3H, m), 7.52-7.63 (3H, m), 7.66 (1H, dd, J = 9.2, 2.4 Hz), 7.87 (1H, d, J = 3.1 Hz). |
| 36 | | ¹H NMR (400 MHz, DMSO-D₆) δ: 2.76-2.92 (1H, m), 3.05 (2H, t, J = 6.7 Hz), 3.25 (2H, t, J = 7.9 Hz), 3.50 (2H, s), 6.21 (1H, td, J = 56.9, 5.3 Hz), 7.17 (2H, d, J = 8.5 Hz), 7.32 (1H, d, J = 8.5 Hz), 7.39 (2H, d, J = 8.5 Hz), 7.46-7.51 (3H, m), 7.52-7.63 (3H, m), 7.65 (1H, dd, J = 8.5, 2.4 Hz), 7.87 (1H, d, J = 2.4 Hz). |
| 37 | | ¹H NMR (400 MHz, DMSO-D₆) δ: 2.80 (2H, t, J = 5.7 Hz), 3.12 (3H, s), 3.43 (2H, t, J = 5.7 Hz), 3.51 (2H, s), 3.89-3.99 (1H, m), 7.16 (2H, d, J = 7.8 Hz), 7.32 (1H, d, J = 8.7 Hz), 7.38 (2H, d, J = 8.2 Hz), 7.46-7.50 (3H, m), 7.52-7.63 (3H, m), 7.66 (1H, d, J = 6.4 Hz), 7.87 (1H, d, J = 2.3 Hz). |
| 38 | | ¹H NMR (400 MHz, DMSO-D₆) δ: 2.23 (3H, s), 2.74 (2H, td, J = 15.5, 4.4 Hz), 3.55 (2H, s), 6.11 (1H, tt, J = 55.7, 4.4 Hz), 7.21 (2H, d, J = 8.7 Hz), 7.33 (1H, d, J = 9.1 Hz), 7.42 (2H, d, J = 8.2 Hz), 7.46-7.53 (3H, m), 7.54-7.63 (3H, m), 7.66 (1H, dd, J = 8.9, 2.5 Hz), 7.87 (1H, d, J = 2.7 Hz). |

TABLE 1-continued

| Example | Structural formula | ¹H NMR |
|---|---|---|
| 39 | | ¹H NMR (400 MHz, DMSO-D₆) δ: 3.17 (3H, s), 7.45 (1H, d, J = 8.8 Hz), 7.49-7.60 (5H, m), 7.75 (1H, dd, J = 4.8, 8.8 Hz), 7.81 (4H, s), 7.93 (1H, d, J = 2.0 Hz), 8.07 (1H, s). |
| 40 | | ¹H NMR (400 MHz, DMSO-D₆) δ: 6.87-6.90 (1H, m), 7.28-7.31 (2H, m), 7.40 (1H, d, J = 8.8 Hz), 7.48-7.63 (6H, m), 7.71 (1H, dd, J = 5.2, 8.8 Hz), 7.74 (1H, s), 7.90 (1H, d, J = 2.4 Hz). |
| 41 | | ¹H NMR (400 MHz, DMSO-D₆) δ: 3.65 (3H, s), 7.36 (1H, d, J = 8.8 Hz), 7.50-7.52 (2H, m), 7.56-7.61 (5H, m), 7.72 (1H, dd, J = 2.8, 8.8 Hz), 7.91-7.94 (2H, m), 8.09 (2H, s) |
| 42 | | ¹H NMR (400 MHz, CDCl₃) δ: 6.23 (1H, s), 7.27-7.43 (2H, m), 7.52-7.60 (3H, m), 7.64-7.70 (6H, m), 8.16 (1H, d, J = 2.4 Hz). |
| 43 | | ¹H NMR (400 MHz, DMSO-D₆) δ: 7.13 (1H, t, J = 7.3 Hz), 7.32 (2H, t, J = 7.9 Hz), 7.46 (2H, d, J = 7.9 Hz), 7.53 (2H, d, J = 7.9 Hz), 7.55-7.68 (3H, m), 7.80 (2H, d, J = 11.6 Hz), 8.53 (1H, s). |

TABLE 1-continued

| Example | Structural formula | ¹H NMR |
|---|---|---|
| 44 | | ¹H NMR (400 MHz, DMSO-D₆) δ: 7.37 (2H, d, J = 9.1 Hz), 7.47-7.53 (4H, m), 7.56-7.65 (3H, m), 7.79 (1H, s), 7.97 (1H, s), 8.54 (1H, br s). |
| 45 | | ¹H NMR (400 MHz, CDCl₃) δ: 6.15 (1H, s), 7.11 (1H, t, J = 7.3 Hz), 7.31 (2H, t, J = 7.6 Hz), 7.41 (2H, d, J = 7.3 Hz), 7.50 (2H, d, J = 7.9 Hz), 7.60-7.73 (3H, m), 8.40 (1H, d, J = 2.4 Hz), 8.74 (1H, d, J = 3.0 Hz). |
| 46 | | ¹H NMR (400 MHz, CDCl₃) δ: 6.03 (1H, s), 7.12 (1H, t, J = 7.0 Hz), 7.31 (2H, t, J = 7.9 Hz), 7.35-7.46 (4H, m), 7.52 (1H, d, J = 8.5 Hz), 7.57-7.70 (3H, m), 7.77 (1H, d, J = 8.5 Hz). |
| 47 | | ¹H NMR (400 MHz, CDCl₃) δ: 5.76 (1H, s), 7.14 (1H, t, J = 7.6 Hz), 7.32-7.36 (2H, m), 7.47 (3H, d, J = 8.8 Hz), 7.60-7.64 (2H, m), 7.81 (1H, d, J = 7.6 Hz), 8.12 (1H, d, J = 2.8 Hz), 8.71-8.74 (1H, m), 8.86-8.89 (1H, m). |
| 48 | | ¹H NMR (400 MHz, DMSO-D₆) δ: 7.10 (1H, t, J = 7.6 Hz), 7.29-7.34 (3H, m), 7.44-7.46 (2H, m), 7.60-7.63 (1H, m), 7.66-7.71 (2H, m), 7.89 (1H, d, J = 2.4 Hz), 7.97 (1H, s), 8.07-8.12 (1H, m), 8.70-8.71 (1H, m). |
| 49 | | ¹H NMR (400 MHz, DMSO-D₆) δ: 7.11 (1H, t, J = 7.2 Hz), 7.30-7.37 (3H, m), 7.45 (2H, d, J = 6.4 Hz), 7.69-7.72 (1H, m), 7.90 (1H, d, J = 2.0 Hz), 8.02-8.11 (2H, m), 8.19 (1H, s), 9.43 (1H, d, J = 4.0 Hz). |

TABLE 1-continued

| Example | Structural formula | ¹H NMR |
|---|---|---|
| 50 | | ¹H NMR (400 MHz, DMSO-D$_6$) δ: 7.11 (1H, t, J = 7.6 Hz), 7.30-7.36 (3H, m), 7.44 (2H, s), 7.70 (1H, dd, J = 2.8, 8.8 Hz), 7.89 (1H, d, J = 2.4 Hz), 8.81-8.82 (1H, m), 8.86 (1H, d, J = 2.4 Hz), 9.00 (1H, s). |
| 51 | | ¹H NMR (400 MHz, DMSO-D$_6$) δ: 7.10 (1H, t, J = 7.6 Hz), 7.28-7.33 (3H, m), 7.45 (2H, d, J = 7.6 Hz), 7.60-7.67 (3H, m), 7.88-7.92 (2H, m), 8.86 (2H, s). |
| 52 | | ¹H NMR (400 MHz, DMSO-D$_6$) δ: 7.11 (1H, t, J = 6.8 Hz), 7.31-7.36 (3H, m), 7.48 (2H, d, J = 8.0 Hz), 7.70 (1H, dd, J = 2.8, 8.8 Hz), 7.91 (1H, d, J = 2.0 Hz), 8.26 (1H, s), 9.04 (2H, s), 9.36 (1H, s). |
| 53 | | ¹H NMR (400 MHz, DMSO-D$_6$) δ: 7.36 (3H, d, J = 8.5 Hz), 7.53 (2H, d, J = 7.9 Hz), 7.64 (1H, dd, J = 7.6, 5.2 Hz), 7.70 (1H, dd, J = 8.9, 2.1 Hz), 7.89 (1H, s), 7.98 (1H, d, J = 7.9 Hz), 8.10 (1H, s), 8.70 (1H, s), 8.73 (1H, d, J = 4.3 Hz). |
| 54 | | ¹H NMR (400 MHz, DMSO-D$_6$) δ: 6.72 (1H, d, J = 7.6 Hz), 7.39-7.54 (7H, m), 7.74-7.76 (1H, m), 8.04 (1H, d, J = 2.4 Hz), 8.47 (1H, d, J = 6.0 Hz), 8.82 (1H, s). |

TABLE 1-continued

| Example | Structural formula | ¹H NMR |
|---|---|---|
| 55 | | ¹H NMR (400 MHz, CD$_3$OD) δ: 4.60 (1H, s), 7.24-7.26 (1H, m), 7.38-7.40 (2H, m), 7.48-7.53 (2H, m), 7.58-7.62 (2H, m), 7.72 (1H, dd, J = 2.4, 8.4 Hz), 8.11 (1H, d, J = 2.4 Hz), 8.93 (1H, d, J = 6.0 Hz), 9.12 (1H, d, J = 2.4 Hz). |
| 56 | | ¹H NMR (400 MHz, CD$_3$OD) δ: 7.89-7.93 (1H, m), 8.10-8.12 (3H, m), 8.16-8.18 (1H, m), 8.20-8.25 (1H, m), 8.27-8.33 (3H, m), 8.42-8.49 (2H, m), 8.58 (1H, s), 8.69 (1H, d, J = 2.8 Hz). |
| 57 | | ¹H NMR (400 MHz, CD$_3$OD) δ: 7.14-7.17 (1H, m), 7.31-7.35 (2H, m), 7.39 (1H, d, J = 8.8 Hz), 7.43-7.46 (2H, m), 7.63 (1H, dd, J = 2.4, 8.4 Hz), 7.88 (2H, d, J = 2.4 Hz), 7.14-7.17 (3H, m) |
| 58 | | ¹H NMR (400 MHz, DMSO-D$_6$) δ: 7.10 (1H, t, J = 6.8 Hz), 7.29-7.33 (3H, m), 7.46 (2H, d, J = 8.0 Hz), 7.67 (1H, dd, J = 2.4, 8.8 Hz), 7.79 (1H, t, J = 7.6 Hz), 7.87-7.89 (3H, m), 8.04 (1H, d, J = 8.0 Hz), 8.12 (1H, s). |
| 59 | | ¹H NMR (400 MHz, DMSO-D$_6$) δ: 4.61 (2H, d, J = 7.6 Hz), 5.35 (1H, t, J = 5.6 Hz), 7.06-7.10 (1H, m), 7.27-7.36 (4H, m), 7.40 (1H, s), 7.46-7.51 (4H, m), 7.56 (1H, t, J = 7.6 Hz), 7.67 (1H, dd, J = 2.4, 8.8 Hz), 7.88 (1H, d, J = 2.4 Hz) |

TABLE 1-continued

| Example | Structural formula | ¹H NMR |
|---|---|---|
| 60 | | ¹H NMR (400 MHz, DMSO-D$_6$) δ: 3.27 (3H, s), 7.11 (1H, t, J = 7.2 Hz), 7.29-7.33 (3H, m), 7.44-7.46 (2H, m), 7.67 (1H, dd, J = 2.8, 8.8 Hz), 7.87-7.89 (4H, m), 8.09-8.12 (2H, m). |
| 61 | | ¹H NMR (400 MHz, DMSO-D$_6$) δ: 2.94 (6H, s), 6.70-6.72 (1H, m), 6.82-6.83 (1H, m), 6.88 (1H, d, J = 2.0, 8.0 Hz), 7.08 (1H, t, J = 7.6 Hz), 7.28-7.41 (5H, m), 7.49 (2H, d, J = 7.6 Hz), 7.66 (1H, dd, J = 2.8, 8.8 Hz), 7.88 (1H, d, J = 2.4 Hz). |
| 62 | | ¹H NMR (400 MHz, DMSO-D$_6$) δ: 4.63 (2H, d, J = 5.6 Hz), 5.38 (1H, t, J = 5.6 Hz), 7.07 (1H, t, J = 7.2 Hz), 7.27-7.34 (3H, m), 7.42-7.47 (4H, m), 7.53 (3H, d, J = 8.4 Hz), 7.66 (1H, dd, J = 2.4, 8.8 Hz), 7.88 (1H, d, J = 2.4 Hz). |
| 63 | | ¹H NMR (400 MHz, DMSO-D$_6$) δ: 7.09 (1H, t, J = 7.2 Hz), 7.29 (2H, t, J = 7.6 Hz), 7.35 (1H, d, J = 8.8 Hz), 7.45 (2H, d, J = 8.0 Hz), 7.69 (1H, dd, J = 2.4, 8.8 Hz), 7.91-7.98 (3H, m), 8.30 (1H, d, J = 8.8 Hz), 8.38 (1H, s), 9.06 (2H, d, J = 9.2 Hz). |
| 64 | | ¹H NMR (400 MHz, CDCl$_3$) δ: 3.67 (3H, s), 6.76 (1H, s), 6.88 (1H, dd, J = 7.9, 4.9 Hz), 7.31-7.36 (2H, m), 7.44 (1H, d, J = 9.2 Hz), 7.51-7.65 (4H, m), 7.72 (1H, dd, J = 5.2, 1.5 Hz), 8.08 (1H, d, J = 2.4 Hz), 8.88 (1H, dd, J = 7.9, 1.2 Hz). |

TABLE 1-continued

| Example | Structural formula | ¹H NMR |
|---|---|---|
| 65 | (6-chloro-3-(2-fluorophenyl)-2-(phenylamino)quinazolin-4(3H)-one) | ¹H NMR (400 MHz, DMSO-D₆) δ: 7.11 (1H, t, J = 7.6 Hz), 7.30-7.35 (3H, m), 7.40-7.52 (4H, m), 7.61-7.66 (2H, m), 7.69 (1H, dd, J = 2.4 Hz, 8.8 Hz), 7.90 (1H, d, J = 2.4 Hz), 8.16 (1H, s). |
| 66 | (6-chloro-2-((2-chloro-4-fluorophenyl)amino)-3-(pyridazin-4-yl)quinazolin-4(3H)-one) | ¹H NMR (400 MHz, DMSO-D₆) δ: 6.90-7.20 (1H, m), 7.20-7.57 (3H, m), 7.60-7.75 (1H, m), 7.81-7.98 (2H, m), 8.15 (1H, d, J = 77.5 Hz), 9.31-9.60 (2H, m). |
| 67 | (6-chloro-3-(2-chlorophenyl)-2-(phenylamino)quinazolin-4(3H)-one) | ¹H NMR (400 MHz, DMSO-D₆) δ: 7.11 (1H, t, J = 6.8 Hz), 7.29-7.33 (3H, m), 7.42 (2H, d, J = 7.6 Hz), 7.55-7.61 (2H, m), 7.66-7.70 (2H, m), 7.74 (1H, dd, J = 1.6 Hz, 8.8 Hz), 7.88 (1H, d, J = 2.4 Hz), 8.01 (1H, s). |
| 68 | (6-chloro-3-(2-methoxyphenyl)-2-(phenylamino)quinazolin-4(3H)-one) | ¹H NMR (400 MHz, CDCl₃) δ: 3.83 (3H, s), 7.09-7.13 (1H, m), 7.17-7.24 (2H, m), 7.31-7.38 (3H, m), 7.46-7.52 (3H, m), 7.57-7.62 (2H, m), 8.14 (1H, d, J = 2.0 Hz). |
| 69 | (6-chloro-3-(2-methylphenyl)-2-(phenylamino)quinazolin-4(3H)-one) | ¹H NMR (400 MHz, CDCl₃) δ: 2.22 (3H, s), 5.97 (1H, s), 7.11-7.14 (1H, m), 7.32-7.36 (3H, m), 7.48-7.62 (7H, m), 8.15 (1H, d, J = 2.0 Hz). |

TABLE 1-continued

| Example | Structural formula | ¹H NMR |
|---|---|---|
| 70 | | ¹H NMR (400 MHz, CDCl₃) δ: 6.74 (1H, t, J = 4.3 Hz), 7.31-7.35 (1H, m), 7.39-7.47 (2H, m), 7.56 (1H, d, J = 2.4 Hz), 7.57-7.64 (3H, m), 7.95 (1H, d, J = 3.1 Hz), 8.09 (1H, d, J = 2.4 Hz), 8.59 (1H, dd, J = 9.5, 4.0 Hz). |
| 71 | | ¹H NMR (400 MHz, CDCl₃) δ: 6.74 (1H, t, J = 4.3 Hz), 7.31-7.35 (2H, m), 7.39-7.47 (2H, m), 7.56 (1H, d, J = 2.4 Hz), 7.57-7.64 (3H, m), 7.95 (1H, d, J = 3.1 Hz), 8.09 (1H, d, J = 2.4 Hz), 8.59 (1H, dd, J = 9.5, 4.0 Hz). |
| 72 | | ¹H NMR (400 MHz, CDCl₃) δ: 5.56 (1H, s), 7.16 (1H, t, J = 7.3 Hz), 7.33 (2H, t, J = 7.9 Hz), 7.40 (2H, d, J = 7.9 Hz), 7.45 (1H, d, J = 8.5 Hz), 7.62 (1H, dd, J = 9.1, 2.4 Hz), 8.07 (1H, t, J = 1.8 Hz), 8.09 (1H, d, J = 2.4 Hz), 8.88 (1H, d, J = 1.8 Hz), 9.06 (1H, d, J = 1.8 Hz). |
| 73 | | ¹H NMR (400 MHz, CDCl₃) δ: 6.70 (2H, d, J = 8.5 Hz), 7.21-7.25 (3H, m), 7.37 (1H, dd, J = 8.5, 2.4 Hz), 7.43-7.52 (4H, m), 8.02 (1H, d, J = 2.4 Hz), 9.87 (1H, s). |

TABLE 1-continued

| Example | Structural formula | ¹H NMR |
|---|---|---|
| 74 | | ¹H NMR (400 MHz, CDCl₃) δ: 5.58 (1H, s), 7.08-7.13 (1H, m), 7.25-7.32 (2H, m), 7.35-7.39 (2H, m), 7.40 (1H, d, J = 9.2 Hz), 7.56 (1H, dd, J = 8.9, 2.8 Hz), 8.00 (1H, t, J = 2.1 Hz), 8.04 (1H, d, J = 2.4 Hz), 8.83 (1H, d, J = 2.4 Hz), 9.04 (1H, d, J = 1.2 Hz). |
| 75 | | ¹H NMR (400 MHz, CDCl₃) δ: 5.71 (1H, s), 7.11-7.17 (1H, m), 7.30-7.36 (2H, m), 7.42-7.46 (3H, m), 7.56 (1H, td, J = 5.2, 2.6 Hz), 7.60 (1H, dd, J = 9.1, 2.4 Hz), 8.09 (1H, d, J = 2.4 Hz), 8.54 (1H, d, J = 1.8 Hz), 8.73 (1H, d, J = 2.4 Hz). |
| 76 | | ¹H NMR (400 MHz, CDCl₃) δ: 1.34 (3H, t, J = 7.6 Hz), 2.92 (2H, q, J = 7.6 Hz), 5.82 (1H, s), 7.03-7.09 (1H, m), 7.23-7.29 (2H, m), 7.36-7.44 (4H, m), 7.53 (1H, dd, J = 8.6, 2.4 Hz), 7.62 (1H, dd, J = 7.9, 2.4 Hz), 8.04 (1H, d, J = 2.4 Hz), 8.52 (1H, d, J = 2.4 Hz). |
| 77 | | ¹H NMR (400 MHz, CDCl₃) δ: 1.33 (6H, d, J = 6.7 Hz), 3.12-3.19 (1H, m), 5.78 (1H, s), 7.04-7.10 (1H, m), 7.24-7.30 (2H, m), 7.36-7.43 (4H, m), 7.53 (1H, dd, J = 8.6, 2.4 Hz), 7.62 (1H, dd, J = 7.9, 2.4 Hz), 8.04 (1H, d, J = 2.4 Hz), 8.53 (1H, d, J = 1.8 Hz). |

TABLE 1-continued
| Example | Structural formula | ¹H NMR |
|---|---|---|
| 78 | 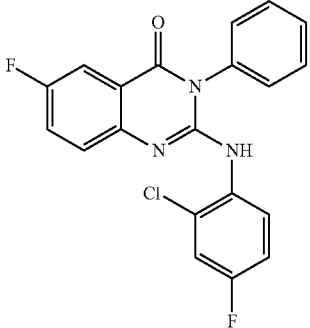 [SMILES: O=c1c2cc(F)ccc2nc(Nc2ccc(F)cc2Cl)n1-c1ccccc1] | ¹H NMR (400 MHz, CDCl₃) δ: 6.59 (1H, s), 7.06-7.11 (2H, m), 7.40-7.72 (8H, m), 7.84-7.87 (1H, m), 8.68-8.72 (1H, m). |
| 79 | 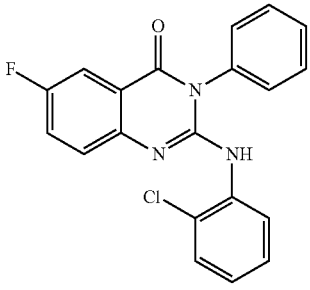 [SMILES: O=c1c2cc(F)ccc2nc(Nc2ccccc2Cl)n1-c1ccccc1] | ¹H NMR (400 MHz, CDCl₃) δ: 6.79 (1H, s), 6.98-7.03 (1H, m), 7.27-7.46 (5H, m), 7.56-7.72 (4H, m), 7.84-7.87 (1H, m), 8.78 (1H, d, J = 8.4 Hz). |
| 80 | 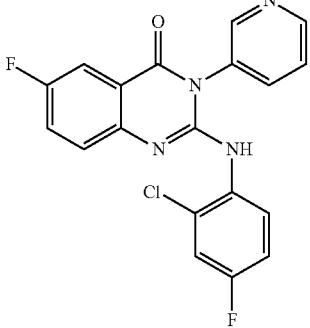 | ¹H NMR (400 MHz, DMSO-D₆) δ: 7.20-7.34 (2H, m), 7.42-7.73 (5H, m), 7.80-7.88 (1H, m), 7.95-8.06 (1H, m), 8.64-8.79 (2H, m). |
| 81 | 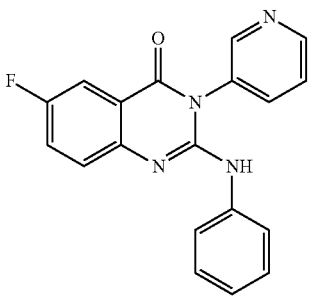 [SMILES: O=c1c2cc(F)ccc2nc(Nc2ccccc2)n1-c1cccnc1] | ¹H NMR (400 MHz, CDCl₃) δ: 5.73 (1H, s), 7.11-7.15 (1H, m), 7.32-7.36 (2H, m), 7.39-7.44 (1H, m), 7.46-7.48 (2H, m), 7.52 (1H, dd, JJ = 4.8 Hz, 9.2 Hz), 7.61-7.64 (1H, m), 7.79-7.82 (2H, m), 8.72 (1H, d, JJ = 2.4 Hz), 8.87 (1H, dd, JJ = 1.6 Hz, 4.8 Hz). |

TABLE 1-continued

| Example | Structural formula | ¹H NMR |
|---|---|---|
| 82 | | ¹H NMR (400 MHz, DMSO-D$_6$) δ: 7.35 (2H, d, J = 9.1 Hz), 7.40 (2H, dd, J = 9.1, 4.9 Hz), 7.45-7.62 (4H, m), 7.65 (1H, dd, J = 8.5, 3.0 Hz), 7.67-7.79 (1H, m), 8.00 (2H, d, J = 7.9 Hz). |
| 83 | | ¹H NMR (400 MHz, DMSO-D$_6$) δ: 7.08 (1H, t, J = 7.3 Hz), 7.30 (2H, t, J = 7.9 Hz), 7.46-7.72 (10H, m). |
| 84 | | ¹H NMR (400 MHz, DMSO-D$_6$) δ: 3.90 (3H, s), 7.03 (1H, t, J = 7.3 Hz), 7.21 (2H, td, J = 9.5, 2.6 Hz), 7.24-7.33 (3H, m), 7.47-7.50 (2H, m), 7.54-7.65 (5H, m). |
| 85 | | ¹H NMR (400 MHz, CDCl$_3$) δ: 2.41 (3H, s), 5.71 (1H, s), 7.06 (1H, t, J = 7.3 Hz), 7.24-7.29 (2H, m), 7.32-7.49 (5H, m), 7.63 (1H, dd, J = 7.9, 1.8 Hz), 7.74 (1H, dd, J = 7.9, 3.1 Hz), 8.68 (1H, dd, J = 4.6, 1.5 Hz). |
| 86 | | ¹H NMR (400 MHz, CDCl$_3$) δ: 7.04-7.12 (1H, m), 7.24-7.30 (2H, m), 7.33-7.39 (3H, m), 7.43-7.51 (2H, m), 7.72 (1H, d, J = 3.1 Hz), 7.74 (1H, d, J = 3.1 Hz), 8.47 (1H, s), 8.65 (1H, d, J = 2.4 Hz). |

TABLE 1-continued

| Example | Structural formula | ¹H NMR |
|---|---|---|
| 87 | (6-fluoro-3-(5-methoxypyridin-3-yl)-2-(phenylamino)quinazolin-4(3H)-one) | ¹H NMR (400 MHz, CDCl₃) δ: 3.87 (3H, s), 7.05 (1H, t, J = 7.3 Hz), 7.16-7.32 (4H, m), 7.32-7.49 (4H, m), 7.72 (1H, dd, J = 8.3, 2.8 Hz), 8.20 (1H, s), 8.41 (1H, s). |
| 88 | (6-fluoro-2-(phenylamino)-3-(5-(trifluoromethyl)pyridin-3-yl)quinazolin-4(3H)-one) | ¹H NMR (400 MHz, CDCl₃) δ: 6.98-7.03 (1H, m), 7.14-7.24 (4H, m), 7.30 (1H, td, J = 8.3, 2.8 Hz), 7.35-7.50 (2H, m), 7.65 (1H, dd, J = 8.3, 2.8 Hz), 7.86 (1H, s), 8.71 (1H, d, J = 2.4 Hz), 8.91 (1H, s). |
| 89 | (6-fluoro-3-(6-methylpyridin-3-yl)-2-(phenylamino)quinazolin-4(3H)-one) | ¹H NMR (400 MHz, CDCl₃) δ: 2.64 (3H, s), 5.79 (1H, s), 7.02-7.08 (1H, m), 7.23-7.29 (2H, m), 7.33 (1H, td, J = 8.5, 3.1 Hz), 7.37-7.47 (4H, m), 7.59 (1H, dd, J = 7.9, 2.4 Hz), 7.72 (1H, dd, J = 8.2, 2.7 Hz), 8.50 (1H, d, J = 2.4 Hz). |
| 90 | (6-fluoro-3-(2-methoxypyridin-3-yl)-2-(phenylamino)quinazolin-4(3H)-one) | ¹H NMR (400 MHz, CDCl₃) δ: 3.68 (3H, s), 6.88 (1H, dd, J = 7.6, 5.2 Hz), 7.30-7.39 (4H, m), 7.50 (1H, dd, J = 8.9, 4.6 Hz), 7.53-7.64 (4H, m), 7.72 (1H, dd, J = 5.2, 1.5 Hz), 7.77 (1H, dd, J = 8.6, 3.1 Hz), 8.86 (1H, d, J = 6.7 Hz). |

TABLE 1-continued

| Example | Structural formula | ¹H NMR |
|---|---|---|
| 91 | | ¹H NMR (400 MHz, DMSO-D$_6$) δ: 4.45 (2H, d, J = 5.5 Hz), 5.11 (1H, t, J = 5.8 Hz), 7.23 (2H, d, J = 7.9 Hz), 7.33-7.44 (4H, m), 7.50 (2H, d, J = 6.7 Hz), 7.52-7.67 (5H, m). |
| 92 | | ¹H NMR (400 MHz, DMSO-D$_6$) δ: 4.47 (2H, d, J = 5.5 Hz), 5.29 (1H, t, J = 5.8 Hz), 7.20 (1H, s), 7.30 (1H, d, J = 8.5 Hz), 7.37 (1H, d, J = 1.2 Hz), 7.45 (1H, dd, J = 9.1, 4.9 Hz), 7.53-7.72 (7H, m), 8.11 (1H, d, J = 7.9 Hz). |
| 93 | | ¹H NMR (400 MHz, CDCl$_3$) δ: 5.93 (1H, br s), 7.06-7.11 (1H, m), 7.27 (2H, t, J = 7.9 Hz), 7.32-7.39 (3H, m), 7.45 (1H, dd, J = 9.2, 4.9 Hz), 7.70-7.75 (2H, m), 8.51 (1H, s), 8.71 (1H, s). |
| 94 | | ¹H NMR (400 MHz, CDCl$_3$) δ: 2.20 (3H, s), 5.85 (1H, s), 7.05 (1H, t, J = 7.3 Hz), 7.25 (2H, t, J = 7.9 Hz), 7.35 (1H, td, J = 8.6, 3.1 Hz), 7.40 (3H, t, J = 7.0 Hz), 7.45 (1H, dd, J = 8.9, 4.6 Hz), 7.73 (1H, dd, J = 8.6, 3.1 Hz), 8.48 (1H, s), 8.60 (1H, d, J = 4.9 Hz). |

TABLE 1-continued

| Example | Structural formula | ¹H NMR |
|---|---|---|
| 95 | | ¹H NMR (400 MHz, CDCl₃) δ: 1.28 (3H, t, J = 7.6 Hz), 2.75 (2H, q, J = 7.6 Hz), 5.80 (1H, s), 7.06 (1H, t, J = 7.3 Hz), 7.26 (2H, t, J = 7.6 Hz), 7.34 (1H, td, J = 8.6, 3.1 Hz), 7.41 (2H, d, J = 7.9 Hz), 7.45 (1H, dd, J = 9.2, 4.9 Hz), 7.56 (1H, s), 7.73 (1H, dd, J = 8.6, 3.1 Hz), 8.46 (1H, s), 8.63 (1H, s). |
| 96 | | ¹H NMR (400 MHz, DMSO-D₆) δ: 7.10 (1H, t, J = 7.3 Hz), 7.32 (2H, t, J = 7.6 Hz), 7.40 (1H, dd, J = 8.8, 5.2 Hz), 7.47 (2H, d, J = 7.9 Hz), 7.59 (1H, td, J = 8.8, 2.8 Hz), 7.66 (1H, dd, J = 8.5, 3.0 Hz), 8.03 (1H, s), 8.10 (1H, s), 9.47 (1H, s), 9.51 (1H, d, J = 5.5 Hz). |
| 97 | | ¹H NMR (400 MHz, CDCl₃) δ: 1.35 (3H, t, J = 7.6 Hz), 2.92 (2H, q, J = 7.6 Hz), 5.77 (1H, s), 7.06 (1H, t, J = 7.3 Hz), 7.26 (2H, t, J = 7.9 Hz), 7.33 (1H, td, J = 8.5, 3.1 Hz), 7.37-7.47 (4H, m), 7.62 (1H, dd, J = 8.2, 2.7 Hz), 7.73 (1H, dd, J = 8.5, 3.1 Hz), 8.53 (1H, d, J = 2.4 Hz). |
| 98 | | ¹H NMR (400 MHz, DMSO-D₆) δ: 3.16 (3H, s), 7.47-7.52 (3H, m), 7.53-7.70 (5H, m), 7.80 (4H, s), 7.97 (1H, s). |
| 99 | | ¹H NMR (400 MHz, CDCl₃) δ: 7.09-7.15 (1H, m), 7.18 (1H, s), 7.31-7.37 (2H, m), 7.41 (1H, td, J = 8.5, 3.1 Hz), 7.44-7.53 (3H, m), 7.83 (1H, dd, J = 8.2, 2.7 Hz), 8.71-8.73 (1H, m), 8.77 (1H, d, J = 2.4 Hz), 8.91 (1H, d, J = 1.2 Hz). |

TABLE 1-continued

| Example | Structural formula | ¹H NMR |
|---|---|---|
| 100 | | ¹H NMR (400 MHz, DMSO-D₆) δ: 2.11 (6H, s), 3.31 (2H, d, J = 4.6 Hz), 7.18 (2H, d, J = 8.7 Hz), 7.33-7.43 (4H, m), 7.48 (2H, d, J = 7.3 Hz), 7.51-7.66 (5H, m). |
| 101 | | ¹H NMR (400 MHz, DMSO-D₆) δ: 1.37 (2H, d, J = 5.0 Hz), 1.41-1.52 (4H, m), 2.28 (4H, s), 3.33 (2H, d, J = 18.7 Hz), 7.18 (2H, d, J = 8.2 Hz), 7.31-7.43 (4H, m), 7.48 (2H, d, J = 6.9 Hz), 7.51-7.66 (5H, m). |
| 102 | | ¹H NMR (400 MHz, DMSO-D₆) δ: 2.29-2.35 (4H, m), 3.40 (2H, s), 3.55 (4H, t, J = 4.6 Hz), 7.20 (2H, d, J = 8.5 Hz), 7.32-7.44 (4H, m), 7.48 (2H, d, J = 6.7 Hz), 7.51-7.66 (5H, m). |
| 103 | | ¹H NMR (400 MHz, DMSO-D₆) δ: 1.91-1.98 (2H, m), 3.07 (4H, t, J = 7.0 Hz), 3.44 (2H, s), 7.15 (2H, d, J = 8.5 Hz), 7.32-7.41 (4H, m), 7.48 (2H, d, J = 6.7 Hz), 7.51-7.66 (5H, m). |
| 104 | | ¹H NMR (400 MHz, DMSO-D₆) δ: 1.00 (3H, t, J = 7.0 Hz), 2.07 (3H, s), 2.35 (2H, q, J = 7.0 Hz), 3.38 (2H, s), 7.18 (2H, d, J = 7.8 Hz), 7.32-7.44 (4H, m), 7.48 (2H, d, J = 6.9 Hz), 7.51-7.67 (5H, m). |
| 105 | | ¹H NMR (400 MHz, DMSO-D₆) δ: 0.95 (6H, t, J = 7.2 Hz), 2.42 (4H, q, J = 7.2 Hz), 3.46 (2H, s), 7.20 (2H, d, J = 8.2 Hz), 7.32-7.43 (4H, m), 7.48 (2H, d, J = 7.3 Hz), 7.51-7.66 (5H, m). |
| 106 | | ¹H NMR (400 MHz, DMSO-D₆) δ: 2.67 (3H, d, J = 5.0 Hz), 3.07-3.26 (3H, m), 3.71 (2H, t, J = 5.0 Hz), 4.25 (2H, ddd, J = 39.7, 13.0, 5.0 Hz), 7.43-7.53 (5H, m), 7.53-7.64 (6H, m), 7.66 (1H, dd, J = 8.7, 2.7 Hz), 10.43 (1H, s). |

TABLE 1-continued

| Example | Structural formula | ¹H NMR |
|---|---|---|
| 107 | | ¹H NMR (400 MHz, DMSO-D₆) δ: 4.95 (4H, s), 7.21 (1H, d, J = 7.9 Hz), 7.31-7.40 (2H, m), 7.41 (1H, d, J = 1.8 Hz), 7.43-7.51 (3H, m), 7.51-7.66 (4H, m). |
| 108 | | ¹H NMR (400 MHz, DMSO-D₆) δ: 3.55 (4H, t, J = 12.6 Hz), 3.65 (2H, s), 7.20 (2H, d, J = 8.7 Hz), 7.35-7.45 (4H, m), 7.48 (2H, d, J = 6.9 Hz), 7.51-7.66 (5H, m). |
| 109 | | ¹H NMR (400 MHz, DMSO-D₆) δ: 1.15 (6H, s), 2.85 (4H, s), 3.48 (2H, s), 7.15 (2H, d, J = 8.2 Hz), 7.32-7.40 (4H, m), 7.46-7.51 (2H, m), 7.51-7.66 (5H, m). |
| 110 | | ¹H NMR (400 MHz, DMSO-D₆) δ: 2.71 (2H, td, J = 6.0, 2.1 Hz), 3.43 (2H, td, J = 6.0, 2.1 Hz), 3.47 (2H, s), 4.15 (1H, q, J = 6.2 Hz), 5.25 (1H, d, J = 6.4 Hz), 7.15 (2H, d, J = 8.7 Hz), 7.34-7.41 (4H, m), 7.46-7.50 (2H, m), 7.51-7.64 (5H, m). |
| 111 | | ¹H NMR (400 MHz, DMSO-D₆) δ: 1.33 (3H, s), 2.84 (2H, d, J = 7.8 Hz), 3.12 (2H, dd, J = 5.9, 1.8 Hz), 3.50 (2H, s), 5.10 (1H, s), 7.15 (2H, d, J = 8.2 Hz), 7.34-7.41 (4H, m), 7.46-7.50 (2H, m), 7.51-7.65 (5H, m). |
| 112 | | ¹H NMR (400 MHz, CDCl₃) δ: 3.38 (3H, s), 4.51 (2H, s), 5.93 (1H, s), 7.07 (1H, t, J = 7.3 Hz), 7.29 (2H, t, J = 7.9 Hz), 7.40 (2H, d, J = 7.3 Hz), 7.49 (3H, d, J = 7.3 Hz), 7.53 (3H, s), 7.56-7.69 (4H, m), 8.09 (1H, d, J = 1.2 Hz). |

TABLE 1-continued

| Example | Structural formula | ¹H NMR |
|---|---|---|
| 113 | | ¹H NMR (400 MHz, CDCl₃) δ: 5.97 (1H, s), 7.10-7.14 (1H, m), 7.25-7.27 (1H, m), 7.31-7.35 (2H, m), 7.42-7.53 (6H, m), 7.60-7.69 (3H, m). |
| 114 | | ¹H NMR (400 MHz, CDCl₃) δ: 3.89 (3H, s), 5.89 (1H, s), 7.07-7.10 (1H, m), 7.29-7.34 (3H, m), 7.42-7.52 (5H, m), 7.58-7.71 (3H, m). |
| 115 | | ¹H NMR (400 MHz, CDCl₃) δ: 6.13 (1H, s), 7.09-7.13 (1H, m), 7.18-7.21 (1H, m), 7.33-7.37 (2H, m), 7.41-7.44 (2H, m), 7.63-7.72 (5H, m), 7.78-7.80 (1H, m), 8.10-8.12 (1H, m). |
| 116 | | ¹H NMR (400 MHz, CDCl₃) δ: 3.90 (3H, s), 6.55 (1H, s), 7.05-7.10 (2H, m), 7.31-7.34 (1H, m), 7.44-7.53 (3H, m), 7.60-7.70 (4H, m), 8.73-8.77 (1H, m). |
| 117 | | ¹H NMR (400 MHz, CDCl₃) δ: 3.91 (3H, s), 6.74 (1H, s), 6.96-7.00 (1H, m), 7.27-7.29 (1H, m), 7.32-7.36 (2H, m), 7.44-7.46 (2H, m), 7.53-7.55 (1H, m), 7.61-7.71 (4H, m), 8.81-8.83 (1H, m) |

TABLE 1-continued

| Example | Structural formula | ¹H NMR |
|---|---|---|
| 118 | | ¹H NMR (400 MHz, CDCl₃) δ: 2.46 (3H, s), 6.57 (1H, s), 7.04-7.10 (2H, m), 7.44-7.70 (7H, m), 8.00 (1H, s), 8.75-8.79 (1H, m). |
| 119 | | ¹H NMR (400 MHz, CDCl₃) δ: 2.46 (3H, s), 6.77 (1H, s), 6.97-7.01 (1H, m), 7.27-7.29 (1H, m), 7.32-7.36 (1H, m), 7.44-7.70 (7H, m), 8.01 (1H, s), 8.84 (1H, d, J = 8.4 Hz)). |
| 120 | | ¹H NMR (400 MHz, CDCl₃) δ: 6.59 (1H, s), 7.06-7.09 (2H, m), 7.29-7.31 (1H, m), 7.44-7.46 (3H, m), 7.51-7.70 (4H, m), 8.65-8.69 (1H, m). |
| 121 | | ¹H NMR (400 MHz, CDCl₃) δ: 6.80 (1H, s), 7.00-7.04 (1H, m), 7.28-7.36 (3H, m), 7.44-7.70 (7H, m), 8.75 (1H, d, J = 8.0 Hz). |

TABLE 1-continued

| Example | Structural formula | ¹H NMR |
|---|---|---|
| 122 | | ¹H NMR (400 MHz, CDCl₃) δ: 6.61 (1H, s), 7.06-7.11 (2H, m), 7.30-7.33 (1H, m), 7.45-7.47 (2H, m), 7.54-7.56 (1H, m), 7.61-7.73 (4H, m), 8.22 (1H, d, J = 8.8 Hz), 8.74 8.80 (1H, m). |
| 123 | | ¹H NMR (400 MHz, CDCl₃) δ: 6.81 (s, 1H), 6.98-7.02 (m, 1H), 7.27-7.37 (m, 3H), 7.45-7.47 (m, 2H), 7.56-7.73 (m, 5H), 8.22 (d, J = 9.2 Hz, 1H), 8.83 8.85 (m, 1H). |
| 124 | | ¹H NMR (400 MHz, CDCl₃) δ: 3.88 (3H, s), 5.67 (1H, s), 7.08-7.12 (1H, m), 7.30-7.34 (3H, m), 7.47-7.49 (3H, m), 7.55 (1H, d, J = 3.2 Hz), 7.60-7.63 (1H, m), 7.79-7.82 (1H, m), 8.71 (1H, d, J = 2.4 Hz), 8.85 (1H, dd, J = 1.6 Hz, 4.4 Hz). |
| 125 | | ¹H NMR (400 MHz, CDCl₃) δ: 2.44 (3H, s), 5.69 (1H, s), 7.09-7.13 (1H, m), 7.30-7.34 (2H, m), 7.44-7.52 (4H, m), 7.59-7.63 (1H, m), 7.78-7.81 (1H, m), 7.96 (1H, s), 8.71 (1H, d, J = 1.6 Hz), 8.85 (1H, dd, J = 1.2 Hz, 4.4 Hz). |
| 126 | | ¹H NMR (400 MHz, DMSO-D₆) δ: 3.23 (3H, s), 7.12 (1H, t, J = 7.3 Hz), 7.32 (2H, t, J = 7.9 Hz), 7.44 (3H, t, J = 7.6 Hz), 7.52 (2H, d, J = 7.3 Hz), 7.55-7.66 (3H, m), 7.88 (1H, s), 8.06 (1H, dd, J = 8.8, 2.1 Hz), 8.40 (1H, d, J = 2.4 Hz). |

TABLE 1-continued

| Example | Structural formula | ¹H NMR |
|---|---|---|
| 128 | | ¹H NMR (400 MHz, CDCl₃) δ: 6.23 (1H, d, J = 6.1 Hz), 7.17-7.28 (4H, m), 7.46-7.58 (3H, m), 7.78 (1H, dd, J = 8.5, 3.0 Hz), 8.31 (1H, d, J = 6.1 Hz), 8.91 (1H, s), 14.03 (1H, br s). |
| 129 | | ¹H NMR (400 MHz, CDCl₃) δ: 6.88 (1H, s), 7.05-7.16 (2H, m), 7.22-7.26 (1H, m), 7.43-7.45 (2H, m), 7.63-7.73 (3H, m), 7.81 (1H, d, J = 8.8 Hz), 8.14 (1H, d, J = 9.2 Hz), 9.13-9.17 (1H, m). |
| 130 | | ¹H NMR (400 MHz, CDCl₃) δ: 7.00-7.06 (2H, m), 7.22-7.30 (2H, m), 7.38-7.46 (3H, m), 7.63-7.73 (3H, m), 7.81 (1H, d, J - 8.0 Hz), 8.14 (1H, d, J = 11.2 Hz), 9.17 (1H, d, J = 9.6 Hz). |
| 131 | ·HCOOH | ¹H NMR (400 MHz, DMSO-D₆) δ: 2.86 (6H, s), 6.66 (2H, d, J = 9.2 Hz), 7.17-7.24 (3H, m), 7.31 (1H, s), 7.46-7.48 (2H, m), 7.54-7.62 (4H, m), 7.84 (1H, d, J= 2.8 Hz). |
| 132 | | ¹H NMR (400 MHz, DMSO-D₆) δ: 7.45 (1H, d, J = 8.5 Hz), 7.59-7.68 (1H, m), 7.69-7.80 (5H, m), 7.93 (1H, s), 7.98 (1H, d, J = 8.5 Hz), 8.40 (1H, s), 8.72 (2H, d, J = 9.8 Hz). |

TABLE 1-continued

| Example | Structural formula | ¹H NMR |
|---|---|---|
| 133 | | ¹H NMR (400 MHz, CDCl₃) δ: 2.69 (3H, s), 7.13 (1H, t, J = 7.3 Hz), 7.32-7.37 (2H, m), 7.43 (1H, d, J = 8.7 Hz), 7.48-7.52 (3H, m), 7.60 (1H, dd, J = 8.7, 2.3 Hz), 8.10 (1H, s), 8.12 (1H, d, J = 2.8 Hz), 9.25 (1H, d, J = 0.9 Hz). |
| 134 | | ¹H NMR (400 MHz, DMSO-D₆) δ: 3.24 (4H, s), 3,42 (2H, s), 4.58 (4H, s), 7.13 (2H, d, J = 8.2 Hz), 7.34-7.40 (4H, m), 7.46-7.50 (2H, m), 7.51-7.64 (5H, m). |
| 135 | | ¹H NMR (400 MHz, CDCl₃) δ: 5.75 (1H, s), 7.12-7.16 (1H, m), 7.27 (1H, dd, J = 1.2 Hz, 10.8 Hz), 7.32-7.36 (2H, m), 7.42-7.54 (4H, m), 7.61 (1H, dd, J = 4.8 Hz, Hz, 8.0 Hz), 7.79-7.82 (1H, m), 8.71 (1H, d, J = 2.4 Hz), 8.85 (1H, dd, J = 1.6 Hz, 4.8 Hz). |
| 136 | | ¹H NMR (400 MHz, CDCl₃) δ: 5.75 (1H, s), 7.12-7.16 (1H, m), 7.27 (1H, dd, J = 1.2 Hz, 10.8 Hz), 7.32-7.36 (2H, m), 7.42-7.54 (4H, m), 7.61 (1H, dd, J = 4.8 Hz, Hz, 8.0 Hz), 7.79-7.82 (1H, m), 8.71 (1H, d, J = 2.4 Hz), 8.85 (1H, dd, J = 1.6 Hz, 4.8 Hz). |
| 127 | | ¹H NMR (400 MHz, CDCl₃) δ: 6.80 (1H, s), 7.00-7.04 (1H, m), 7.28-7.36 (3H, m), 7.44-7.70 (7H, m), 8.75 (1H, d, J = 8.0 Hz). |

TABLE 1-continued

| Example | Structural formula | ¹H NMR |
|---|---|---|
| 137 | | ¹H NMR (400 MHz, DMSO-D$_6$) δ: 4.45 (2H, d, J = 5.6 Hz), 5.11 (1H, t, J = 5.8 Hz), 7.24-7.20 (3H, m), 7.30 (1H, d, J = 8.4 Hz) 7.34 (1H, s), 7.48 (2H, d, J = 8.8 Hz), 7.67-7.55 (4H, m), 7.95 (1H, d, J = 7.6 Hz). |
| 138 | | ¹H NMR (400 MHz, DMSO-D$_6$) δ: 4.45 (2H, d, J = 6.0 Hz), 5.14 (1H, t, J = 5.8 Hz), 7.01 (1H, d, J = 8.0 Hz), 7.26-7.21 (2H, m), 7.35-7.31 (3H, m), 7.49-7.45 (3H, m), 7.68-7.55 (4H, m), 7.97 (1H, dd, J = 8.2 Hz, 1.2 Hz). |
| 139 | | ¹H NMR (400 MHz, DMSO-D$_6$) δ: 2.12 (6H, s), 3.17 (2H, J = 5.2 Hz), 7.25-7.18 (3H, m), 7.33 (2H, d, J = 8.8 Hz), 7.46 (4H, dd, J = 81.8 Hz, 7.2 Hz), 7.68-7.54 (4H, m), 7.96 (1H, d, J = 7.6 Hz). |
| 140 | | ¹H NMR (400 MHz, DMSO-D$_6$) δ: 1.95 (2H, t, J = 7.0 Hz), 3.08 (4H, t, J = 6.8 Hz), 3.44 (2H, s), 7.16 (2H, d, J = 8.0 Hz), 7.22 (2H, t, J = 8.4 Hz), 7.47 (2H, d, J = 7.2 Hz), 7.60-7.55 (3H, m), 7.65 (1H, d, J = 7.8 Hz), 7.96 (1H, d, J = 7.6 Hz). |
| 141 | | ¹H NMR (400 MHz, DMSO-D$_6$) δ: 4.45 (2 H, d, J = 5.6 Hz), 5.12 (1 H, t, J = 5.6 Hz) ,7.25-7.21 (3 H, m), 7.30 (1 H, d, J = 8.0 Hz), 7.41 (2 H, d, J = 8.8 Hz), 7.60 (1 H, dd, J = 7.6 Hz, 5.2 Hz), 7.69-7.694 (2H, m), 7.80 (1H, s), 7.95 (1H, d, J = 8.0 Hz), 8.09 (1H, t, J = 8.8 Hz), 8.70 (1H, d, J = 6.0 Hz). |
| 142 | | ¹H NMR (400 MHz, DMSO-D$_6$) δ: 4.46 (2H, d, J = 6.0 Hz), 5.12 (1H, t, J = 5.6 Hz), 7.25-7.20 (3H, m), 7.29 (1H, d, J = 7.6 Hz), 7.42 (2H, d, J = 8.4 Hz), 7.68-7.61 (2H, m), 7.85 (1H, s), 7.99-7.94 (2H, m), 8.69 (1H, d, J = 2.0 Hz), 8.72 (1H, dd, J = 5.2 Hz, 1.6 Hz). |

TABLE 1-continued

| Example | Structural formula | ¹H NMR |
|---|---|---|
| 143 | | ¹H NMR (400 MHz, DMSO-D₆) δ: 7.96 (1H, d, J = 9.2 Hz), 7.66 (1H, t, J = 8.4 Hz), 7.60 (2H, d, J = 7.6 Hz), 7.56 (1H, d, J = 6.8 Hz), 7.49-7.44 (3H, m), 7.42 (1H, s), 7.36 (1H, s), 7.29 (1H, d, J = 8.0 Hz), 7.23 (2H, t, J = 7.6 Hz), 6.97 (1H, d, J = 7.6 Hz), 3.37 (2H, s), 2.14 (6H, s). |
| 144 | | ¹H NMR (400 MHz, DMSO-D₆) δ: 2.12 (6H, s), 3.31 (2H, s), 7.25-7.17 (3H, m), 7.32 (1H, d, J = 8.0 Hz), 7.42 (2H, d, J = 8.0 Hz), 7.60 (1H, dd, J = 7.6 Hz, 6.0 Hz), 7.69-7.65 (2H, m), 7.79 (1H, s), 7.96 (1H, d, J = 8.0 Hz), 8.08 (1H, t, J = 8.6 Hz), 8.70 (1H, d, J = 4.8 Hz). |
| 145 | | ¹H NMR (400 MHz, DMSO-D₆) δ: 1.97-1.93 (2H, m), 3.09 (4H, t, J = 7.0 Hz), 3.46 (2H, s), 7.17 (2H, d, J = 8.0 Hz), 7.23 (1H, t, J = 7.4 Hz), 7.31 (1H, d, J = 8.4 Hz), 7.39 (2H, d, J = 8.0 Hz), 7.61-7.58 (1H, m), 7.67 (2H, d, J = 8.0 Hz), 7.77 (1H, s), 7.95 (1H, d, J = 7.6 Hz), 8.08 (1H, t, J = 8.8 Hz), 8.69 (1H, d, J = 4.0 Hz). |
| 146 | | ¹H NMR (400 MHz, DMSO-D₆) δ: 4.45 (2H, d, J = 6.0 Hz), 5.13 (1H, t, J = 6.0 Hz), 7.24 (2H, d, J = 8.4 Hz), 7.41-7.35 (3H, m), 7.64-7.54 (3H, m), 7.70 (1H, d, J = 7.2 Hz), 7.82 (1H, s), 8.09 (1H, t, J = 7.6 Hz), 8.71 (1H, d, J = 4.4 Hz). |
| 147 | | ¹H NMR (400 MHz, DMSO-D₆) δ: 4.45 (2H, d, J = 6.0 Hz), 5.12 (1H, t, J = 5.6 Hz), 7.23 (2H, d, J = 8.0 Hz), 7.35 (1H, q, J = 5.1 Hz), 7.40 (2H, d, J = 8.4 Hz), 7.57-7.52 (1H, m), 7.65-7.61 (2H, m), 7.87 (1H, s), 7.99-7.96 (1H, m), 8.69 (1H, d, J = 2.4 Hz), 8.72 (1H, d, J = 6.0 Hz). |
| 148 | | ¹H NMR (400 MHz, DMSO-D₆) δ: 4.45 (2H, d, J = 5.6 Hz), 5.17 (1H, t, J = 5.6 Hz), 7.01 (1H, d, J = 7.6 Hz), 7.24 (1H, t, J = 7.8 Hz), 7.40-7.34 (3H, m), 7.44 (1H, d, J = 8.0 Hz), 7.49 (2H, d, J = 6.8 Hz), 7.59-7.54 (3H, m), 7.61 (1H, s), 7.64-7.62 (1H, m). |

TABLE 1-continued

| Example | Structural formula | ¹H NMR |
|---|---|---|
| 149 | | ¹H NMR (400 MHz, DMSO-D$_6$) δ: 2.14 (6H, s), 3.29 (2H, s), 7.25-7.20 (3H, m), 7.32 (1H, d, J = 6.4 Hz), 7.45 (2H, d, J = 4.8 Hz), 7.69-7.61 (2H, m), 7.85 (1H, s), 7.97 2H, d, J = 7.2 Hz), 8.68 (1H, d, J = 1.6 Hz), 8.72 (1H, d, J = 3.6 Hz). |
| 150 | | ¹H NMR (400 MHz, DMSO-D$_6$) δ: 2.00-1.93 (2H, m), 3.09 (4H, t, J = 7.0 Hz), 3.46 (2H, s), 7.18 (2H, d, J = 8.4 Hz), 7.40-7.36 (3H, m), 7.59-7.54 (1H, m), 7.65-7.63 (2H, m), 7.85 (1H, s), 7.98 (1H, d, J = 8.4 Hz), 8.73-8.69 (2H, m). |
| 151 | | ¹H NMR (400 MHz, DMSO-D$_6$) δ: 2.14 (6H, s), 3.30 (2H, s), 6.97 (1H, d, J = 7.2 Hz), 7.23 (1H, t, J = 7.8 Hz), 7.36-7.33 (2H, m), 7.50-7.42 (4H, m), 7.59-7.53 (3H, m), 7.64-7.60 (2H, m). |
| 152 | | ¹H NMR (400 MHz, DMSO-D$_6$) δ: 1.96-1.90 (2H, m), 3.09 (4H, t, J = 7.0 Hz), 3.45 (2H, s), 6.94 (1H, d, J = 9.2 Hz), 7.20 (1H, t, J = 7.8 Hz), 7.39-7.33 (3H, m), 7.43 (1H, s), 7.49 (2H, d, J = 8.4 Hz), 7.59-7.54 (3H, m), 7.64-7.60 (2H, m). |
| 153 | | ¹H NMR (400 MHz, DMSO-D$_6$) δ: 2.00-1.93 (2H, m), 3.11 (4H, t, J = 6.78 Hz), 3.48 (2H, s), 7.18 (2H, d, J = 8.4 Hz), 7.23 (1H, t, J = 7.6 Hz), 7.31 (1H, d, J = 8.4 Hz), 7.41 (2H, d, J = 8.4 Hz), 7.68-7.61 (1H, m), 7.82 (1H, s), 7.96 (2H, d, J = 7.6 Hz), 8.67 (1H, s), 8.72 (1H, d, J = 4.4 Hz). |
| 154 | | ¹H NMR (400 MHz, DMSO-D$_6$) δ: 1.93-1.92 (2H, m), 3.08 (4H, t, J = 6.8 Hz), 3.45 (2H, s), 7.17 (2H, d, J = 8.8 Hz), 7.39-7.35 (3H, m), 7.66-7.53 (3H, m), 7.68 (1H, d, J = 8.0 Hz), 7.92 (1H, brs), 8.11-8.06 (1H, m), 8.70 (1H, dd, J = 4.8 Hz, 1.2 Hz). |
| 155 | | ¹H NMR (400 MHz, DMSO-D$_6$) δ: 2.15 (6H, s), 3.32 (2H, s), 7.22 (2H, d, J = 8.8 Hz), 7.38 (1H, q, J = 4.7 Hz), 7.43 (2H, d, J = 8.4 Hz), 7.60-7.55 (1H, m), 7.66-7.62 (2H, m), 7.88 (1H, s), 8.00-7.97 (1H, m), 8.70 (1H, d, J = 2.0 Hz), 8.73 (1H, d, J = 6.4 Hz). |

TABLE 1-continued

| Example | Structural formula | ¹H NMR |
|---|---|---|
| 156 | (6-ethyl-3-phenyl-2-((4-(hydroxymethyl)phenyl)amino)quinazolin-4(3H)-one) | ¹H NMR (500 MHz, CDCl₃) δ: 1.28 (3H, t, J = 7.6 Hz), 1.60 (1H, t, J = 6.0 Hz), 2.74 (2H, q, J = 7.6 Hz), 4.65 (2H, d, J = 5.8 Hz), 5.92 (1H, s), 7.31 (2H, d, J = 8.5 Hz), 7.41 (2H, d, J = 7.3 Hz), 7.46 (1H, d, J = 8.3 Hz), 7.54-7.48 (3H, m), 7.61 (1H, t, J = 7.4 Hz), 7.66 (2H, t, J = 7.5 Hz), 7.99 (1H, d, J = 1.8 Hz). |
| 157 | (6-chloro-3-(pyridin-2-yl)-2-((4-(hydroxymethyl)phenyl)amino)quinazolin-4(3H)-one) | ¹H NMR (400 MHz, DMSO-D₆) δ: 4.47 (2H, d, J = 5.6 Hz), 5.15 (1H, t, J = 5.6 Hz), 7.25 (1H, s), 7.27 (1H, s), 7.33 (1H, d, J = 8.4 Hz), 7.40 (2H, d, J = 8.8 Hz), 7.64-7.61 (1H, m), 7.72-7.67 (2H, m), 7.89 (1H, d, J = 2.4 Hz), 7.95 (1H, s), 8.12 (1H, dt, J = 7.8 Hz, 2.0 Hz), 8.72 (1H, d, J = 6.0 Hz). |
| 158 | (6-ethyl-3-phenyl-2-((4-((dimethylamino)methyl)phenyl)amino)quinazolin-4(3H)-one) | ¹H NMR (400 MHz, DMSO-D₆) δ: 1.21 (3H, t, J = 7.6 Hz), 2.69 (2H, q, J = 7.7 Hz), 2.13 (6H, s), 7.19 (2H, d, J = 8.4 Hz), 7.30-7.24 (2H, m), 7.46 (4H, dd, J = 17.6 Hz, 7.7 Hz), 7.59-7.53 (2H, m), 7.62 (2H, t, J = 7.4 Hz), 7.79 (1H, d, J = 1.8 Hz). |
| 159 | (6-isopropyl-3-phenyl-2-((4-(hydroxymethyl)phenyl)amino)quinazolin-4(3H)-one) | ¹H NMR (400 MHz, DMSO-D₆) δ: 1.23 (6H, d, J = 6.9 Hz), 2.98 (1H, dt, J = 13.8 Hz, 6.9 Hz), 4.45 (2H, d, J = 5.7 Hz), 5.11 (1H, t, J = 5.7 Hz), 7.22 (2H, d, J = 8.4 Hz), 7.29-7.25 (2 H, m), 7.41 (2H, d, J = 8.4 Hz), 7.47 (2H, d, J = 7.2 Hz), 7.63-7.58 (4 H, m), 7.79 (1H, d, J = 2.0 Hz). |
| 160 | (6-isopropyl-3-phenyl-2-(phenylamino)quinazolin-4(3H)-one) | ¹H NMR (500 MHz, DMSO-D₆) δ: 1.23 (6H, d, J = 6.9 Hz), 2.99 (1H, dt, J = 13.9 Hz, 6.8 Hz), 7.05 (1H, t, J = 7.3 Hz), 7.31-7.26 (4H, m), 7.48 (4H, t, J = 7.2 Hz), 7.63-7.56 (4H, m), 7.80 (1H, d, J = 1.8 Hz). |
| 161 | (6-fluoro-3-(pyridin-2-yl)-2-((4-((dimethylamino)methyl)phenyl)amino)quinazolin-4(3H)-one) | ¹H NMR (400 MHz, CD₃OD) δ: 2.28 (6H, s), 3.49 (2H, s), 7.30 (2H, d, J = 8.4 Hz), 7.52-7.44 (4H, m), 7.74-7.65 (3H, m), 8.16 (1H, t, J = 8.6 Hz), 8.76 (1H, d, J = 5.2 Hz). |
| 162 | (6-chloro-3-phenyl-2-((3-((dimethylamino)methyl)phenyl)amino)quinazolin-4(3H)-one · HCOOH) | ¹H NMR (400 MHz, CD₃OD) δ: 2.68 (6H, s), 4.03 (2H, s), 7.22 (1H, d, J = 7.6 Hz), 7.44-7.40 (2H, m), 7.56-7.49 (3H, m), 7.60 (1H, s), 7.72-7.64 (4H, m), 8.03 (1H, d, J = 2.4 Hz), 8.53 (1H, s). |

TABLE 1-continued

| Example | Structural formula | ¹H NMR |
|---|---|---|
| 163 | 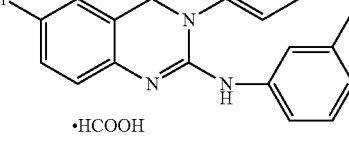 ·HCOOH | ¹H NMR (400 MHz, CD$_3$OD) δ: 2.44-2.36 (2H, m), 3.91 (4H, t, J = 7.8 Hz), 4.12 (2H, s), 7.17 (1H, d, J = 7.6 Hz), 7.44-7.38 (2H, m), 7.51-7.49 (3H, m), 7.59 (1H, s), 7.72-7.65 (4H, m), 8.03 (1H, s), 8.55 (1H, s). |
| 164 | 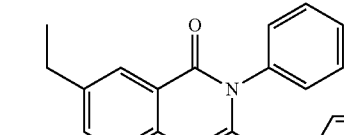 | ¹H NMR (500 MHz, DMSO-D$_6$) δ: 1.20 (3 H, t, J = 7.6 Hz), 2.68 (2 H, q, J = 7.6 Hz), 7.05 (1 H, t, J = 7.4 Hz), 7.30-7.27 (4H, m), 7.50-7.47 (4H, m), 7.59-7.53 (2H, m), 7.63-7.61 (2H, m), 7.79 (1H, d, J = 1.9 Hz). |
| 165 | 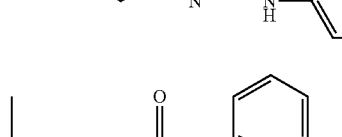 | ¹H NMR (500 MHz, CDCl$_3$) δ: 1.30 (6H, d, J = 6.9 Hz), 2.62 (6H, s), 3.02 (1H, dt, J = 13.9 Hz, 6.8 Hz), 3.91 (2H, s), 6.04 (1H, s), 7.36 (2H, d, J = 8.6 Hz), 7.42-7.39 (2H, m), 7.50 (1H, d, J = 8.4 Hz), 7.59 (1H, dd, J = 8.5 Hz, 2.1 Hz), 7.67-7.64 (3H, m), 7.71-7.68 (2H, m), 8.04 (1H, d, J = 2.1 Hz). |
| 166 | 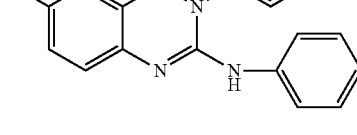 | ¹H NMR (500 MHz, DMSO-D$_6$) δ: 7.12 (1H, t, J = 7.5 Hz), 7.32 (2H, t, J = 8.0 Hz), 7.46 (3H, t, J = 8.0 Hz), 7.53 (2H, d, J = 8.7 Hz), 7.64-7.56 (3H, m), 7.78 (1H, s), 7.91 (1H, dd, J = 7.0 Hz, 2.5 Hz), 8.18 (1H, s). |
| 167 | 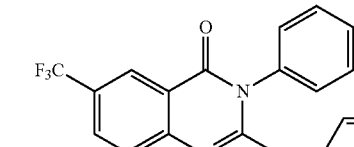 | ¹H NMR (500 MHz, DMSO-D$_6$) δ: 7.34 (2H, d, J = 9.0 Hz), 7.53 (4H, d, J = 8.5 Hz), 7.72-7.66 (3H, m), 8.44 (1H, d, J = 2.5 Hz), 8.70 (1H, d, J = 2.5 Hz). |
| 168 | 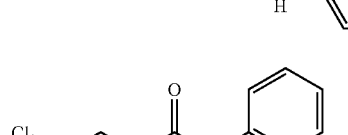 ·HCOOH | ¹H NMR (400 MHz, DMSO-D$_6$) δ: 2.19 (6H, s), 3.45 (2H, s), 7.22 (2H, d, J = 6.8 Hz), 7.35 (1H, d, J = 8.8 Hz), 7.45-7.42 (2H, m), 7.64-7.61 (1H, m), 7.72-7.68 (2H, m), 7.90 (1H, d, J = 2.4 Hz), 7.96 (1H, s) 8.15-8.09 (2H, m), 8.71 (1H, d, J = 4.8 Hz). |
| 169 | 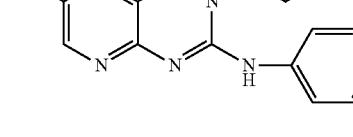 ·HCOOH | ¹H NMR (400 MHz, DMSO-D$_6$) δ: 2.09-2.02 (2H, m), 3.48-3.40 (4H, m), 3.67 (2H, s), 7.24 (2H, d, J = 8.0 Hz), 7.34 (1H, d, J = 8.8 Hz), 7.43 (2H, d, J = 8.0 Hz), 7.64-7.61 (1H, m), 7.71-7.68 (2H, m), 7.90 (1H, d, J = 2.4 Hz), 7.96 (1H, s), 8.11 (1H, t, J = 8.0 Hz), 8.16 (1H, s), 8.71 (1H, d, J = 5.2 Hz). |

TABLE 1-continued

| Example | Structural formula | ¹H NMR |
|---|---|---|
| 170 | | ¹H NMR (500 MHz, DMSO-D$_6$) δ: 1.20 (3H, t, J = 7.6 Hz), 2.69 (2H, q, J = 7.5 Hz), 7.29 (1H, d, J = 8.4 Hz), 7.35-7.31 (2H, m), 7.48 (3H, dd, J = 9.6 Hz, 8.1 Hz), 7.58-7.54 (4H, m), 7.60 (2H, dd, J = 8.1 Hz, 6.5 Hz), 7.79 (1H, d, J = 1.8 Hz). |
| 171 | | ¹H NMR (500 MHz, DMSO-D$_6$) δ: 1.20 (3H, t, J = 7.6 Hz), 1.99-1.93 (2H, m), 2.71-2.63 (2H, m), 3.08 (4H, t, J = 6.9 Hz), 3.44 (2H, s), 7.15 (2H, d, J = 8.4 Hz), 7.23 (1H, s), 7.27 (1H, d, J = 8.3 Hz), 7.40 (2H, d, J = 8.2 Hz), 7.46 (2H, d, J = 7.5 Hz), 7.55 (2H, dd, J = 13.0 Hz, 7.9 Hz), 7.60 (2H, t, J = 7.5 Hz), 7.77 (1 H, s). |
| 172 | | ¹H NMR (500 MHz, DMSO-D$_6$) δ: 1.23 (6H, d, J = 7.0 Hz), 1.98-1.95 (2H, m), 2.99-2.97 (1H, m), 3.13 (4H, s), 3.49 (2H, s), 7.17 (2H, d, J = 8.5 Hz), 7.23 (1H, s), 7.29 (1H, d, J = 8.5 Hz), 7.41 (2H, d, J = 8.5 Hz), 7.46 (2H, d, J = 7.0 Hz), 7.62-7.55 (4H, m), 7.79 (1H, d, J = 2.0 Hz). |
| 173 | | ¹H NMR (400 MHz, DMSO-D$_6$) δ: 4.47 (2H, d, J = 5.6 Hz), 5.17 (1H, t, J = 5.6 Hz), 7.38 (1H, d, J = 8.8 Hz), 7.43 (1H, d, J = 8.8 Hz), 7.52 (2H, d, J = 6.8 Hz), 7.64-7.55 (3H, m), 7.78 (1H, s), 7.91 (1H, dd, J = 8.8 Hz, 2.07 Hz), 8.17 (1H, s). |
| 174 | | ¹H NMR (500 MHz, DMSO-D$_6$) δ: 4.47 (2H, d, J = 5.5 Hz), 5.15 (1H, t, J = 5.5 Hz), 7.25 (1H, d, J = 8.0 Hz), 7.32 (2H, d, J = 9.0 Hz), 7.40 (2H, d, J = 8.0 Hz), 7.69-7.63 (2H, m), 7.89 (1H, d, J = 2.5 Hz), 8.00-7.99 (2H, m), 8.71 (1H, d, J = 2.5 Hz), 8.73 (1H, dd, J = 4.8 Hz, 1.3 Hz). |
| 175 | | ¹H NMR (500 MHz, DMSO-D$_6$) δ: 1.23 (6H, d, J = 6.9 Hz), 2.99 (1H, dt, J = 13.7 Hz, 6.9 Hz), 7.34-7.29 (3H, m), 7.50-7.46 (3 H, m), 7.57-7.52 (3H, m), 7.63-7.58 (3H, m), 7.80 (1H, d, J = 2.1 Hz). |
| 176 | | ¹H NMR (400 MHz, DMSO-D$_6$) δ: 7.38 (2H, d, J = 8.8 Hz), 7.46 (1H, d, J = 8.4 Hz), 7.53-7.51 (4H, m), 7.64-7.57 (3H, m), 7.92 (1H, dd, J = 12 Hz, 2.0 Hz), 7.95 (1H, s), 8.18 (1H, s). |

TABLE 1-continued

| Example | Structural formula | ¹H NMR |
|---|---|---|
| 177 | | ¹H NMR (500 MHz, DMSO-D₆) δ: 2.16 (6H, s), 8.18 (1H, s), 7.24 (2H, d, J = 7.0 Hz), 7.46-7.42 (3H, m), 7.52 (1H, d, J = 7.5 Hz), 7.63-7.56 (3H, m), 7.77 (1H, s), 7.91 (1H, d, J = 9.0 Hz). |
| 178 | | ¹H NMR (400 MHz, DMSO-D₆) δ: 1.96 (2H, p, J = 7.0 Hz), 3.08 (4H, t, 6.8 Hz), 3.47 (2H, s), 7.21 (2H, d, J = 8.4 Hz), 7.38 (2H, d, 8.0 Hz), 7.44 (1H, d, J = 8.4 Hz), 7.52 (2H, d, J = 6.8 Hz), 7.65-7.55 (3H, m), 7.74 (1H, s), 7.91 (1H, dd, J = 8.8 Hz, 2.0 Hz), 8.17 (1H, s). |
| 179 | | ¹H NMR (400 MHz, DMSO-D₆) δ: 4.48 (2H, d, J = 5.6 Hz), 5.17 (1H, t, J = 5.8 Hz), 7.27 (2H, d, J = 8.4 Hz), 7.41 (2H, d, J = 8.0 Hz), 7.54 (2H, d, J = 7.2 Hz), 7.65-7.58 (3H, m), 7.92 (1H, s), 8.27 (1H, d, J = 2.8 Hz), 8.73 (1H, d, J = 2.8 Hz). |
| 180 | ·HCOOH | ¹H NMR (400 MHz, DMSO-D₆) δ: 2.19 (6H, s), 3.42 (2H, s), 7.23 (2H, d, J = 8.4 Hz), 7.34 (1H, d, J = 8.8 Hz), 7.43 (2H, d, J = 7.2 Hz), 7.69 (2H, dd, J = 8.8 Hz, 2.4 Hz), 7.89 (1H, d, J = 2.4 Hz), 7.99 (2H, d, J = 8.0 Hz), 8.82 (2H, s). |
| 181 | | ¹H NMR (500 MHz, CD₃OD) δ: 2.29 (6H, s), 3.53 (2H, s), 7.32 (2H, d, J = 8.5 Hz), 7.52 (4H, t, J = 8.7 Hz), 7.72-7.64 (3H, m), 8.44 (1H, d, J = 3.0 Hz), 8.69 (1H, d, J = 3.0 Hz). |
| 182 | | ¹H NMR (400 MHz, DMSO-D₆) δ: 1.95-2.02 (2H, m), 3.14 (4H, t, J = 7.0 Hz), 3.52 (2H, s), 7.22 (2H, d, J = 8.8 Hz), 7.38 (2H, d, J = 8.0 Hz), 7.52 (2H, d, J = 6.8 Hz), 7.63-7.58 (3H, m), 8.28 (2H, d, J = 2.8 Hz), 8.73 (1H, d, J = 2.8 Hz). |
| 183 | | ¹H NMR (400 MHz, DMSO-D₆) δ: 2.12-2.05 (2H, m), 3.50-3.43 (4H, m), 7.27 (2 H, d, J = 7.6 Hz), 3.75 (2H, s), 7.34 (1H, d, J = 8.8 Hz), 7.45 (2H, d, J = 8.0 Hz), 7.65 (1H, dd, J = 7.8 Hz, 5.0 Hz), 7.69 (1H, dd, J = 8.4 Hz, 2.0 Hz), 7.90 (1H, d, J = 1.6 Hz), 7.99 (1H, d, J = 8.4 Hz), 8.03 (1H, s), 8.70 (1H, s), 8.73 (1H, d, J = 4.4 Hz). |

TABLE 1-continued

| Example | Structural formula | ¹H NMR |
|---|---|---|
| 184 | | ¹H NMR (400 MHz, DMSO-D$_6$) δ: 1.94 (2H, quin, J = 7.0 Hz), 3.10 (4H, t, J = 7.0 Hz), 3.45 (2H, s), 7.24-7.18 (2H, m), 7.40-7.28 (4H, m), 7.94 (1H, d, J = 7.6 Hz), 7.48 (2H, t, J = 7.2 Hz), 7.68-7.35 (4H, m), 7.97 (1H, d, J = 8.0 Hz,). |
| 185 | | ¹H NMR (400 MHz, DMSO-D$_6$) δ: 7.09 (1H, t, J = 7.4 Hz), 7.23-7.27 (1H, m), 7.31 (3H, t, J = 8.0 Hz), 7.40-7.44 (1H, m), 7.47-7.51 (3H, m), 7.60-7.66 (2H, m), 7.67-7.70 (1H, m), 7.97 (1H, dd, J = 1.2 Hz, 8.0 Hz), 8.00 (1H, s). |
| 186 | ·HCOOH | ¹H NMR (400 MHz, DMSO-D$_6$) δ: 7.11 (4H, d, J = 7.4 Hz), 7.21-7.25 (1H, m), 7.30 (3H, q, J = 7.2 Hz), 7.40 (2H, d, J = 7.6 Hz), 7.64-7.69 (1H, m), 7.76-7.83 (3H, m), 7.91-8.00 (3H, m). |
| 187 | | ¹H NMR (400 MHz, DMSO-D$_6$) δ: 2.11 (3H, s), 7.09 (1H, d, J = 7.2 Hz), 7.22-7.34 (4H, m), 7.39-7.50 (7H, m), 7.65-7.69 (1H, m), 7.98 (1H, dd, J = 1.2 Hz, 8.0 Hz). |
| 188 | | ¹H NMR (400 MHz, DMSO-D$_6$) δ: 1.13 (3H, t, J = 7.6 Hz), 2.61 (2H, q, J = 7.2 Hz), 6.39 (2H, s), 6.56-6.60 (1H, m), 6.74 (1H, dd, J = 1.2 Hz, 8.4 Hz, 1 H), 7.17-7.29 (5H, m), 7.69 (1H, dd, J = 1.2 Hz, 7.8 Hz), 9.62 (1H, s). |

Test Examples

While pharmacological test results for the representative compounds of the invention are shown below to explain the pharmacological effect of the compounds, the present invention is not limited to the Test Examples.

Test Example 1: Test Measuring the Nerve Hyperexcitation Suppressing Activity Using Rat Primary Culture Neurons (1) Rat Fetal Primary Culture Neurons The cerebral cortex was extracted from embryonic day 18 Wistar rats (Charles River Laboratories Japan), and cells were isolated and subjected to culture. Specifically, the fetus was retrieved from pregnant rats that were euthanized by $CO_2$ inhalation. The fetal brain was extracted in ice-cooled 10 mM Hepes (Thermo Fisher Scientific, cat #15630-080)/1 mM sodium pyruvate (FUJIFILM Wako Pure Chemical, cat #190-14881)/0.49 w/v % D(+) glucose (FUJIFILM Wako Pure Chemical, cat #079-05511)-containing Hank's buffer (HBSS) (Thermo Fisher Scientific, cat #14175-095). The cerebral cortex was then recovered under a stereo microscope. The tissue was dispersed by incubating for 5 minutes at 37° C. in a 0.3 mg/mL papain (Sigma-Aldrich, cat #P4762), 0.1 mg/mL DNase I (Roche, cat #11284932001), and 5 mM magnesium chloride solution. The dispersion reaction was suspended by adding a medium comprising 10% fetal bovine serum. After washing with HBSS, the tissue was physically dispersed by pipetting. Cell clumps were removed through a 70 μm cell strainer (Becton Dickinson, cat #352350) to obtain a neuron suspension. The suspension was centrifuged for 4 minutes at 1000 rpm to remove the supernatant. After resuspending the cells in a small amount of HBSS, the cells were counted. The neurons were diluted in a medium to achieve a density of 3×104 cells per well and seeded on a 384-well plate (Corning, cat #356697) coated with poly-D-lysine. As the medium, Neurobasal Electro medium (Thermo Fisher Scientific, cat #A14098-01) comprising GlutaMAX (Thermo Fisher Scientific, cat #35050061), penicillin/streptomycin (Thermo Fisher Scientific, cat #15140-122), and 2% B27 Electro Supplement (Thermo Fisher Scientific, cat #A14097-01) was used. The seeded cells were cultured for 15 to 17 days in a 37° C. incubator under 5% $CO_2$. On the day after seeding the cells, the culture solution was exchanged with a fresh medium comprising 3 μM cytarabine (Sigma-Aldrich, cat #C1768). ⅔ of the medium was exchanged with a fresh medium (cytarabine free) thereafter once every 3 to 4 days.

(2) Fluorescent Calcium Probe Treatment, Addition of Compound, and Evaluation of Intracellular Calcium Concentration The entire culture solution was removed on day 15 to day 17 of culture. 30 μL of medium for measurement comprising a fluorescent calcium probe (Molecular Device, product name: FLIPR Calcium 6 Assay Bulk Kit, cat #R8191) was added. The culture was left standing for 2 to 4 hours and then subjected to measurement. As the medium for measurement, 20 mM Hepes (Thermo Fisher Scientific, cat #15630-080) and 0.1% bovine serum albumin (Sigma-Aldrich, cat #A9576)-containing Hank's buffer (Thermo Fisher Scientific, cat #14065-056) was used.

The test compounds were serially diluted with a dimethyl sulfoxide (DMSO) solution so that the final concentration would be 0.1 to 30 μM. First, the compounds were diluted to a 333-fold concentration of the final concentration with DMSO, and then diluted with a medium for measurement to prepare a concentrate with a 5-fold concentration of the final concentration.

The intensity of fluorescence of a calcium probe was measured over time with FDSS7000EX (Hamamatsu Photonics) to evaluate the change in intracellular calcium concentrations. Compounds were added using FDSS7000EX. After 120 seconds from adding 10 μL of test compound solutions, 10 μL of 4-aminopyridine solution (final concentration of 100 μM) (FUJIFILM Wako Pure Chemical, cat#016-02781) was added for an addition 6 minutes and 30 seconds measurement of fluorescence intensity. The frequency of calcium oscillation induced by 4-arninopyridine was quantified as an indicator of nerve excitation. With 100% as the mean frequency of wells treated with DMSO as a control, the inhibitory activity (%) at each serial dilution concentration of the test compounds was determined, and the 50% inhibitory concentration (IC50) or inhibition rate (%) at a certain concentration was determined for each test compound. Table 2 shows inhibitory activity data for representative compounds.

TABLE 2-1

| Example | IC50 |
|---|---|
| 1 | 0.4 |
| 2 | 1.1 |
| 3 | 0.2 |
| 4 | 0.8 |
| 5 | 22.1 |
| 6 | 43%@30 μM |
| 7 | 1.8 |
| 8 | 1.2 |
| 9 | 83%@1 μM |
| 10 | 7.2 |
| 11 | 86%@0.1 μM |
| 12 | 0.4 |
| 13 | 1.6 |
| 14 | 0.3 |
| 15 | 0.8 |
| 16 | 3.3 |
| 17 | 5.9 |
| 18 | 85%@1 μM |
| 19 | 1.2 |
| 20 | 63%@1 μM |
| 21 | 0.6 |
| 22 | 0.8 |
| 23 | 10.7 |
| 24 | 2.4 |
| 25 | 9.0 |
| 26 | 19%@0.1 μM |
| 27 | 21%@10 μM |
| 28 | 44%@10 μM |
| 29 | 13%@30 μM |
| 30 | 2.2 |
| 31 | 8.9 |
| 32 | 7.9 |
| 33 | 0.6 |
| 34 | 7.9 |
| 35 | 3.4 |
| 36 | 17.2 |
| 37 | 16.5 |
| 38 | 8.8 |
| 39 | 10.0 |
| 40 | 0.4 |
| 41 | 0.6 |
| 42 | 12.4 |
| 43 | 0.3 |
| 44 | 4.5 |
| 45 | 18%@30 μM |
| 46 | 9.2 |
| 47 | 2.5 |
| 48 | 0.9 |
| 49 | 1.7 |
| 50 | 4.3 |

TABLE 2-1-continued

| Example | IC50 |
|---|---|
| 51 | 3.6 |
| 52 | 2.0 |
| 53 | 19.1 |
| 54 | 28.5 |
| 55 | 7.3 |
| 56 | 0.7 |
| 57 | 7.6 |
| 58 | 4.6 |
| 59 | 59%@0.1 μM |
| 60 | 2.6 |
| 61 | 2.6 |
| 62 | 0.8 |
| 63 | 0.3 |
| 64 | 1.1 |
| 65 | 1.1 |
| 66 | 10.2 |
| 67 | 0.2 |
| 68 | 50%@0.1 μM |
| 69 | 0.1 |
| 70 | 0.1 |
| 71 | 14%@10 μM |
| 72 | 0.9 |
| 73 | 49%@30 μM |
| 74 | 1.0 |
| 75 | 4.8 |
| 76 | 0.7 |
| 77 | 3.9 |
| 78 | 2.2 |
| 79 | 1.2 |
| 80 | 0.6 |
| 81 | 5.4 |
| 82 | 1.8 |
| 83 | 0.3 |
| 84 | 3.8 |
| 85 | 1.0 |
| 86 | 1.1 |
| 87 | 3.5 |
| 88 | 2.6 |
| 89 | 2.8 |
| 90 | 0.2 |
| 91 | 11.5 |
| 92 | 0.6 |
| 93 | 6.6 |
| 94 | 0.3 |
| 95 | 9.7 |
| 96 | 18.0 |
| 97 | 7.0 |
| 98 | 17.3 |
| 99 | 3.1 |
| 100 | 14%@10 μM |
| 101 | 0.4%@30 μM |
| 102 | 2.4 |
| 103 | 33%@30 μM |
| 104 | 16%@10 μM |
| 105 | 41%@10 μM |
| 106 | 35%@0.1 μM |
| 107 | 78%@0.1 μM |
| 108 | 2.2 |
| 109 | 7.9 |
| 110 | 25%@10 μM |
| 111 | 83%@0.1 μM |
| 112 | 4.6 |
| 113 | 6.8 |
| 114 | 2.7 |
| 115 | 5.3 |
| 116 | 2.9 |
| 117 | 1.3 |
| 118 | 1.4 |
| 119 | 1.1 |
| 120 | 6.2 |
| 121 | 1.8 |
| 122 | 0.5 |
| 123 | 0.4 |
| 124 | 6.7 |
| 125 | 6.4 |
| 126 | 11.7 |
| 127 | 17%@30 μM |
| 128 | 31%@30 μM |
| 129 | 36%@10 μM |
| 130 | 0.2 |
| 131 | 86%@1 μM |
| 132 | 0.1 |
| 133 | 18%@30 μM |
| 134 | 20%@30 μM |
| 135 | 10%@30 μM |
| 136 | 0.2 |
| 137 | 7%@30 μM |
| 138 | 29.4 |
| 139 | 18%@30 μM |
| 140 | 1%@30 μM |
| 141 | 19%@30 μM |
| 142 | 28%@30 μM |
| 143 | 6.7 |
| 144 | 13%@10 μM |
| 145 | 15%@30 μM |
| 146 | 20%@30 μM |
| 147 | 47%@30 μM |
| 148 | 7.6 |
| 149 | 10%@10 μM |
| 150 | 0.3%@30 μM |
| 151 | 7.8 |
| 152 | 7.0 |
| 153 | 17%@30 μM |
| 154 | 7%@0.1 μM |
| 155 | 6%@10 μM |
| 156 | 7.4 |
| 157 | 19%@30 μM |
| 158 | 17%@30 μM |
| 159 | 7.9 |
| 160 | 25.4 |
| 161 | 22%@0.1 μM |
| 162 | 5.7 |
| 163 | 17%@30 μM |
| 164 | 5.4 |
| 165 | 44%@30 μM |
| 166 | 11.9 |
| 167 | 7.8 |
| 168 | 10%@30 μM |
| 169 | 4%@30 μM |
| 170 | 10.8 |
| 171 | 35%@30 μM |
| 172 | 46%@30 μM |
| 173 | 9.8 |
| 174 | 41%@30 μM |
| 175 | 4%@30 μM |
| 176 | 21%@30 μM |
| 177 | 40%@30 μM |
| 178 | 45%@30 μM |
| 179 | 36%@30 μM |
| 180 | 23%@30 μM |
| 181 | 17%@30 μM |
| 182 | 26%@30 μM |
| 183 | 9%@30 μM |
| 184 | 12.8 |
| 185 | 5.5 |
| 186 | 7.4 |
| 187 | 0.6 |
| 188 | 1.2 |

As shown in these tables, the compound of the invention had inhibitory activity in a nerve hyperexcitation suppression test using rat primary culture.

Test Example 2: Hyperexcitation Suppression Test Using Motor Neurons Induced to Differentiate from iPS Cells Derived from Amyotrophic Lateral Sclerosis Patient (1) Induction of Differentiation from iPS Cells to Motor Neurons An iPS cell line from ALS patients (clone name: CiRA00123, obtained from the Center for iPS Cell Research and Application, Kyoto University) was induced to differentiate into motor neurons. The cells of the patients were confirmed to have a mutation that replaces the 337$^{th}$ methionine residue in the amino acid sequence of TAR DNA-binding protein 43 (TDP-43) with a valine residue. Mitomycin treated SNL cells (Cell Biolabs, cat #CBA-316) were used as feeder cells for seeding iPS cells. SNL cells were treated with mitomycin as follows. First, a 10 cm petri dish (Iwaki, cat #3020-100) was treated with 0.1% gelatin (FUJIFILM Wako Pure Chemical, cat #190-15805) for more than 1 hour in a 37° C. incubator under 5% $CO_2$. The gelatin was then removed by aspiration. 1 to 2×106 thawed SNL cells were seeded using a medium for SNL cells [DMEM (Sigma-Aldrich, cat #D6429), penicillin/streptomycin (Thermo Fisher Scientific, cat #15140-122), and fetal bovine serum (Thermo Fisher Scientific, cat #10437-028)]. The cells were diluted 8 to 16-fold every 3 to 4 days, and passaged and grown to the required number of cells. Subsequently, 2 to 4×106 SNL cells were seeded on a 0.1% gelatin treated 15 cm petri dish (Iwaki, cat #3030-150) and cultured to 80 to 90% confluence. Mitomycin C (Kyowa Kirin, YJ code: 4231400D1031) diluted to 0.4 mg/mL with the medium for SNL cells was then added so that the final concentration would be 6.2 µg/mL. After leaving the culture standing for 2 hours and 15 minutes in a 37° C. incubator under 5% $CO_2$, the medium was removed, and the cells were washed once with PBS. 2.5% trypsin/EDTA (Thermo Fisher Scientific, cat #15090-046) was diluted with PBS (final concentration of 0.25%) and then added to cells. After leaving the cells standing for 1 minute at room temperature, the cells were recovered in a tube. After centrifugation, the cells were suspended in CELLBANKER® (Zenoaq Resource, cat #CB011) and cryopreserved. Differentiation of iPS cells was induced as follows. First, 0.1% gelatin was added to a 10 cm petri dish (Iwaki, cat #3020-100) for treatment for over an hour in a 37° C. incubator under 5% $CO_2$. SNL cells treated with mitomycin were suspended using a medium for SNL cells. 1.5×106 cells were seeded on the 10 cm petri dish and cultured for 2 to 3 days. The medium for SNL cells was subsequently removed. After washing with PBS, iPS cells suspended in a medium for primate ES/iPS cells (ReproCELL, cat #RCHEMD001B) comprising penicillin/streptomycin and Y-27632 (Tocris, cat #1254) were seeded. The medium was exchanged every day, from two days after seeding until the start of differentiation induction. Y-27632 was then added to the cell culture supernatant for exposure to a concentration of 10 µM for more than 1 hour. The culture supernatant was removed and the cells were washed with phosphate buffer (PBS) (Nacalai Tesque, cat #14249-24). A CTK solution (ReproCELL, product name: Cell dissociation solution, cat #RCHETP002) was then added and reacted for 1 minute at room temperature. The CTK solution was removed, and the cells were washed twice with PBS. 1 mL of medium for primate ES/iPS cells (ReproCELL, cat #RCHEMD001B) comprising penicillin/streptomycin was then added. The cells were peeled off with a cell scraper. The cell clumps were dispersed through a cell strainer (Becton Dickinson, cat #352350). The resulting suspension was transferred to a 6-well plate (Corning, cat #3471). The medium was replaced with a medium prepared from adding 0.3 µM LDN193189 (Stemgent, cat #04-0074)/2 µM SB431542 (Tocris, cat #1614)/3 µM CHIR-99021 (Stemgent, cat #04-0004-10)/10 µM Y-27632 to mixture medium A [DMEM/Ham's F12 GlutaMAX (Thermo Fisher Scientific, cat #10565-018), 2 mM L-glutamine (Thermo Fisher Scientific, cat #25030-081), Non-Essential Amino Acid (NEAA) (Thermo Fisher Scientific, cat #11140-050), penicillin/streptomycin, 2 µg/mL Heparin (Sigma-Aldrich, H-4784), and N2 supplement (Thermo Fisher Scientific, cat #17502-048)]. The medium was cultured in a 37° C. incubator under 5% $CO_2$ (day 0 of culture). On day 2 and day 4 of culture, the culture solution was removed with a pipette, and was replaced with a fresh medium prepared from adding 0.3 µM LDN193189/2 µM SB431542/3 µM CHIR-99021 to the mixture medium A described above. On day 7, day 9, and day 11 of culture, the culture solution was removed with a pipette, and was replaced with a fresh medium prepared from adding 0.3 µM LDN193189/2 µM SB431542/3 µM CHIR-99021/0.5 µM Purmorphamine (FUJIFILM Wako Pure Chemical, cat #166-23991)/0.1 µM Retinoic acid (Sigma-Aldrich, cat #R2625) to the mixture medium A described above. On day 14 and day 16 of culture, the culture solution was removed with a pipette, and was replaced with a fresh medium prepared from adding 0.5 µM Purmorphamine/0.1 µM Retinoic acid/10 ng/mL Human BDNF/200 µM Ascorbic acid (Sigma-Aldrich, cat #A5960) to the mixture medium A described above. On day 18 of culture, the medium was replaced with a fresh medium prepared from adding 0.5 µM Purmorphamine/0.1 µM Retinoic acid/0.1 µM Compound E (Calbiochem, cat #565790) to mixture medium B [Neurobasal medium Electro (Thermo Fisher Scientific, cat #A14098-01), 2 mM L-glutamine, NEAA, Antibiotic-Antimycotic (Thermo Fisher Scientific, cat #15240-062), 2 µg/mL Heparin, N2 supplement, 10 ng/mL IGF-1 (PeproTech, cat #100-11), 10 ng/mL Human CNTF (PeproTech, cat #450-13), 10 ng/mL Human GDNF (R&D Systems, cat #212-GD-050), B27 supplement, Electro (Thermo Fisher Scientific, cat #A14097-01), 200 µM Ascorbic acid, and 10 ng/mL Human BDNF]. On day 21 of culture, the cell clump was washed with PBS and then centrifuged to remove the supernatant. The cells were incubated for 10 minutes at 37° C. after adding Accutase (Innovative Cell Technologies, Cat #AT104) and 10 µM Y27632. After ice cooling the cells, the cell clumps were dispersed by pipetting. After centrifugation (300×g, 5 minutes, 4° C.), the precipitate was recovered and suspended in mixture medium B. This was repeated twice. The resulting motor neuron-like cells were suspended in CELLBANKER®, dispensed, and cryopreserved.

(2) Culture to Maturate Motor Neurons

Rat astrocytes (Cell Applications, cat #CAR882A05n) were thawed and suspended in a Rat Astrocyte Medium Set (Cell Applications, cat #CAR821K500). The astrocytes were then centrifuged to remove the supernatant and resuspended in the same medium. The rat astrocytes were seeded on a 0.1% gelatin coated 384-well plate (Thermo Fisher Scientific, Cat #142761) at 3000 cells/well, and cultured in a 37° C. incubator under 5% $CO_2$. The culture solution was exchanged every other day. The astrocytes were cultured until reaching confluence. The motor neurons that were cryopreserved in the previous section were then thawed and suspended in a medium prepared from adding 25 µM 2-mercaptoethanol (Thermo Fisher Scientific, cat #21985-0123)/0.1% bovine serum albumin (Sigma-Aldrich, cat #A9576)/Culture One Supplement (Thermo Fisher Scientific, A3320201)/0.1 µM Compound E to mixture medium B (=mixture medium C). The neurons were then centrifuged to remove the supernatant and resuspended in mixture medium C. The motor neurons were seeded on the 384-well plate, on which the rat astrocytes were seeded, at 8000 cells/well, and cultured for 25 days in a 37° C. incubator under 5% $CO_2$. Mixture medium C was exchanged at a frequency of every other day. From day 7 from starting culture and onwards, a medium with the composition of mixture medium C excluding Culture One Supplement/Compound E (0.1 µM) was used for exchanging the medium.

(3) Fluorescent Calcium Probe Treatment, Addition of Compound, and Evaluation of Intracellular Calcium Concentration The entire culture solution was removed on day 25 of culture. 30 µL of medium for measurement comprising a fluorescent calcium probe (Molecular Device, product name: FLIPR Calcium 6 Assay Bulk Kit, cat #R8191) was added in accordance with the manufacturer's recommended protocol. The medium was left standing for 2 to 4 hours at room temperature. As the medium for measurement, a mixture of 10 mM Hepes, 0.1% bovine serum albumin (Sigma-Aldrich, cat #A9576), 1 mM sodium pyruvate (FUJIFILM Wako Pure Chemical, cat #190-14881), and 0.5 w/v % D(+)-Glucose Solution (FUJIFILM Wako Pure Chemical, cat #079-05511)-containing Hank's buffer (Thermo Fisher Scientific, cat #14175-095) was used.

The test compounds were serially diluted with a dimethyl sulfoxide (DMSO) solution so that the final concentration would be 0.1 to 30 µM. First, the compounds were diluted to a 333-fold concentration of the final concentration with DMSO, and then diluted with a medium for measurement to prepare a concentrate with a 5-fold concentration of the final concentration.

The intensity of fluorescence of a calcium probe was measured over time with FDSS7000EX (Hamamatsu Photonics) to evaluate the change in intracellular calcimn concentration. compounds were added using FDSS7000EX. After 120 seconds from adding 10 µl of test compound solutions, 10 µl of 4-aminopyridine solution (final concentration: 100 µm) (FUJIFILM Wako PURE CHEMICAL, cat #016-02781) was added for an additional 5 minute measurement of fluorescence intensity. The frequency of calcium oscillation induced by 4-aminopyridine was quantified as an indicator of nerve excitation with 100% as the mean frequency of wells treated with DMSO as a control, the inhibitory activity (%) at each serial dilution concentration of the test compounds was determined, and the 50% inhibitory concentration (IC50) was determined for each test compound. Table 3 shows inhibitory activity data for representative compounds.

TABLE 3-1

| Example | IC50 |
|---|---|
| 1 | 1.2 |
| 2 | 0.2 |
| 3 | 10.0 |
| 4 | 6.0 |
| 5 | 99%@1 µM |
| 6 | 13.3 |
| 7 | 2.1 |
| 8 | 0.5 |
| 9 | 2.0 |
| 10 | 13.1 |
| 11 | 2.0 |
| 12 | 27.5 |
| 13 | 2.5 |
| 14 | 1.7 |
| 15 | 4.8 |
| 16 | 2.5 |
| 17 | 1.0 |
| 18 | 4.9 |
| 19 | 1.3 |
| 20 | 8.7 |
| 21 | 2.9 |
| 22 | 1.8 |
| 23 | 2.8 |

TABLE 3-1-continued

| Example | IC50 |
|---|---|
| 24 | 4.3 |
| 25 | 2.9 |
| 26 | 6.8 |
| 27 | 6.2 |
| 28 | 3.6 |
| 29 | 7.4 |
| 30 | 1.0 |
| 31 | 2.4 |
| 32 | 13.3 |
| 33 | 21.6 |
| 34 | 2.4 |
| 35 | 0.6 |
| 36 | 0.3 |
| 37 | 0.8 |
| 38 | 2.9 |
| 39 | 4.7 |
| 40 | 7.2 |
| 41 | 25%@10 µM |
| 42 | 3.4 |
| 43 | 25%@10 µM |
| 44 | 4%@10 µM |
| 45 | 3.9 |
| 46 | 6.0 |
| 47 | 14.2 |
| 48 | 1.2 |
| 49 | 13.3 |
| 50 | 17.8 |
| 51 | 2.5 |
| 52 | 12.5 |
| 53 | 4.5 |
| 54 | 13%@30 µM |
| 55 | 15%@10 µM |
| 56 | 25.5 |
| 57 | 44%@10 µM |
| 58 | 4.8 |
| 59 | 5.5 |
| 60 | 6.4 |
| 61 | 42%@10 µM |
| 62 | 1.9 |
| 63 | 2.6 |
| 64 | 2.4 |
| 65 | 3.0 |
| 66 | 22.2 |
| 67 | 3.2 |
| 68 | 9.7 |
| 69 | 11.4 |
| 70 | 0.9 |
| 71 | 2.9 |
| 72 | 16.1 |
| 73 | 18%@30 µM |
| 74 | 18.6 |
| 75 | 16.4 |
| 76 | 31.6 |
| 77 | 16.6 |
| 78 | 3.5 |
| 79 | 0.8 |
| 80 | 42%@10 µM |
| 81 | 24%@30 µM |
| 82 | 10.9 |
| 83 | 2.0 |
| 84 | 3%@30 µM |
| 85 | 15.7 |
| 86 | 25%@10 µM |
| 87 | 22.5 |
| 88 | 30%@30 µM |
| 89 | 14.9 |
| 90 | 4.1 |
| 91 | 30%@30 µM |
| 92 | 2.8 |
| 93 | 17%@30 µM |
| 94 | 24%@30 µM |
| 95 | 23%@30 µM |
| 96 | 27.2 |
| 97 | 21.0 |
| 98 | 40%@30 µM |
| 99 | 24.2 |
| 100 | 17.4 |
| 101 | 4.3 |

TABLE 3-1-continued

| Example | IC50 |
|---|---|
| 102 | 6.1 |
| 103 | 12.5 |
| 104 | 21.6 |
| 105 | 24.8 |
| 106 | 17.3 |
| 107 | 1.9 |
| 108 | 2.0 |
| 109 | 2.8 |
| 110 | 13%@10 μM |
| 111 | 2%@10 μM |
| 112 | 6%@1 μM |
| 113 | 24.1 |
| 114 | 11.0 |
| 115 | 21%@30 μM |
| 116 | 2.5 |
| 117 | 4.7 |
| 118 | 1.6 |
| 119 | 3.1 |
| 120 | 35%@30 μM |
| 121 | 35%@30 μM |
| 122 | 2.2 |
| 123 | 2.0 |
| 124 | 8%@10 μM |
| 125 | 36%@30 μM |
| 126 | 2%@1 μM |
| 127 | 21%@10 μM |
| 128 | 3%@10 μM |
| 129 | 4%@10 μM |
| 130 | 9%@10 μM |
| 131 | 30%@30 μM |
| 132 | 21%@10 μM |
| 133 | 27%@30 μM |
| 134 | 44%@30 μM |
| 135 | 4%@10 μM |
| 136 | 8%@0.1 μM |
| 137 | 19%@10 μM |
| 138 | 4.4 |
| 139 | 5%@10 μM |
| 140 | 17%@10 μM |
| 141 | 3%@10 μM |
| 142 | 4%@10 μM |
| 143 | 7.5 |
| 144 | 2.6%@10 μM |
| 145 | 4.3%@10 μM |
| 146 | 7.8%@10 μM |
| 147 | 20%@10 μM |
| 148 | 1.7 |
| 149 | 5.2%@10 μM |
| 150 | 15%@10 μM |
| 151 | 10.3 |
| 152 | 9.4 |
| 153 | 12%@μM |
| 154 | 1.9%@10 μM |
| 155 | 10%@10 μM |
| 156 | 3.8 |
| 157 | 14%@10 μM |
| 158 | 3.0 |
| 159 | 4.4 |
| 160 | 4.6 |
| 161 | 16%@10 μM |
| 162 | 2.6 |
| 163 | 11.2 |
| 164 | 20.2 |
| 165 | 12.9 |
| 166 | 22.4 |
| 167 | 9.8 |
| 168 | 26.6 |
| 169 | 23.5 |
| 170 | 23.4 |
| 171 | 8.1 |
| 172 | 7.5 |
| 173 | 15.6 |
| 174 | 19.7 |
| 175 | 5.9%@30 μM |
| 176 | 25%@10 μM |
| 177 | 13.1 |
| 178 | 3.3 |
| 179 | 9.6%@30 μM |
| 180 | 40%@30 μM |
| 181 | 32%@30 μM |
| 182 | 19.9 |
| 183 | 35%@30 μM |
| 184 | 15.8 |
| 185 | 93%@10 μM |
| 186 | 97%@10 μM |
| 187 | 2.5 |
| 188 | 1.0 |

As shown in these tables, the compound of the invention exhibited inhibitory activity in a hyperexcitation suppression test using motor neurons induced to differentiate from iPS cells derived from amyotrophic lateral sclerosis patients.

Test Example 3: Evaluation of Model Subcutaneously Injected with Pentetrazol (Minimum Seizure Model, scPTZ)

This test evaluates the antiseizure effect of a drug. The model animal used in this test is a system expressing generalized absence seizure or myoclonic seizure. 3, 10, 30, and 100 mg/kg of the test compound (Example 1) was orally administered to male Slc:ddY mice (group of five, body weight: 20 to 30 g), and 85 mg of pentetrazol/kg was subcutaneously administered 1 hour later. The presence/absence of expression of clonic seizure during 30 minutes was then observed. 0.5% methylcellulose solution was administered for the control. The following table shows the results.

TABLE 4

| | scPTZ (positive count/test count) | | | |
|---|---|---|---|---|
| Example | 3 mg/kg | 10 mg/kg | 30 mg/kg | 100 mg/kg |
| 1 | 3/5 | 5/5 | 5/5 | 5/5 |

As shown in this Table, the compound of the invention exhibited an antiseizure effect in the evaluation of a model subcutaneously injected with pentetrazol (minimum seizure model, scPTZ).

Test Example 4: Evaluation of Effect of Suppressing Progression of Movement Disorder in Wobbler Mice (Amyotrophic Lateral Sclerosis Model)

This test evaluates the protective effect of a test compound on the progression of movement disorder by using Wobbler mice exhibiting a symptom of a motor neuron disease (Mitsumoto H. et al., (1994) Ann. Neurol. 36, 142-148; Mitsumoto H. et al., (1994) Science, 265, 1107-1110).

Wobbler mice found to have a symptom such as shivering or low body weight at 3 weeks old were subjected to the test. First, to conduct a test on motor functions, i.e., a rotarod test, 300 seconds of walking training was conducted on a rotating bar (8 to 10 rpm) for 3 consecutive days for acclimation to the device. Subsequently, a rotarod test (10 rpm, 300 seconds) was conducted at 4 weeks old to evaluate the motor function prior to drug administration. The walking time on the rotating bar was measured. The maximum value of three runs was found and determined as the walking time of each individual.

Individuals were then assigned to administration groups. Individuals with a rotarod test walking time prior to drug administration of 210 seconds or longer were subjected to the test. Stat Preclinica (Takumi Information Technology Inc.) was used for the grouping. "Multivariate block assignment" was performed using the rotarod test walking time, body weight, grip strength of both front limbs (measured using a grip strength tester (Muromachi Kikai, MK-380CM/R)), and front limb deformation score (total value of left and right limbs from scoring the deformation on the left and right limbs in accordance with Mitsumoto H. et al., (1994) Ann. Neurol. 36, 142-148) as indicators. The male and female mice were separately assigned to four different groups. A group had a total of 16 male and female mice.

A drug was administered for 6 weeks after separating the mice into test compound administration group (3 doses) and control group (no drug) at 4 week old. The test compound was mixed into powdered feeds (CE-2; CLEA Japan) at a concentration of 0.25, 0.5, and 1.0 mg/g of feed, and administered by voluntary intake.

A rotarod test was conducted as a blind test where the evaluator was not aware of the dosing condition. The test was repeated at a frequency of twice a week until the conclusion of drug administration. The results are shown in FIG. 1.

As shown in the FIGURE, the compound of the invention exhibited an effect of suppressing progression of movement disorders in Wobbler mice (amyotrophic lateral sclerosis model).

As disclosed above, the present invention is exemplified by the use of its preferred embodiments. However, it is understood that the scope of the present invention should be interpreted solely based on the Claims. The present application claims priority to Japanese Patent Application No. 2019-158612 (filed on Aug. 30, 2019). The entire content thereof is incorporated herein by reference. It is also understood that any patent, any patent application, and any references cited herein should be incorporated herein by reference in the same manner as the contents are specifically described herein.

INDUSTRIAL APPLICABILITY

The compound of the invention exhibits efficacy on epilepsy and amyotrophic lateral sclerosis animal models and is useful as an antiepileptic drug and amyotrophic lateral sclerosis therapeutic drug.

The invention claimed is:
1. A compound selected from:
   2-anilino-6-fluoro-3-phenylquinazolin-4(3H)-one,
   2-{4-[(azetidin-1-yl)methyl]anilino}-6-chloro-3-phenylquinazolin-4(3H)-one and
   6-chloro-2-{4-[(3,3-difluorazetidin-1-yl)methyl]anilino}-3-phenylquinazolin-4(3H)-one or a pharmaceutically acceptable salt thereof.
2. The compound of claim 1, wherein the compound is 2-anilino-6-fluoro-3-phenylquinazolin-4(3H)-one, or pharmaceutically acceptable salt thereof.
3. The compound of claim 1, wherein the compound is 2-{4-[(azetidin-1-yl)methyl]anilino}-6-chloro-3-phenylquinazolin-4(3H)-one, or pharmaceutically acceptable salt thereof.
4. The compound of claim 1, wherein the compound is 6-chloro-2-{4-[(3,3 difluoroazetidin-1-yl)methyl]anilino}-3-phenylquinazolin-4(3H)-one, or pharmaceutically acceptable salt thereof.
5. A pharmaceutical composition comprising an effective amount of the compound or pharmaceutically acceptable salt thereof according to claim 1.
6. A pharmaceutical composition comprising an effective amount of the compound or pharmaceutically acceptable salt thereof according to claim 1, and one or more pharmaceutically acceptable excipient.
7. A pharmaceutical composition comprising an effective amount of the compound or pharmaceutically acceptable salt thereof according to claim 2.
8. A pharmaceutical composition comprising an effective amount of the compound or pharmaceutically acceptable salt thereof according to claim 2, and one or more pharmaceutically acceptable excipient.
9. A pharmaceutical composition comprising an effective amount of the compound or pharmaceutically acceptable salt thereof according to claim 3.
10. A pharmaceutical composition comprising an effective amount of the compound or pharmaceutically acceptable salt thereof according to claim 3, and one or more pharmaceutically acceptable excipient.
11. A pharmaceutical composition comprising an effective amount of the compound or pharmaceutically acceptable salt thereof according to claim 4.
12. A pharmaceutical composition comprising an effective amount of the compound or pharmaceutically acceptable salt thereof according to claim 4, and one or more pharmaceutically acceptable excipient.

* * * * *